US009139876B1

(12) United States Patent
Shriver et al.

(10) Patent No.: US 9,139,876 B1
(45) Date of Patent: Sep. 22, 2015

(54) METHOD OF ANALYZING A PREPARATION OF A LOW MOLECULAR WEIGHT HEPARIN

(75) Inventors: Zachary Shriver, Cambridge, MA (US); Naveen Bhatnagar, Framingham, MA (US); Nur Sibel Gunay, Brookline, MA (US); Jennifer Ozug, Norwood, MA (US); Elaine Y. Sun, Cambridge, MA (US)

(73) Assignee: MOMENTA PHARMACUETICALS, INC., Cambridge, MA (US)

( * ) Notice: Subject to any disclaimer, the term of this patent is extended or adjusted under 35 U.S.C. 154(b) by 1208 days.

(21) Appl. No.: 12/151,003

(22) Filed: May 2, 2008

Related U.S. Application Data

(60) Provisional application No. 60/915,791, filed on May 3, 2007.

(51) Int. Cl.
*C12Q 1/68* (2006.01)

(52) U.S. Cl.
CPC .................................. *C12Q 1/6883* (2013.01)

(58) Field of Classification Search
None
See application file for complete search history.

(56) References Cited

U.S. PATENT DOCUMENTS

| | | |
|---|---|---|
| 3,832,253 A | 8/1974 | DiPalma |
| 3,854,480 A | 12/1974 | Zaffaroni |
| 4,452,775 A | 6/1984 | Kent |
| 4,652,555 A | 3/1987 | Goulay et al. |
| 4,667,014 A | 5/1987 | Nestor, Jr. et al. |
| 4,686,288 A | 8/1987 | Lormeau et al. |
| 4,687,765 A | 8/1987 | Vairel et al. |
| 4,692,435 A | 9/1987 | Lormeau |
| 4,748,034 A | 5/1988 | de Rham |
| 4,791,195 A | 12/1988 | Bianchini et al. |
| 4,826,827 A | 5/1989 | Lormeau et al. |
| 4,847,338 A | 7/1989 | Linhardt et al. |
| 4,916,219 A | 4/1990 | Linhardt et al. |
| 4,933,326 A | 6/1990 | Bianchini et al. |
| 4,977,250 A | 12/1990 | Diaz et al. |
| 4,981,955 A | 1/1991 | Lopez |
| 4,990,502 A | 2/1991 | Lormeau et al. |
| 5,010,063 A | 4/1991 | Piani et al. |
| 5,013,724 A | 5/1991 | Petitou et al. |
| 5,013,725 A | 5/1991 | Isomura et al. |
| 5,019,649 A | 5/1991 | Lormeau et al. |
| 5,032,679 A | 7/1991 | Brandley et al. |
| 5,039,529 A | 8/1991 | Bergendal et al. |
| 5,084,564 A | 1/1992 | Vila et al. |
| 5,104,860 A | 4/1992 | Piani et al. |
| 5,106,734 A | 4/1992 | Nielsen |
| 5,110,918 A | 5/1992 | Casu et al. |
| 5,164,378 A | 11/1992 | Conti et al. |
| 5,239,660 A | 8/1993 | Ooi |
| 5,264,425 A | 11/1993 | Dal Pozzo et al. |
| 5,296,471 A | 3/1994 | Holme et al. |
| 5,340,932 A | 8/1994 | Fussi et al. |
| 5,380,716 A | 1/1995 | Conrad et al. |
| 5,389,618 A | 2/1995 | Debrie |
| 5,403,827 A | 4/1995 | De-Ambrosi |
| 5,410,039 A | 4/1995 | Ungarelli et al. |
| 5,430,132 A | 7/1995 | Silvano et al. |
| 5,430,133 A | 7/1995 | Piani et al. |
| 5,599,801 A | 2/1997 | Branellec et al. |
| 5,668,118 A | 9/1997 | Kennedy |
| 5,696,100 A | 12/1997 | Holme et al. |
| 5,707,973 A | 1/1998 | Baron et al. |
| 5,707,974 A | 1/1998 | Kennedy |
| 5,721,973 A | 2/1998 | Mizukawa |
| 5,763,421 A | 6/1998 | Caretto et al. |
| 5,767,269 A | 6/1998 | Hirsh et al. |
| 5,783,570 A | 7/1998 | Yokota et al. |
| 5,808,021 A | 9/1998 | Holme et al. |
| 5,849,721 A | 12/1998 | Uzan |
| 5,912,237 A | 6/1999 | Kennedy |
| 5,922,358 A | 7/1999 | Doutremepuich et al. |
| 5,935,850 A | 8/1999 | Clark et al. |
| 5,958,899 A | 9/1999 | Zoppetti et al. |
| 6,045,805 A | 4/2000 | Moreau |
| 6,075,013 A | 6/2000 | Weitz et al. |
| 6,077,683 A | 6/2000 | Kennedy |
| 6,143,730 A | 11/2000 | Parish et al. |
| 6,197,943 B1 | 3/2001 | Casu et al. |
| 6,217,863 B1 * | 4/2001 | Godavarti et al. ............ 424/94.5 |
| 6,228,998 B1 | 5/2001 | Miura et al. |
| 6,232,093 B1 | 5/2001 | Van Houdenhoven et al. |
| 6,255,296 B1 | 7/2001 | Daniels |
| 6,258,798 B1 | 7/2001 | Wallentin |
| 6,346,517 B1 * | 2/2002 | Wong et al. ...................... 514/56 |
| 6,384,021 B1 | 5/2002 | Mardiguian |

(Continued)

FOREIGN PATENT DOCUMENTS

| | | |
|---|---|---|
| EP | 121067 B1 | 10/1984 |
| EP | 244235 B1 | 11/1987 |

(Continued)

OTHER PUBLICATIONS

Thanawiroon et al. (J. of Chromatography, vol. 1014, p. 215-223, 2003).*
Rota et al. (Analytical Biochemistry, vol. 344, 2005, pp. 193-203).*
Harenberg (Thromb. Res., 127, 2011, S100-S104).*
Luo et al. (J. Cellular Biochem, vol. 97, pp. 1241-1258, 2006).*
Ampofo, S. et al., "Disaccharide Compositional Analysis of Heparin and Heparan Sulfate Using Capillary Zone Electrophoresis," *Analytical Biochem.*, 199:249-255 (1991).
Da Col, R. et al., "Characterization of the Chemical Structure of Sulphated Glycosaminoglycans After Enzymatic Digestion. Application for Liquid Chromatography—Mass Spectrometry with an Atmospheric Pressure Interface," *J. of Chromatography*, 647:289-300 (1993).

(Continued)

*Primary Examiner* — Hope Robinson

(74) *Attorney, Agent, or Firm* — Lando & Anastasi, LLP

(57) ABSTRACT

Methods for analyzing mixtures of polysaccharides, for example heparin such as unfractionated heparin and enoxaparin are described. In some instances, the mixtures are analyzed using high performance liquid chromatography (HPLC), e.g., reverse phase HPLC.

5 Claims, 8 Drawing Sheets

(56) References Cited

U.S. PATENT DOCUMENTS

| | | | |
|---|---|---|---|
| 6,492,503 B1 | 12/2002 | Kariya et al. | |
| 6,617,316 B1 | 9/2003 | Mourier et al. | |
| 6,812,221 B2* | 11/2004 | McKeehan et al. | 514/56 |
| RE38,743 E | 6/2005 | Debrie | |
| 7,008,933 B2* | 3/2006 | Welzel | 514/56 |
| 7,083,937 B2 | 8/2006 | Sasisekharan et al. | |
| 7,390,633 B2* | 6/2008 | Liu et al. | 435/41 |
| 7,575,886 B2* | 8/2009 | Venkataraman et al. | 435/18 |
| 7,585,642 B2* | 9/2009 | Sasisekharan et al. | 435/13 |
| 7,687,579 B2* | 3/2010 | Takahashi et al. | 525/240 |
| 7,691,612 B2* | 4/2010 | Myette | 435/85 |
| 7,790,466 B1* | 9/2010 | Shriver et al. | 436/94 |
| 7,811,827 B2* | 10/2010 | Raguram | 436/87 |
| 7,816,144 B1* | 10/2010 | Shriver et al. | 436/94 |
| 7,947,507 B2 | 5/2011 | Venkataraman et al. | |
| 7,968,082 B1 | 6/2011 | Shriver et al. | |
| 8,003,402 B2* | 8/2011 | Yamamoto et al. | 436/164 |
| 8,076,149 B1 | 12/2011 | Shriver et al. | |
| 8,101,733 B1 | 1/2012 | Shriver et al. | |
| 8,252,597 B1 | 8/2012 | Shriver et al. | |
| 8,435,795 B2 | 5/2013 | Beccati et al. | |
| 8,435,799 B2 | 5/2013 | Schrier et al. | |
| 8,597,957 B2 | 12/2013 | Schrier et al. | |
| 8,617,896 B1 | 12/2013 | Shriver et al. | |
| 8,715,953 B2 | 5/2014 | Kaundinya et al. | |
| 2002/0169143 A1 | 11/2002 | Sasisekharan et al. | |
| 2003/0203385 A1 | 10/2003 | Venkataraman et al. | |
| 2004/0198697 A1 | 10/2004 | Cohen et al. | |
| 2004/0265943 A1 | 12/2004 | Viskov et al. | |
| 2005/0119477 A1 | 6/2005 | Mourier et al. | |
| 2005/0186679 A1 | 8/2005 | Viskov et al. | |
| 2005/0215519 A1 | 9/2005 | Viskov et al. | |
| 2005/0288252 A1 | 12/2005 | Nurcombe et al. | |
| 2006/0024664 A1 | 2/2006 | Sasisekharan et al. | |
| 2006/0182734 A1* | 8/2006 | Liu et al. | 424/94.61 |
| 2007/0065921 A1 | 3/2007 | Sasisekharan et al. | |
| 2007/0098708 A1 | 5/2007 | Myette | |
| 2007/0134226 A1 | 6/2007 | Myette | |
| 2007/0161073 A1 | 7/2007 | Sasisekharan et al. | |
| 2007/0287683 A1 | 12/2007 | Shriver et al. | |
| 2008/0009069 A1 | 1/2008 | Mourier et al. | |
| 2008/0318328 A1 | 12/2008 | Viskov et al. | |
| 2009/0061411 A1 | 3/2009 | Venkataraman et al. | |
| 2010/0050748 A1 | 3/2010 | Schrier et al. | |
| 2010/0279269 A1 | 11/2010 | Parsons et al. | |
| 2010/0305022 A1 | 12/2010 | Shriver et al. | |
| 2011/0207919 A1 | 8/2011 | Beccati et al. | |
| 2011/0288046 A1 | 11/2011 | Venkataraman et al. | |
| 2013/0065852 A1 | 3/2013 | Venkataraman et al. | |
| 2014/0114056 A1 | 4/2014 | Gunay et al. | |

FOREIGN PATENT DOCUMENTS

| | | |
|---|---|---|
| EP | 244236 A2 | 11/1987 |
| EP | 245813 B1 | 11/1987 |
| EP | 268885 B1 | 6/1988 |
| EP | 293539 A2 | 12/1988 |
| EP | 302034 B1 | 2/1989 |
| EP | 319559 A1 | 6/1989 |
| EP | 347588 B1 | 12/1989 |
| EP | 423151 B1 | 9/1993 |
| EP | 380943 B1 | 9/1994 |
| EP | 432537 B1 | 1/1995 |
| EP | 483733 B1 | 8/1996 |
| EP | 623629 B1 | 8/1996 |
| EP | 625166 B1 | 9/1997 |
| EP | 557887 B1 | 12/1997 |
| EP | 708785 B1 | 3/1999 |
| EP | 693499 B1 | 12/1999 |
| EP | 789777 B1 | 8/2000 |
| EP | 970130 B1 | 7/2002 |
| EP | 735050 B1 | 9/2002 |
| EP | 1580197 | 9/2005 |
| EP | 1582531 | 10/2005 |
| EP | 1586588 | 10/2005 |
| JP | 11230935 A | 8/1999 |
| WO | 8809347 A1 | 12/1988 |
| WO | WO9003791 A1 | 4/1990 |
| WO | 9914326 A1 | 3/1999 |
| WO | 0065521 A2 | 11/2000 |
| WO | WO 01/29055 | 4/2001 |
| WO | 0223190 A2 | 3/2002 |
| WO | 0232406 A2 | 4/2002 |
| WO | WO 03/078960 | 9/2003 |
| WO | WO 2004/027087 | 4/2004 |
| WO | WO 2005/009040 | 1/2005 |
| WO | 2005090411 A1 | 9/2005 |
| WO | WO 2005/080438 | 9/2005 |
| WO | WO 2005/090411 | 9/2005 |

OTHER PUBLICATIONS

Desai, U. et al., "Oligosaccharide Composition of Heparin and Low-molecular-weight Heparins by Capillary Electrophoresis," *Analytical Biochem.*, 213:120-127 (1993).

Ernst, S. et al., "Direct Evidence for Predominantly Exolytic Processive Mechanism for Depolymerization of Heparin-like Glycosaminoglycans by Heparinase I," *PNAS*, 95:4182-4187 (1998).

Guo, Y. et al., "The Disaccharide of Heparins and Heparan Sulfates," *Analytical Biochem.*, 176:96-104 (1989).

Imanari, T. et al., "High-performance Liquid Chromatographic Analysis of Glycosaminoglycan-derived Oligosaccharides," *J. of Chromatography A*, 720:275-293 (1996).

Karamanos, N. et al., "Ion-pair High-performance Liquid Chromatography for Determining Disaccharide Composition in Heparin and Heparan Sulphate," *J. of Chromatography A*, 765:169-179 (1997).

Kariya, Y. et al., "Disaccharide Analysis of Heparin and Heparan Sulfate Using Deaminative Cleavage with Nitrous Acid and Subsequent Labeling with Paranitrophenyl Hydrazine," *J. Biochem.* (Tokyo), 123(2):240-6 (1998) Abstract Only.

Kinoshita, A. et al., "Microanalysis of Glycosaminoglycan-derived Oligosaccharides Labeled with a Fluorophore 2-aminobenzamide by High-performance Liquid Chromatography: Application to Disaccharide Composition Analysis of Exosequencing of Oligosaccharides," *Analytical Biochem.*, 269:367-378 (1999).

Lamari, F. et al., "Analysis of Glycosaminoglycan-derived Disaccharides in Biologic Samples by Capillary Electrophoresis and Protocol for Sequencing Glycosaminoglycans," *Biomedical Chromatography*, 16:95-102 (2002).

Lee, G. et al., "Separation of Reduced Disaccharides Derived from Glycosaminoglycans by High-performance Liquid Chromatography," *J. of Chromatography*, 212:65-73 (1981).

Lindhart, R. et al., "Mapping and Quantification of the Major Oligosaccharide Components of Heparin," *Biochem. Journal*, 254:781-787 (1988).

Linhardt, R. et al., "Oligosaccharide Mapping of Low Molecular Weight Heparins: Structure and Activity Differences," *J. of Medicinal Chem.*, 33(6):1639-1645 (1990).

Lindhardt, R. et al., "New Methodologies in Heparin Structure Analysis and the Generation of LMW Heparins," *Heparin and Related Polysaccharides*, 37-47, ed. D.A. Lane et al., Plenum Press, New York (1992).

Merchant, K. et al., "Structure of Heparin-derived Tetrasaccharides," *Biochem. Journal*, 229:369-377 (1985).

Militsopoulou, M. et al., "Determination of 12 Heparin- and Heparan Sulfate-derived Disaccharides as 2-aminoacridone Derivatives by Capillary Zone Electrophoresis Using Ultraviolet and Laser-induced Flourescence Detection," *Electrophoresis*, 23:1104-1109 (2002).

Park, Y. et al., "Purification and Characterization of Heparin Sulphate Proteoglycan from Bovine Brain," *Biochem. Journal*, 344:723-730 (1999).

Pervin, A. et al., "Separation of Glycosaminoglycan-derived Oligosaccharides by Capillary Electrophoresis Using Reverse Polarity," *Analytical Biochem.*, 221:182-188 (1994).

Rhomberg, A. et al., "Mass Spectrometric and Capillary Electrophoretic Investigation of the Enzymatic Degradation of Heparin-like Glycosaminoglycan," *PNAS*, 95;4167-4181 (1998).

(56) References Cited

OTHER PUBLICATIONS

Rice, K. et al., "High-performance Liquid Chromatographic Separation of Heparin-derived Oligosaccharides," *Analytical Biochem.*, 150(2):325-31 (1985) Abstract Only.

Ruiz-Calero, V. et al., "Pressure-assisted Capillary Electrophoresis-electrospray Ion Trap Mass Spectrometry for the Analysis of Heparin Depolymerised Disaccharides," *J. of Chromatography A*, 914:277-291 (2001).

Ruiz-Calero, V. et al., "Use of Reversed Polarity and a Pressure Gradient in the Analysis of Disaccharide Composition of Heparin by Capillary Electrophoresis," *J. of Chromatography A*, 828:497-508 (1998).

Saad, O. et al., "Compositional Analysis and Quantification of Heparin and Heparan Sulfate by Electrospray Ionization Ion Trap Mass Spectrometry," *Anal. Chem.*, 75:2985-2995 (2003).

Scapol, L. et al., "Capillary Electrophoresis of Heparin and Dermatan Sulfate Unsaturated Disaccharides with Triethylamine and Acetonitrile as Elecrolyte Additives," *J. of Chromatography A.*, 735:367-374.

Thanawiroon, C. et al., "Separation of a Complex Mixture of Heparin-derived Oligosaccharides Using Reversed-phase High-performance Liquid Chromatography," *J. of Chromatography A*, 1014:215-223 (2003).

Thanawiroon, C. et al., "Liquid Chromatography/Mass Spectrometry Sequencing Approach for Highly Sulfated Heparin-derived Oligosaccharides," *J. of Biological Chem.*, 279(4):2608-2615 (2004).

Toida, T. et al., "Structural Differences and the Presence of Unsubstituted Amino Groups in Heparan Sulphates from Different Tissues and Species," *Biochem. Journal*, 322:499-506 (1997).

Toyoda, H. et al., "Rapid and Sensitive Analysis of Disaccharide Composition in Heparin and Heparan Sulfate by Reversed-phase Ion-pair Chromatography on a 2 µm Porous Silica Gel Column," *J. of Chromatography A*, 830:197-201 (1999).

Volpi, N., "Characterization of Heparins with Different Relative Molecular Masses (from 11 600 to 1600) by Various Analytical Techniques," *J. of Chromatography*, 622:13-20 (1993).

Volpi, N., "Hyaluronic Acid and Chondroitin Sulfate Unsaturated Disaccharides Analysis by High-Performance Liquid Chromatography and Fluorimetric Detection with Dansylhydrazine," *Analytical Biochem.*, 277:19-24 (2000).

Vynios, D. et al., "Advances in Analysis of Glycosaminoglycans: Its Applications for the Assessment of Physiological and Pathological States of Connective Tissues," *J. of Chromatography B*, 781:21-38 (2002).

Yoshida, K., "Analysis of Unsaturated Disaccharides form Glycosaminoglycuronan by High-performance Liquid Chromatography," *Analytical Biochem.*, 117:327-332 (1989).

Araki et al., "Application of 2-aminopyriopyridine fluorescence labeling in the analysis of in vivo and in vitro metabolism of dextran sulfate sodium by size-exclusion high-proformance liquid chromatography", Journal of Chromatrography B: vol. 753, No. 2 pp. 209-215 (2001).

Alban et al., "Development of SPC-ELISA: A new assay principle for the study of sulfated polysaccharide-protein interactions", Journal of Biomolecular Screening, vol. 6, No. 6, pp. 393-400, (2001).

Jeske et al., Pharmacologic profile of certoparin. Expert Opinion on Investigational drugs, vol. 8, No. 3, pp. 315-327 (1999).

Kuhle et al., "Pharmacokinetic study of Tinzaparin in Pediatric Patients, Blood", vol. 100, No. 11 pp. abstract No. 3975. *abstract only* (2002).

Watt et al., "Comparison of Ovine, bovine and porcine muccosal heparins and low molecular weight heparins by disaccharide analyses and 13 C NMR" Carborhydrate Polymers, vol. 33, pp. 5-11 (1997).

Dawes et al., "The measurement of heparin and other therapeutic sulfated polysaacharides in plasma, serum and urine", Thrombosis and Haemostasis, vol. 54, No. 3, pp. 630-634, (1985).

Van Putten et al., "Determination of low molecular weight heparin in the clinical laboratory" Haemostasis, vol. 14, No. 2 pp. 205-210. (1984).

Guizzardi et al., "Pharmacokinetics and organ distribution in rate of low molecular weight heparin", Arzneimittel-Forschung, vol. 37, No. 11 pp. 1281-1283 (1987).

Supplementary Partial European Search Report from European Application No. EP037446289 dated Jul. 14, 2008.

Venkataraman, G., "Sequencing complex polysaccharides" vol. 286 (1999).

Desai et al.. "Molecular weight of low molecular weight heparins by 13C nuclear magnetic resonance spectroscopy," Carbohydrate Research, 255, (1994) pp. 193-212.

Malsch et al., "High-resolution capillary electrophoresis and polyacrylamide gel electophoresis of heparins," Journal of Chromatography A. 716. (1995) pp. 258-268.

Sundaram et al., "Rational design of low-molecular weight heparins with improved in vivo activity," PNAS, 100(2), Jan. 21, 2003, pp. 651-656.

Bianchini et al. "Few Bicyclic Acetals at Reducing End of Low-Molecular-Weight Heparins: Might they Restrict Specification of Pharmacopoeia?" Pharmeuropa Scientific Notes, 2005-1 pp. 1-3.

Bianchini et al. "Variability of Heparins and Heterogeneity of Low Molecular Weight Heparins" Seminars in Thrombosis and Hemostasis vol. 33, No. 5 2007 pp. 496-502.

Cerny et al. "Preparation of 2-Amino-1,6-Anhydro-2,3-Dideoxy-B-D-arabino-Hexopyranose. 1H- and 13C-N.M.R. Spectra of Deoxy Derivatives of 2-Amino-1,6-Anhydro-2-Deoxy-D-Glucose and 2-Amino-1,6-Anhydro-2-Deoxy-D-Mannose." Carbohydrate Research, 130 (1984) 103-114.

Fareed et al. "Generic Low-Molecular-Weight Heparins: Some Practical Considerations" Seminars in Thrombosis and Hemostasis. vol. 30, No. 6 2004 pp. 703-713.

Fareed et al. "Biochemical and Pharmacologic Heterogeneity in Low Molecular Weight Heparins. Impact on the Therapeutic Profile" Current Pharmaceutical Design, 2004 vol. 10, 983-999.

Guerrini et al. Low Molecular Weight Heparins: Structural Differentiation by Bidimensional nuclear magnetic Resonance Spectroscopy. Seminars in Thrombosis and Hemostasis. vol. 33, No. 5 2007 pp. 478-487.

Mascellani et al. "Characterization of di- and monosulfated, unsaturated heparin disaccharides with terminal N-sulfated 1,6-anhydro-B-D-glucosamine or N-sulfated 1,6-anhydro-B-D-mannosamine residues" Carbohydrate Research vol. 342 (2007) pp. 835-842.

Citizens Petition filed with the United States Food and Drug Administration by Aventis Pharmaceuticals Inc. on Feb. 19, 2003.

Citizens Petition Supplemental filed with the United States Food and Drug Administration by Aventis Pharmaceuticals Inc. on Feb. 12, 2004.

"2.6.26. Test for Anti-D Antibodies in Intravenous Immunoglobulin" Pharmeuropa vol. 16, No. 1, Jan. 2004 pp. 121-122.

Holzgrabe, U., Deubner, R., Scholl mayer, C., Weibel, B. (2005) Quantitative NMR spectroscopy—Applications in drug analysis. Journal of Pharmaceutical and Biomedical Analysis, v. 38, p. 806-812.

Hirano, S. (1970) NMR study of 4-deoxy-a-L-threo-4-enohexopyranosyluronic acid (1-3)2-acetamido-2-deoxy-D-hexoses produced in the enzymic digestion of hyaluronate, chondroitin and chondroitin sulfates. Organic Magnetic Resonance, vol. 2, p. 577-580.

Skipper et al., "An HLA-A2-restricted tyrosinase antigen on melanoma cells results from posttranslational modification and suggests a novel pathway for processing of membrane proteins", J. Exp. Med., 1996, vol. 183, pp. 527-534.

Skipper et al., "Shared epitopes for HLA-A3-restricted melanoma-reactive human CTL include a naturally processed epitope from Pmel-17/gp100", J. Immunol., 1996, vol. 157, pp. 5027-5033.

Sudor et al., "End-label free-solution electrophoresis of the low molecular weight heparins", Anal. Chem., 1997, vol. 69, No. 16, pp. 3199-3204.

Supplemental Partial European Search Report from European Application No. EP 037446289 dated Jul. 14, 2008.

Tahara et al., "Identification of a MAGE-2-encoded human leukocyte antigen-A24-binding synthetic peptide that induces specific antitumor cytotoxic T lymphocytes", Clin. Cancer Res., 1999, vol. 5, pp. 2236-2241.

(56) References Cited

OTHER PUBLICATIONS

Tanaka et al., "Induction of antitumor cytotoxic T lymphocytes with a MAGE-3-encoded synthetic peptide presented by human leukocytes antigen-A24", Cancer Res., 1997, vol. 57, pp. 4465-4468.
Tanzarella et al., "Identification of a promiscuous T-cell epitope encoded by multiple members of the MAGE family", Cancer Res., 1999, vol. 59, pp. 2668-2674.
Topalian et al., "Melanoma-specific CD4+ T cells recognize nonmutated HLA-DR-restricted tyrosinase epitopes", J. Exp. Med., 1996, vol. 183, pp. 1965-1971.
Traversari et al., "A nonapeptide encoded by human gene MAGE-1 is recognized on HLA-A1 by cytolytic T lymphocytes directed against tumor antigen MZ2-E", J. Exp. Med., 1992, vol. 176, pp. 1453-1457.
Trehy et al., "Analysis of heparin sodium by SAX/HPLC for contaminants and impurities", Journal of Pharmaceutical and Biomedical Analysis, 2009, vol. 49, No. 3, pp. 671-673.
Tsai et al., "Identification of subdominant CTL epitopes of the GP100 melanoma-associated tumor antigen by primary in vitro immunization with peptide-pulsed dendritic cells", J. Immunol., 1997, vol. 158, pp. 1796-1802.
Tsang et al., "Generation of human cytotoxic T cells specific for human carcinoembryonic antigen epitopes from patients immunized with recombinant vaccinia-CEA vaccine", J. Natl. Cancer Inst., 1995, vol. 87, pp. 982-990.
Tsuda et al., "The cell-surface proteoglycan Daily regulates Wingless signalling in Drosophila", Nature, 1999, vol. 400, pp. 276-280.
Turnbull et al., "A strategy for rapid sequencing of heparan sulfate and heparin saccharides", Proc. Natl. Acad. Sci. USA, 1999, vol. 96, pp. 2698-2703.
Van Den Eynde et al., "A new family of genes coding for an antigen recognized by autologous cytolytic T lymphocytes on a human melanoma", J. Exp. Med., 1995, vol. 182, pp. 689-698.
Van Der Bruggen et al., "A peptide encoded by human gene MAGE-3 and presented by HLA-A2 induces cytolytic T lymphocytes that recognize tumor cells expressing MAGE-3", Eur. J. Immunol., 1994, vol. 24, pp. 3038-3043.
Vonderheide et al., "The telomerase catalytic subunit is a widely expressed tumor-associated antigen recognized by cytotoxic T lymphocytes", Immunity, 1999, vol. 10, pp. 673-679.
Wang et al. "Cloning genes encoding MHC Claa II-restricted antigens: mutated CDC27 as a tumor antigen", Science, 1999, vol. 284, pp. 1351-1354.
Wang et al., "A breast and melanoma-shared tumor antigen: T cell response to antigenic peptides translated from different open reading frames", J. Immunol., 1998, vol. 161, pp. 3596-3606.
Wang et al., "Identification of TRP-2 as a human tumor antigen recognized by cytotoxic T lymphocytes", J. Exp. Med., 1996, vol. 184, pp. 2207-2216.
Wang et al., "Utilization of an alternative open reading frame of a normal gene in generating a novel human cancer antigen", J. Exp. Med., 1996, vol. 183, pp. 1131-1140.
Wölfel et al., "A p16INK4a-insensitive CDK4 mutant targeted by cytolytic T lymphocytes in a human melanoma", Science, 1995, vol. 269, pp. 1281-1284.
Wölfel et al., "Two tyrosinase nonapeptides recognized on HLA-A2 melanomas by autologous cytolytic T lymphocytes", Eur. J. Immunol., 1994, vol. 24, pp. 759-764.
Yates et al., "1H and 13C NMR spectral assignments of the major sequences of twelve systematically modified heparin derivatives", Carbohydrate Research, 1996, Vol. 294, pp. 15-27.
Zorn et al., "A MAGE-6-encoded peptide is recognized by expanded lymphocytes infiltrating a spontaneously regressing human primary melanoma lesion", Eur. J. Immunol., 1999, vol. 29, pp. 602-607.
Aarnoudse et al., "Interleukin-2-induced, melanoma-specific T cells recognize CAMEL, an unexpected translation product of LAGE-1" Int. J. Cancer, 1999, vol. 82, pp. 442-448.
Ansel et al., "Pharmaceutical dosage forms and drug delivery systems", 1999, pp. 23-27 and 54-59, published by Lippincott Williams & Wilkins.

Anumula et al., "High resolution and high sensitivity methods for oligosaccharide mapping and characterization by normal phase high performance liquid chromatography following derivatization with highly fluorescent anthranilic acid", Glycobiology, 1998, vol. 8, No. 7, pp. 685-694.
Bartolucci et al., "Inhibition of human leukocyte elastase by chemically and naturally oversulfated galactosaminoglycans", Carbohydrate Research, 1995, vol. 276, No. 2, pp. 401-408.
Bennett et al., "High resolution analysis of functional determinants on human tissue-type plasminogen activator", J. of Biological Chemistry, 1991, vol. 266, No. 8, pp. 5191-5201.
Bigge et al., "Nonselective and efficient fluorescent labeling of glycans using 2-amino benzamide and anthranilic acid", Anal. Biochem., 1995, vol. 230, No. 2, pp. 229-238.
Binari et al., "Genetic evidence that heparin-like glycosaminoglycans are involved in wingless signaling", Development, 1997, vol. 124, pp. 2623-2632.
Bosch et al., "Recognition of BCR-ABL positive leukemic blasts by human CD4+ T cells elicited by primary in vitro immunization with a BCR-ABL breakpoint peptide", Blood, 1996, vol. 88, pp. 3522-3527.
Bottio et al., "Life threatening anaphylactic shock caused by porcine heparin intravenous infusion during mitral valve repair," The Journal of Thoracic and Cardiovascular Surgery, 2003, vol. 126, pp. 1194-1195.
Boël et al. "Bale: a new gene encoding an antigen recognized on human melanomas by cytolytic T lymphocytes", Immunity, 1995, vol. 2, pp. 167-175.
Brichard et al., "A tyrosinase nonapeptide presented by HLA-B44 is recognized on a human melanoma by autologous cytolytic T lymphocytes", Eur. J. Immunol., 1996, vol. 26, pp. 224-230.
Brossart et al., "Her-2/neu-derived peptides are tumor-associated antigens expressed by human renal cell and colon carcinoma lines and are recognized by in vitro induced specific cytotoxic T lymphocytes", Cancer Res., 1998, vol. 58, pp. 732-736.
Brändle et al., "A mutated HLA-A2 molecule recognized by autologous cytotoxic T lymphocytes on a human renal cell carcinoma", J. Exp. Med., 1996, vol. 183, pp. 2501-2508.
Campbell, S. A., Filed by Amphastar pharmaceuticals in response to citizen petition docket No. 03P-0064/CP1 filed with the United States Food and Drug Administration. Response filed on May, 13, 2004, Entered into FDA docket system on Jun. 8, 2004.
Carlson et al., "The Determination of recombinant human tissue-type plasminogen activator activity by turbidimetry using a microcentrifugal analyzer", Analytical Biochem., 1988, vol. 168, pp. 428-435.
Castelli et al., "Mass spectromic identification of a naturally processed melanoma peptide recognized by CD8+ cytotoxic T lymphocytes", J. Exp. Med., 1995, vol. 181, pp. 363-368.
Castelli et al., "Novel HLA-Cw8-restricted T cell epitopes derived from tyrosinase-related protein-2 and gp100 melanoma antigens", J. Immunol., 1999, vol. 162, pp. 1739-1748.
Chaux et al., "Identification of five MAGE-A1 epitopes recognized by cytolytic T lymphocytes obtained by in vitro stimulation with dendritic cells transduced with MAGE-A1", J. Immunol., 1999, vol. 163, pp. 2928-2936.
Chaux et al., "Identification of MAGE-3 epitopes presented by HLA-DR molecules to CD4(+) T lymphocytes", J. Exp. Med., 1999, vol. 189, pp. 767-778.
Chiari et al., "Two antigens recognized by autologous cytolytic T lymphocytes on a melanoma result form a single point mutation in an essential housekeeping gene", Cancer Res., 1999, vol. 59, pp. 5785-5792.
Collard et al., "A novel approach to 14C lable N-linked oligosaccharides" Analyt. Biochem., 1997, vol. 247, No. 2, pp. 448-450.
Correale et al., "In vitro generation of human cytotoxic T lymphocytes specific for peptides derived from prostate-specific antigen", J. Natl. Cancer Inst., 1997, vol. 89, pp. 293-300.
Coulie et al., "A mutated intron sequence codes for an antigenic peptide recognized by cytolytic T lymphocytes on a human melanoma", Proc. Natl. Acad. Sci., 1995, vol. 92, pp. 7976-7980.

(56) References Cited

OTHER PUBLICATIONS

Coulie, "Antigens recognized on human tumors by cytolytic T lymphocytes: towards vaccination?", Stem Cells, 1995, vol. 13, pp. 393-403.
Cox et al., "Identification of a peptide recognized by five melanoma-specific human cytotoxic T cell lines", Science, 1994, vol. 264, pp. 716-719.
Dalmora et al., "Biological potency and physicochemical characterization of unfractionated heparins," Revista Brasileira de Hematologi e Hematerapia, 2009, vol. 31, No. 4, pp. 1-7.
De Backer et al., "Characterization of the GAGE genes that are expressed in various human cancers and in normal testis", Cancer Res., 1999, vol. 59, pp. 3157-3165.
Drummond et al., "Electrophoretic sequencing of heparin/heparan sulfate oligosaccharides using a highly sensitive fluorescent end label", Proteomics, 2001, vol. 1, No. 2, pp. 304-310.
Duffour et al., "A MAGE-A4 peptide presented by HLA-A2 is recognized by cytolytic T lymphocytes", Eur. J. Immunol., 1999, vol. 29, pp. 3329-3337.
Ernst et al., "Expression in *Escherichia coli*, purification and characterization of heparinase I from *Flavobacterium heparinum*", Biochem. J., 1996, vol. 315, pp. 589-597.
European Search Report from European Application Serial No. 10190250.0 dated Dec. 27, 2010.
Fisk et al., "Identification of immunodominant peptide of HER-2/neu protooncogene recognized by ovarian tumor-specific cytotoxic T lymphocyte lines", J. Exp. Med., 1995, vol. 181, pp. 2109-2117.
Franz et al., "MALDI-FTMS characterization of oligosaccharides labeled with 9-aminofluorene", J. Am. Soc. Mass Spectrom., 2001, vol. 12, No. 12, pp. 1254-1261.
Fujie et al., "A MAGE-1-encoded HLA-A24-binding synthetic peptide induces specific anti-tumor cytotoxic T lymphocytes", Int. J. Cancer, 1999, vol. 80, pp. 169-172.
Gaudin et al., "A hsp70-2 mutation recognized by CTL on a human renal cell carcinoma", J. Immunol., 1999, vol. 162, pp. 1730-1738.
Gaugler et al., "Human gene MAGE-3 codes for an antigen recognized on a melanoma by autologous cytolytic T lymphocytes", J. Exp. Med., 1994, vol. 179, pp. 921-930.
Gjertsen et al., "Cytotoxic CD4+ and CD8+ T lymphocytes, generated by mutant p21-ras (12Val) peptide vaccination of a patient, recognize 12Val-dependent nested epitopes present within the vaccine peptide and kill autologous tumour cells carrying this mutation", Int. J. Cancer, 1997, vol. 72, pp. 784-790.
Guerrini et al., "Combined quantitative 1H and 13C nuclear magnetic resonance spectroscopy for characterization of heparin preparations", Seminars in Thrombosis and Hemostasis, 2001, vol. 27, No. 5, pp. 473-482.
Guerrini et al., "Complex glycosaminoglycans: profiling substitution patterns by two-dimensional nuclear magnetic resonance spectroscopy", Analytical Biochemistry, 2005, vol. 337, pp. 35-47.
Guerrini et al., "Oversulfated chondroitin sulfate is a contaminant in heparin associated with adverse clinical events", Nature Biotechnology, Jun. 2008, vol. 26, No. 6, pp. 669-675, Nature Publishing Group US.
Guilloux et al., "A peptide recognized by human cytolytic T lymphocytes on HLA-A2 melanomas is encoded by an intron sequence of the N-acetylglucosaminyltransferase V gene", J. Exp. Med., 1996, vol. 183, pp. 1173-1183.
Guéguen et al., "An antigen recognized by autologous CTLs on a human bladder carcinoma", J. Immunol., 1998, vol. 160, pp. 6188-6194.
Hennekens et al., "Current issues concerning thrombolytic therapy of acute myocardial infarction", J. Am. Coll. Cardiol., 1995, vol. 25, No. 7, pp. 18S-22S.
Herman et al., "A peptide encoded by the human MAGE3 gene and presented by HLA-B44 induces cytolytic T lymphocytes that recognize tumor cells expressing MAGE3", Immunogenetics, 1996, vol. 43, pp. 377-383.
Hogan et al., "The peptide recognized by HLA-A68.2-restricted, squamous cell carcinoma of the lung-specific cytotoxic T lymphocytes is derived from a mutated elongation factor 2 gene", Cancer Res., 1998, vol. 58, pp. 5144-5150.
Holmes et al., "Lessons we have learned from the GUSTO trial", J. Am. Coll. Cardiol., 1995, vol. 25, No. 7, pp. 10S-17S.
Hricovini et al., "Conformational analysis of heparin epoxide in aqueous solution. An NMR relaxation study", Carbohydrate Research, 1995, vol. 277, pp. 11-23.
Huang et al., "Cytolytic T lymphocytes recognize an antigen encoded by MAGE-A10 on a human melanoma", J. Immunol., 1999, vol. 162, pp. 6849-6854.
Ikeda et al., "Characterization of an antigen that is recognized on a melanoma showing partial HLA loss by CTL expressing an NK inhibitory receptor", Immunity, 1997, vol. 6, pp. 199-208.
Imai et al., "Directional degradation of b-chitin by chitinase A1 revealed by a novel reducing end labelling technique", FEBS Lett, 2002, vol. 510, No. 3, pp. 201-205.
Amended Complaint—*Momenta Pharmaceuticals, Inc. and Sandoz Inc.*, Plaintiffs, v. *Amphastar Pharmaceuticals, Inc., International Medication Systems, Ltd., Watson Pharmaceuticals, Inc., and Watson Pharma, Inc.*, Defendants. 2011 WL 9556659.
Brief for Appellants—*Momenta Pharmaceuticals, Inc.*, Plaintiff-Appellee, *Sandoz, Inc*, Plaintiff-Appellee, v. *Amphastar Pharmaceuticals, Inc., International Medication Systems, Ltd., and Watson Pharmaceuticals, Inc.*, Defendants-Appellants. 2011 WL 7111556.
Brief in Opposition—*Momenta Pharmaceuticals, Inc.* v. *Amphastar Pharmaceuticals, Inc.* 2013 WL 2316705.
Brief of Plaintiffs—Appellees Momenta Pharmaceuticals, Inc. and Sandoz, Inc—*Momenta Pharmaceuticals, Inc.*, Plaintiff-Appellee, *Sandoz, Inc.*, Plaintiff-Appellee, v. *Amphastar Pharmaceuticals, Inc., International Medication Systems, Ltd., Watson Pharmaceuticals, Inc. and Watson Pharma, Inc.*, Defendants-Appellants. 2011 WL 7039087.
Complaint—*Momenta Pharmaceuticals, Inc. and Sandoz Inc.*, Plaintiffs, v. *Amphastar Pharmaceuticals, Inc., International Medication Systems, Ltd. and Watson Pharmaceuticals, Inc.*, Defendants. 2011 WL 4592253.
Complaint—*Momenta Pharmaceuticals, Inc. and Sandoz Inc.*, Plaintiffs, v. *Teva Pharmaceuticals Industries Ltd and Teva Pharmaceuticals USA, Inc.*, Defendants. 2010 WL 4888034.
Corrected Brief for Appellants—*Momenta Pharmaceuticals, Inc.*, Plaintiff-Appellee, *Sandoz, Inc.*, Plaintiff-Appellee, v. *Amphastar Pharmaceuticals, Inc., International Medication Systems, Ltd., and Watson Pharmaceuticals, Inc.*, Defendants-Appellants. 2011 WL 7111557.
Defendant Amphastar's Opening Claim Construction Brief—*Momenta Pharmaceuticals, Inc. and Sandoz, Inc.*, Plaintiffs, v. *Amphastar Pharmaceuticals, Inc., International Medication Systems, Ltd. and Watson Pharamceuticals, Inc.*, Defendants. 2012 WL 6150799.
Defendant Teva's Reply Claim Construction Brief—*Momenta Pharmaceuticals, Inc. and Sandoz, Inc.*, Plaintiffs, v. *Teva Pharmaceuticals USA, Inc.*, Defendant. 2012 WL 2455760.
Defendant's Preliminary Claim Construction Brief *Momenta Pharmaceuticals, Inc. and Sandoz, Inc.*, Plaintiffs, v. *Teva Pharmaceuticals USA, Inc.* Defendant. 2012 WL 2455754.
Defendants' Amended Answer to Plaintiffs' Amended Complaint—*Momenta Pharmaceuticals, Inc., et al.*, Plaintiffs, v. *Amphastar Pharmaceuticals, Inc., et al.*, Defendants. 2012 WL 6150795.
Defendants' Answer to Plaintiffs' Amended Complaint—*Momenta Pharmaceuticals, Inc., et al.*, Plaintiffs, v. *Amphastar Pharmaceuticals, Inc., et al.*, Defendants. 2012 WL 6150796.
*Momenta Pharmaceuticals, Inc. et al v. Teva Pharmaceuticals Industries Ltd. et al.*
*Momenta Pharmaceuticals, Inc. et al v. Amphastar Pharmaceuticals, Inc. et al.*
Mulloy et al., "The effect of variation of substitution on the solution conformation of heparin: a spectroscopic and milecular modeling study" Carbohydrate Research, vol. 255, pp. 1-26 (1994).
Plaintiffs' Answer to Defendants' Counterclaims—*Momenta Pharmaceuticals, Inc. and Sandoz, Inc.*, Plaintiffs, v. *Amphastar Pharmaceuticals, Inc., International Medication Systems, Ltd., Watson Pharmaceuticals, Inc., and Watson Pharma, Inc.*, Defendants. 2012 WL 4060946.

(56) References Cited

OTHER PUBLICATIONS

Plaintiffs' Claim Construction Memorandum U.S. Pat. No. 7,575,886 *Momenta Pharmaceuticals, Inc. and Sandoz Inc.*, Plaintiffs, v. *Teva Pharmaceuticals USA, Inc.*, Defendant. *Momenta Pharmaceuticals, Inc. and Sandoz Inc.*, Plaintiffs, v. *Amphastar Pharmaceuticals, Inc., International Medication Systems, Ltd., Watson Pharmaceuticals, Inc. and Watson Pharma, Inc.*, Defend 2012 WL 2455758.
Plaintiffs' Claim Construction Memorandum U.S. Pat. No. 7,575,886 *Momenta Pharmaceuticals, Inc. and Sandoz Inc.*, Plaintiffs, v. *Teva Pharmaceuticals USA, Inc.*, Defendant; *Momenta Pharmaceuticals, Inc. and Sandoz Inc.*, Plaintiffs, v. *Amphastar Pharmaceuticals, Inc., International Medication Systems, Ltd., Watson Pharmaceuticals, Inc. and Watson Pharma, Inc.*, Defend 2012 WL 6150688.
Plaintiffs' Claim Construction Memorandum U.S. Pat. No. 7,575,886 *Momenta Pharmaceuticals, Inc. and Sandoz Inc.*, Plaintiffs, v. *Teva Pharmaceuticals USA, Inc.*, Defendant; *Momenta Pharmaceuticals, Inc. and Sandoz Inc.*, Plaintiffs, v. *Amphastar Pharmaceuticals, Inc., International Medication Systems, Ltd., Watson Pharmaceuticals, Inc. and Watson Pharma, Inc.*, Defend 2012 WL 6150798.
Plaintiffs' Claim Construction Memorandum U.S. Pat. No. 7,790,466 *Momenta Pharmaceuticals, Inc. and Sandoz Inc.*, Plaintiffs, v. *Teva Pharmaceuticals USA, Inc.*, Defendant. *Momenta Pharmaceuticals, Inc. and Sandoz Inc.*, Plaintiffs, v. *Amphastar Pharmaceuticals, Inc., International Medication Systems, Ltd., Watson Pharmaceuticals, Inc. and Watson Pharma, Inc.*, Defend 2012 WL 2455750.
Plaintiffs' Claim Construction Memorandum U.S. Pat. No. 7,790,466 *Momenta Pharmaceuticals, Inc. and Sandoz Inc.*, Plaintiffs, v. *Teva Pharmaceuticals USA, Inc.*, Defendant; *Momenta Pharmaceuticals, Inc. and Sandoz Inc.*, Plaintiffs, v. *Amphastar Pharmaceuticals, Inc., International Medication Systems, Ltd., Watson Pharmaceuticals, Inc. and Watson Pharma, Inc.*, Defend 2012 WL 6150684.
Plaintiffs' Reply to the Defendants' Claim Construction Memoranda Regarding U.S. Pat. No. 7,790,466 *Momenta Pharmaceuticals, Inc. and Sandoz Inc.*, Plaintiffs, v. *Teva Pharmaceuticals USA, Inc.*, Defendant; *Momenta Pharmaceuticals, Inc. and Sandoz Inc.*, Plaintiffs, v. *Amphastar Pharmaceuticals, Inc., International Medication Systems, Ltd., Watson Pharmaceuticals, Inc. and Watson Pharma, Inc.*, Defend 2012 WL 6150797.
Reply Brief for Appeallants, *Momenta Pharmaceuticals, Inc.*, Plaintiff-Appellee, *Sandoz, Inc.*, Plaintiff-Appellee, v. *Amphastar Pharmaceuticals, Inc., International Medication Systems, Ltd., Watson Pharmaceuticals, Inc., and Watson Pharma, Inc.*, Defendants-Appellants. 2011 WL 7039088.
Reply Brief for Petitioners—*Momenta Pharmaceuticals, Inc.* v. *Amphastar Pharmaceuticals, Inc.* 2013 WL 2428972.
Turnbull et al., "Analytical and preparative strong anion-exchange HPLC of heparan sulfate and heparin saccharides" Methods in Molecular Biology, vol. 171, pp. 141-147 (2001).
International Search Report and Written Opinion from International Application Serial No. PCT/US11/21582 mailed Mar. 21, 2011.
International Search Report and Written Opinion from International Application Serial No. PCT/US2009/055792 mailed Feb. 12, 2009.
International Search Report from International Application Serial No. PCT/US03/07208 dated Nov. 16, 2004.
Jäger et al., "Simultaneous humoral and cellular immune response against cancer-testis antigen NY-ESO-1: definition of human histocompatibility leukocyte antigen (HLA)-A2-binding peptide epitopes", J. Exp. Med., 1998, vol. 187, pp. 265-270.
Kang et al., "Identification of a tyrosinase epitope recognized by HLA-A24-restricted, tumor-infiltrating lymphocytes", J. Immunol., 1995, vol. 155, pp. 1343-1348.
Kawakami et al., "Identification of a human melanoma antigen recognized by tumor-infiltrating lymphocytes associated with in vivo tumor rejection", Proc. Natl. Acad. Sci. USA, 1994, vol. 91, pp. 6458-6462.
Kawakami et al., "Identification of new melanoma epitopes on melanosomal proteins recognized by tumor infiltrating T lymphocytes restricted by HLA-A1, -A2, and -A3 alleles", J. Immunol., 1998, vol. 161, pp. 6985-6992.
Kawakami et al., "Identification of the immunodominant peptides of the MART-1 human melanoma antigen recognized by the majority of HLA-A2-restricted tumor infiltrating lymphocytes", J. Exp. Med., 1994, vol. 180, pp. 347-352.
Kawakami et al., "Recognition of multiple epitopes in the human melanoma antigen gp100 by tumor-infiltrating T lymphocytes associated with in vivo tumor regression", J. Immunol., 1995, vol. 154, pp. 3961-3968.
Kawashima et al., "The multi-epitope approach for immunotherapy for cancer: identification of several CTL epitopes from various tumor-associated antigens expressed on solid epithelial tumors", Hum. Immunol., 1998, vol. 59, pp. 1-14.
Keiser et al., "Preimplantation screening for transgenesis using an embryonic specific promoter and green fluorescent protein", Cloning, 2001, vol. 3, No. 1, pp. 21-30.
Kishimoto et al., "Contaminated heparin associated with adverse clinical events and activation of the contact system", The New England Journal of Medicine, Apr. 23, 2008, vol. 358, No. 23, pp. 2457-2467.
Kishimoto et al., "MII8—A rationally engineered low-molecular-weight heparin designed specifically for the treatment of acute coronary syndromes", Thrombosis and Haemostasis, 1999, vol. 102. No. 5. pp. 900-906.
Kittlesen et al., "Human melanoma patients recognize an HLA-A1-restricted CTL epitope from tyrosinase containing two cysteine residues: implications for tumor vaccine development", J. Immunol., 1998, vol. 160, pp. 2099-2106.
Kobayashi et al., "CD4+ T cells from peripheral blood of a melanoma patient recognize peptides derived from nonmutated tyrosinase", Cancer Research, 1998, vol. 58, pp. 296-301.
Langer "New methods of drug delivery", Science, 1990, vol. 249, pp. 1527-1533.
Larnkjaer et al., "Binding of Low Molecular Weight Heprin (Tinzaparin sodium) to Bovine Endothelial Cells in vitro" Thrombosis Res., vol. 75., No. 2, pp. 185-194 (1994).
Li et al., "Linkage analysis of chromophore-labeled disaccharides and linear oligosaccharides by negative ion fast atom bombardment ionization and collisonal-induced dissociation with B/E scanning", Analyt. Biochem., 1993, vol. 211, No. 2, pp. 250-257.
Lin et al., "Heparan sulfate proteoglycans are essential for FGF receptor signaling during Drosophila embryonic development", Development, 1999, vol. 126, pp. 3715-3723.
Lindahl et al., "Common binding sites for b-amyloid fibrils and fibroblast growth factor-2 in heparan sulfate from human cerebral cortex", J. Biol. Chem., 1999, vol. 274, pp. 30631-30635.
Liotta et al., "Cancer metastasis and angiogenesis: an imbalance of positive and negative regulation", Cell, 1991, vol. 64, pp. 327-336.
Liu et al., "A heparin-binding synthetic peptide of heparin/heparan sulfate-interacting protein modulates blood coagulation activities", PNAS, 1997, vol. 94, pp. 1739-1744.
Manici et al., "Melanoma cells present a MAGE-3 epitope to CD4(+) cytotoxic T cells in association with histocompatibility leukocyte antigen DR11", J. Exp. Med., 1999, vol. 189, pp. 871-876.
Parkhurst et al., "Identification of a shared HLA-A*0201-restricted T-cell epitope from the melanoma antigen tyrosinase-related protein 2 (TRP2)", Cancer Research, 1998, vol. 58, pp. 4895-4901.
Perlin et al., "Spectroscopic methods", The Polysaccharides, 1982, vol. 1, pp. 133-193, Edited by G.O., Academic Press.
Petitou et al., "Synthetic oligosaccharides having various functional domains: potent and potentially safe heparin mimetics", Bioorg. Med. Chem. Lett., 1999, vol. 9, No. 8, pp. 1161-1166.
Piani et al., "Alkali-induced optical rotation changes in heparins and heparan sulfates, and their relation to iduronic acid-containing sequences", Journal of Carbohydrate Chemistry, 1993, vol. 12, No. 4&5, pp. 507-521.
Pieper et al., "Biochemical identification of a mutated human melanoma antigen recognized by CD4(+) T cells", J. Exp. Med., 1999, vol. 189, pp. 757-765.

(56) References Cited

OTHER PUBLICATIONS

Pojasek, et al., "Histidine 295 and histidine 510 are crucial for the enzymatic degradation of heparan sulfate by heparinase III", Biochemistry, 2000, vol. 39, pp. 4012-4019.

Rhomburg et al., "Mass spectrometric evidence for the enzymatic mechanism of the depolymerization of heparin-like like glycosaminoglycans by heparinase II", PNAS USA, 1998, vol. 95, pp. 12232-12237.

Rice et al., "Gradient page and strong anion exchange Sax Hplc as analytical tools for sequencing the heparin polymer", American Chemical Society, 1987, vol. 193, pp. 1, Abstracts of paper from the National Meeting.

Robbins et al., "A mutated b-catenin gene encodes a melanoma-specific antigen recognized by tumor infiltrating lymphocytes", J. Exp. Med., 1996, vol. 183, pp. 1185-1192.

Robbins et al., "The intronic region of an incompletely spliced gp100 gene transcript encodes an epitope recognized by melanoma-reactive tumor-infiltrating lymphocytes", J. Immunol., 1997, vol. 159, pp. 303-308.

Ronsin et al., "A non-AUG-defined alternative open reading frame of the intestinal carboxyl esterase mRNA generates an epitope recognized by renal cell carcinoma-reactive tumor-infiltrating lymphocytes in situ", J. Immunol., 1999, vol. 163, pp. 483-490.

Röpke et al., "Spontaneous human squamous cell carcinomas are killed by a human cytotoxic T lymphocyte clone recognizing a wild-type p53-derived peptide", Proc. Natl. Acad. Sci. USA, 1996, vol. 93, pp. 14704-14707.

Sasisekharan et al. "Heparinase inhibits neovascularization", Proc. Natl. Acad. Sci. USA, 1994, vol. 91, pp. 1524-1528.

Schanda, "Very fast two-dimensional NMR spectroscopy for real-time investigation of dynamic events in proteins on the time scale of seconds", Journal of the American Chemical Society, 2005, vol. 127, pp. 8014-8015.

Schneider et al., "Overlapping peptides of melanocyte differentiation antigen Melan-A/MART-1 recognized by autologous cytolytic T lymphocytes in association with HLA-B45.1 and HLA-A2.1", Int. J. Cancer, 1998, vol. 75, pp. 451-458.

Shriver et al., "Sequencing of 3-0 sulfate containing heparin decasaccharides with a partial antithrombin III binding site", PNAS, 2000, vol. 97, No. 19, pp. 10359-10364.

U.S. Appl. No. 12/150,899, filed Apr. 30, 2008, Shriver et al., Abandoned.

U.S. Appl. No. 11/455,945, filed Jun. 20, 2006, Shriver et al., Pending.

U.S. Appl. No. 11/426,765, filed Jun. 27, 2006, Shriver et al., Pending.

Beccati D et al. "Identification of a novel structure in heparin generated by potassium permanganate oxidation", Carbohydrate Polymers, Applied Science Publishers, Ltd. Barking, GB, vol. 82, No. 3, Oct. 15, 2010, pp. 699-705.

Beyer T et al. "Quality assessment of unfractionated heparin using <1>H nuclear magnetic resonance spectroscopy"Journal of Pharmaceutical and Biomedical Analysis. New York, NY, US. vol. 48, No. 1, Sep. 10, 2008, pp. 13-19.

Bigler P et al. "Improved impurity fingerprinting of heparin by high resolution <1>H NMR spectroscopy", Journal of Pharmaceutical and Biomedical Analysis, New York, NY, US, vol. 49, No. 4, May 1, 2009, pp. 1060-1064.

Extended European Search Report for Application No. 11735052.0 dated Mar. 18, 2015.

Guerrini M et al. "Oversulfated chondroitin sulfate is a contaminant in heparin associated with adverse clinical events", Nature Biotechnology, Nature Publishing Group, New York, NY, US, vol. 26., No. 6., Apr. 23, 2008, pp. 669-675.

International Preliminary Report on Patentability and Written Opinion for International Application Serial No. PCT/US2012/025920 issued Aug. 21, 2013.

International Search Report and Written Opinion from International Application Serial No. PCT/US2009/035687 mailed Apr. 14, 2009.

International Search Report from International Application Serial No. PCT/US2012/025920 dated May 30, 2012.

Kellenbach E et al. "H NMR signal at 2.10A ppm in the spectrum of KMnO-bleached heparin sodium: identification of the chemical origin using an NMR-only approach", Analytical and Bioanalytical Chemistry, Springer, Berlin, DE, vol. 399, No. 2, Nov. 11, 2010, pp. 621-628.

Markham et al., "The Mis-identification of the Major Antioxidant Flavonoids in Young Barley (*Hordeum vulgare*) Leaves" Zeitschrift fur Naturforschung C. A journal of biosciences, 58C:53-56 (2003).

Moon et al., "Complete Assignments of the 1H and 13C NMR Data of Flavone Derivatives" Bulletin of the Korean Chemical Society, 26(4):603-608 (2005).

Neville G A et al. "Monitoring the Purity of Pharmaceutical heparin preparations by high-field 1H-nuclear magnetic resonance spectroscopy.", Journal of Pharmaceutical Sciences, vol. 78, No. 2, Feb. 1989, pp. 101-104.

Trehy M L et al. "Analysis of heparin sodium by SAX/HPLC for contaminants and impurities", Journal of Pharmaceutical and Biomedical Analysis, New York, NY, US, vol. 49, No. 3, Apr. 5, 2009, pp. 670-673.

Liu et al., "Strategy for the sequence analysis of heparin", Glycobiology, 1995, vol. 5, pp. 765-774.

Lupetti et al., "Translation of a retained intron in tyrosinase-related protein (TRP) 2 mRNA generates a new cytotoxic T lymphocyte (CTL)-defined and shared human melanoma antigen not expressed in normal cells of the melanocytic lineage", J. Exp. Med., 1998, vol. 188, pp. 1005-1016.

Mandruzzato et al., "A CASP-8 mutation recognized by cytolytic T lymphocytes on a human head and neck carcinoma", J. Exp. Med., 1997, vol. 186, pp. 785-793.

Manici at al., "Melanoma cells present a MAGE-3 epitope to CD4(+) cytotoxic T cells in association with histocompatibility leukocyte antigen DR11", J. Exp. Med., 1999, vol. 189, pp. 871-876.

Mauray et al., "Mechanism of factor IXa inhibition by antithrombin in the presence of unfractionated and low molecular weight heparins and fucoidan", Biochim. Biophys. Acta, vol. 1387, No. 1-2, pp. 184-194, (1998).

McLaurin et al., "Interactions of Alzheimer amyloid-b peptides with glycosaminoglycans effects on fibril nucleation and growth", Eur. J. Biochem., 1999, vol. 266, pp. 1101-1110.

Merry et al., "Highly sensitive sequencing of the sulfated domains of heparan sulfate", J. Biol. Chem., 1999, vol. 274, pp. 18455-18462.

Morel et al., "A tyrosinase peptide presented by HLA-B35 is recognized on a human melanoma by autologous cytotoxic T lymphocytes", Int. J. Cancer, 1999, vol. 83, pp. 755-759.

Morell et al., "Analysis of starch structure using fluorophore-assisted carbohydrate electrophoresis", Electrophoresis, 1998, vol. 19, No. 15, pp. 2603-2611.

Oiso et al., "A newly identified MAGE-3-derived epitope recognized by HLA-A24-restricted cytotoxic T lymphocytes", Int. J. Cancer, 1999, vol. 81, pp. 387-394.

Parish et al., "A basement-membrane permeability assay which correlates with the metastatic potential of tumour cells", Int. J. Cancer, 1992, vol. 52, pp. 378-383.

\* cited by examiner

METHOD OF ANALYZING A PREPARATION OF A LOW MOLECULAR WEIGHT HEPARIN

CROSS-REFERENCE TO RELATED APPLICATIONS

This application claims priority to U.S. Provisional Application Ser. No. 60/915,791, filed on May 3, 2007, the contents of which is incorporated by reference in its entirety.

TECHNICAL FIELD

The invention relates to methods of analyzing samples containing complex carbohydrates, e.g., unfractionated heparin (UFH) and low molecular weight heparins (LMWHs), most preferably enoxaparin. In particular, it relates to methods which use reverse phase high performance liquid chromatography (RPHPLC) or strong anion exchange chromatography (SAX-HPLC), e.g., to analyze, control or monitor the production of a LMWH such as enoxaparin. This method can be employed at the on drug product or drug substance to establish structural attributes and compare to a reference standard, or, alternatively, it can be employed to analyze starting material (i.e. UFH) to preselect batches of material for production of drug product or drug substance. It also relates to useful analytes and compositions which can be detected or prepared with the methods described herein.

BACKGROUND

Complex polysaccharides have been used as pharmaceutical interventions in a number of disease processes, including oncology, inflammatory diseases, and thrombosis. Examples of pharmaceutical interventions in this class are hyaluronic acid, an aid to wound healing and anti-cancer agent, and heparin, a potent anticoagulant and anti-thrombotic agent. Complex polysaccharides elicit their function primarily through binding soluble protein signaling molecules, including growth factors, cytokines and morphogens present at the cell surface and within the extracellular matrices between cells, as well as their cognate receptors present within this environment. In so doing, these complex polysaccharides effect critical changes in extracellular and intracellular signaling pathways important to cell and tissue function. For example, heparin binds to the coagulation inhibitor antithrombin III, thus promoting its ability to inhibit factor IIa and Xa. Being able to identify and quantify the type and extent of chemical modification of a polysaccharide chain as a result of isolation and processing would be of benefit both from (1) a process control standpoint and (2) understanding biologically specific structure-function relationships.

SUMMARY

The analysis of LMWHs, e.g., enoxaparin, e.g., by RPHPLC or SAX-HPLC, can be used to evaluate starting materials, processes, intermediates and final products in the production of low molecular weight heparins (LMWHs), particularly enoxaparin. The presence, distribution, or amount of a structure or species, described herein can be used in these evaluations.

By way of example, RPHPLC analysis of a digested enoxaparin sample can resolve a species described in Table IA. It also provides the amount of the species in the treated sample. Accordingly, a preparation can be evaluated by determining the presence, distribution or amount of one or more of the species in Table IB.

By way of further example, RPHPLC analysis of a digested unfractionated heparin (UFH) sample can resolve the species described in Table IA, e.g., to evaluate UFH as a starting material to produce a LMWH, e.g., enoxaparin. It also provides the amount of the species in the treated sample. Thus, a preparation can be evaluated by determining the presence distribution or amount of one or more species in Table IC. Although the species in Table IA are derived from enoxaparin and/or UFH, some, e.g., structures associated with peaks 1, 2, 3, 4, 5, 6, 9, 10, 11, 12, 13, 14, 15, 16, 17, 18, 21, 22, 24, 25, 27, 28, 29, 32, 33, 35, 37, and 38 (and identified in Table IA) will occur in other LMWHs, e.g., LMWHs derived from UFH, and can be used in the evaluation of LMWHs.

Methods of analysis described herein can be combined allowing, e.g., characterization of a sample by evaluation of a subject species in Table IA in a LMWH preparation, e.g., an enoxaparin preparation, e.g., in an amount of a subject species in Table IB, and starting material, e.g., unfractionated heparin, in an amount of a subject species in Table IC or Table ID.

Methods disclosed herein are useful for analyzing or processing a LMWH preparation, e.g., to determine whether to accept or reject a batch of a LMWH, e.g., enoxaparin, or to guide the control of a step in the production of a LMWH, e.g., enoxaparin.

The methods described herein can be used for LMWHs, and in particular enoxaparin. Enoxaparin is the preferred LMWH and the examples and much of the discussion is directed to enoxaparin. The methods described herein can, though, be applied to other LMWHs. In some cases, the methods are directly applicable and someone of the ordinary skill in the art will appreciate that modifications may be needed and can institute those as guided by the art and this disclosure.

In one aspect, the invention provides a method of evaluating or processing a polysaccharide mixture, e.g., a LMWH, e.g., an enoxaparin preparation.

The method includes:
providing an evaluation of a parameter related to a subject entity, e.g., a structure or specie or species, e.g., a chain, described herein, e.g., a subject entity listed in Table IA. Such parameters can include the presence, relative distribution, or amount of a subject entity, e.g., a structure and/or chain disclosed herein, and, optionally, providing a determination of whether a value (e.g., a value correlated to absence or presence) determined for the parameter meets a preselected criteria, e.g., is present or present in a preselected range, thereby evaluating or processing the mixture.

In a preferred embodiment, the method includes providing a comparison of the value determined for a parameter with a reference value or values, to thereby evaluate the sample. In preferred embodiments, the comparison includes determining if the test value has a preselected relationship with the reference value, e.g., determining if it meets the reference value. The value need not be a numerical value but can be merely an indication of whether the subject entity is present.

In a preferred embodiment, the method includes determining if a test value is equal to or greater than a reference value, if it is less than or equal to a reference value, or if it falls with a range (either inclusive or exclusive of the endpoints of the range). By way of example, the method can include determining if the amount of a species listed in Table IA is present in a range for that species, e.g., range A, B, C, D, or E provided for that species in Table IB. By way of further example, the method can include determining if the amount of species listed in Table IA is present in a range for that species, e.g., range A, B, C, D or E provided for that species in Table IC or Table ID. In one embodiment, the amount of a specie or species can be determined using a non-uniform factor.

In preferred embodiments, the test value, or an indication of whether the preselected relationship is met, can be memorialized, e.g., in a computer readable record.

In preferred embodiments, a decision or step is taken, e.g., the sample is classified, selected, accepted or discarded, released or withheld, processed into a drug product, shipped, moved to a new location, formulated, labeled, packaged, released into commerce, sold, or offered for sale, depending on whether the preselected criterion is met. For example, based on the result of the determination of whether one or more subject entity is present, or upon comparison to a reference standard, the batch from which the sample is taken can be processed, e.g., as just described.

As mentioned above, the methods disclosed herein can include evaluating the presence, distribution, or amount, of a selected subject entity, e.g., a structure or species, e.g., a selected chain in a sample. Examples of a species, sometimes referred to herein as a chain, include di-, tri-, tetra-, saccharides. A structure can be, e.g., a particular residue, or group of residues, e.g., a disaccharide pair, existing within a chain or as a discrete disaccharide molecule. Other examples of structures include selected inter-saccharide linkages, terminal groups, epimeric structures, the presence or location of a derivative moiety, e.g., a sulfate or an acetyl group, or a mannosamine, or an anhydro structure.

A particularly preferred structure, e.g., with regard to structures in Table IA is a sulfate group, an acetyl group, an anhydro structure, a mannosamine or hexosamine, a glucuronic, galacturonic or iduronic acid, an $\alpha$ or $\beta$ isomer and combinations thereof. A particularly preferred species is a disaccharide, trisaccharide and/or tetrasaccharide, e.g., a disaccharide, trisaccharide, tetrasaccharide that includes 0, 1, 2, 3, 4, 5 or 6 sulfate groups and/or 0 or 1 acetyl groups, an anhydro structure, a galacturonic acid, glucuronic acid or iduronic acid, a mannosamine or a hexosamine and/or an $\alpha$ or $\beta$ isomer.

The evaluation of the presence, distribution or concentration of a subject entity, e.g., a structure or specie or species can show if the subject entity or a LMWH preparation, e.g., an enoxaparin preparation, or starting material for a LMWH preparation, e.g., an unfractionated heparin preparation, meets a reference standard.

In preferred embodiments, methods and compositions disclosed herein are useful from a process standpoint, e.g., to monitor or ensure batch-to-batch consistency or quality, or to evaluate a sample with regard to a reference, e.g., a preselected value.

In preferred embodiments, methods and compositions disclosed herein can be used to determine if a test batch of a LMWH, e.g., enoxaparin, can be expected to have one or more properties of the LMWH, e.g., enoxaparin. Such properties can include a property listed on the product insert of the LMWH, e.g., enoxaparin, a property appearing in a compendium, e.g., the U.S. Pharmacopeia, or a property required by a regulatory agency, e.g., the U.S. Food and Drug Administration (the FDA), for commercial use. A determination made by a method disclosed herein can be a direct or indirect measure of such property. For example, a direct measurement can be where the desired property is a preselected level of the subject entity being measured. In an indirect measurement, the measured subject entity is correlated with a desired property, e.g., a property described herein.

Exemplary properties include:

A preselected level of anti-XA activity, e.g., between 75-150 IU/mg and preferably about 100 IU/mg;

A preselected level of anti-IIA activity, e.g., between 20-35 and preferably about 30 IU/mg;

A preselected ratio of anti-XA/anti-IIA activity, e.g., between 3.3-5.3 and preferably about 4;

A preselected value for average molecular weight, e.g., between 4300-4800 Da and preferably about 4500 Da;

A set of preselected value for molecular weight distribution, e.g., about 12-20% and preferably 16% are <2000 Da species, greater than or equal to 68-82% and preferably greater than or equal to 68% are 2000-8000 Da species; and less than or equal to 18% are >8000 Da species;

A preselected level of chains ending in a 1,6-anhydro linkage, e.g., between 15-30% and preferably about 15-25% or 20-30%, e.g., as measured by weight average molecular weight or total % of chain;

A preselected value for the linkage region form, from 0.3-1.7 area %.

Methods and compositions disclosed herein can be used where the presence, distribution, or amount, of one or more structure or species in the mixture may possess or impinge on the biological activity. The methods are also useful from a structure-activity prospective, to evaluate or ensure biological equivalence.

In a preferred embodiment, the sample is analyzed by high performance liquid chromatography, e.g., RPHPLC or SAX-HPLC. In a preferred embodiment, the evaluation is performed on a sample which has been digested, e.g., with heparin cleaving enzymes. In a preferred embodiment, the method includes providing a digested enoxaparin preparation or a digested UFH preparation and subjecting the preparation to analysis, e.g., with RPHPLC or SAX-HPLC; and optionally, evaluating the presence, distribution, or amount, of a selected subject entity, e.g., a structure or species, in a sample.

In a preferred embodiment, a saccharide structure and/or chain is evaluated using, e.g., RPHPLC or SAX-HPLC, e.g., RPHPLC or SAX-HPLC carried out in a mobile phase under one or more of the following conditions: a mobile phase which is transparent to UV light with wavelengths of about 200 nm to about 400 nm; a mobile phase that comprises at least one salt (e.g., an ion-pairing agent) described herein; and a mobile phase that includes a sodium chloride solution maintained at pH 3.5, 5.5, or 7.0. Preferred salts are ammonium and phosphonium salts.

In one embodiment, prior to RPHPLC analysis, the preparation is digested with one or more heparin degrading enzyme, e.g., one or more heparin degrading enzyme described herein. In one embodiment, the enoxaparin preparation is digested with heparinase I, heparinase II and heparinase III, e.g., *Flavobacterium heparinum* heparinase I, heparinase II and heparinase III. In other embodiments, the LMWH preparation is digested with heparinase I, heparinase II, heparinase III, and 2-O sulfatase and/or with heparinase I, heparinase II, heparinase III, 2-O sulfatase and $\Delta^{4,5}$ glycuronidase. In one embodiment, the heparin preparation is digested with *Bacteroides thetaiotaomicron* HSGAG lyase I, HSGAG lyase II, HSGAG lyase III (and optionally, GAG lyase IV). In other embodiments, the heparin preparation is digested with HSGAG lyase I, HSGAG lyase II, HSGAG lyase III, (optionally GAG lyase IV) and 2-O sulfatase and/or with HSGAG lyase I, HSGAG lyase II, HSGAG lyase III, (optionally GAG lyase IV), 2-O sulfatase and $\Delta^{4,5}$ glycuronidase.

In one embodiment, digestion can be performed either by (I) addition of heparinase I-III then addition of either $\Delta^{4,5}$ glycuronidase followed by 2-O sulfatase or 2-O sulfatase then $\Delta^{4,5}$ glycuronidase; or (2) pretreatment of the preparation with either $\Delta^{4,5}$ glycuronidase and 2-O sulfatase or $\Delta^{4,5}$ glycuronidase followed by digestion with heparinases I-III. In another embodiment, digestion can be performed either by (I) addition of HSGAG lyase I-III then addition of either $\Delta^{4,5}$ glycuronidase followed by 2-O sulfatase or 2-O sulfatase then $\Delta^{4,5}$ glycuronidase; or (2) pretreatment of the preparation with either $\Delta^{4,5}$ glycuronidase and 2-O sulfatase or $\Delta^{4,5}$ glycuronidase followed by digestion with HSGAG lyase I-III. In another embodiment, various combinations of heparinase(s) and HSGAG lyase(s) can be used in the digestion.

In a preferred embodiment, the digestion is run to completion or at least sufficiently to provide a digest having all of the products found in Table IB (for enoxaparin preparations) or Table IC (for unfractionated heparin preparations) and preferably substantially free of undigested material.

In one embodiment, the digested preparation includes one or more monosaccharide, one or more disaccharide, one or more trisaccharide, one or more tetrasaccharide, and combinations of these size classes. In one embodiment, the preparation is completely digested, and the polysaccharides in the digested preparation are present as one or more monosaccharide, one or more disaccharide, one or more trisaccharide, one or more tetrasaccharide and combinations of these size classes.

In one embodiment, the method includes identifying and/or quantifying the amount or size distribution of one or more structural moiety in the preparation. The quantity of the structural moiety can be compared to, e.g., normalized relative to, a second structural moiety, such as $\Delta U_{2S}$. In one embodiment, the preparation can be unfractionated heparin or an enoxaparin preparation can be evaluated for a structural moiety naturally associated with a starting material, e.g., unfractionated heparin. The structural moiety can be due to isomerization, e.g., it can be an $\alpha$ or $\beta$ anomer of a particular structural moiety. In one embodiment, the structure can be associated with one or more of peaks 1, 2, 3, 4, 5, 6, 9, 10, 11, 12, 13, 14, 15, 16, 17, 18, 21, 22, 24, 25, 27, 28, 29, 32, 33, 35, 37, and 38 of FIG. 1 and FIG. 2 (and identified in Table IA). In another embodiment, the preparation is an enoxaparin preparation and the structural moiety can be a structure not naturally associated with a starting material, e.g., unfractionated heparin. For example, a structure not naturally associated with the starting material (also referred to herein as a "modified structural moiety") can be, e.g., a structure resulting from a method used to make the enoxaparin sample. In one embodiment, the preparation is an enoxaparin preparation and the modified structural moiety can be one or more of: a mannosamine, a trisaccharide (e.g., a trisaccharide resulting from chemical peeling), a 1,6 anhydro linkage, and a uronic acid at the reducing end. In one embodiment, the structure can be associated with one or more of peaks 4, 7, 8, 19, 20, 23, 26, 30, 31, 34 and 36 of FIG. 1 (and identified in Table IA). In one embodiment, the structural moiety can be further characterized using, e.g., mass spectrometry, e.g., ESI-MS, and/or NMR.

The method can include determining the amount or the size distribution of one or more structural moiety, e.g., using a non-uniform factor.

In one embodiment, the preparation includes one or more of the following compounds:

TABLE IA

| Peak # | Identity | Comment on building blocks |
|---|---|---|
| 1 | $\Delta UH_{NAc}$ | Natural |
| 2 | Linkage region isomer | Natural |
| 3 | $\Delta UGalGalXyl$-O—$CH_2$—COOH | Natural |
| 4 | $\Delta U_{gal}H_{NS}$ | Modified |
| 5 | $\Delta UH_{NS}$ ($\alpha$) | Natural |
| 6 | $\Delta UH_{NS}$ ($\beta$) | Natural |
| 7 | $\Delta UH_{NS}$ (1,6 anhydro) | Modified |
| 8 | $\Delta UMan_{NS}$ (1,6 anhydro) | Modified |
| 9 | $\Delta UH_{NAc6S}$ | Natural |
| 10 | $\Delta U_{2S}H_{NAc}$ ($\alpha$) | Natural |
| 11 | $\Delta U_{2S}H_{NAc}$ ($\beta$) | Natural |
| 12 | $\Delta UH_{NS3S}$ | Natural |
| 13 | $\Delta UH_{NS6S}$ ($\alpha$) | Natural |
| 14 | $\Delta U_{gal}H_{NS6S}$ ($\alpha$) | Modified |
| 15 | $\Delta U_{gal}H_{NS6S}$ ($\beta$) | Modified |
| 16 | $\Delta UH_{NS6S}$ ($\beta$) | Natural |
| 17 | $\Delta U_{2S}H_{NS}$ ($\alpha$) | Natural |
| 18 | $\Delta U_{2S}H_{NS}$ (($\beta$) | Natural |
| 19 | $\Delta U_{2S}H_{NS}$ (1,6 anhydro) | Modified |
| 20 | $\Delta U_{2S}Man_{NS}$ (1,6 anhydro) | Modified |
| 21 | $\Delta U_{2S}H_{NAc6S}$ ($\alpha$) | Natural |
| 22 | $\Delta U_{2S}H_{NAc6S}$ ($\beta$) | Natural |
| 23 | $\Delta U_{2S}Man_{NAc,6S}$ | Modified |
| 24 | $\Delta UHN_{Ac6S}GH_{NS,3S}$ ($\alpha$) | Natural |
| 25 | $\Delta UHN_{Ac6S}GH_{NS,3S}$ ($\beta$) | Natural |
| 26 | $\Delta U_{2S}Man_{NS6S}$ ($\alpha$) | Modified |
| 27 | $\Delta U_{2S}H_{NS6S}$ ($\alpha$) | Natural |
| 28 | $\Delta UH_{NAc6S}GH_{NS,3S,6S}$ ($\alpha$) | Natural |
| 29 | $\Delta U_{2S}H_{NS6S}$ ($\beta$) | Natural |
| 30 | $\Delta U_{2S}H_{NS6S}I_{2S}$ ($\alpha$) | Modified |
| 31 | $\Delta U_{2S}H_{NS6S}I_{2S}$ ($\beta$) | Modified |
| 32 | $\Delta UH_{NS6S}GH_{NS3S6S}$ ($\alpha$) | Natural |
| 33 | $\Delta UH_{NS6S}GH_{NS3S6S}$ ($\beta$) | Natural |
| 34 | $\Delta U_{2S}H_{NS6S}I_{2S}H_{NS}$ (1,6 anhydro) | Modified |
| 35 | $\Delta U_{2S}H_{NS3S6S}$ | Natural |
| 36 | $\Delta U_{2S}H_{NS6S}I_{2S}Man_{NS}$ (1,6 anhydro) | Modified |
| 37 | $\Delta U_{2S}H_{NS6S}GH_{NS3S6S}$ ($\beta$) | Natural |
| 38 | $\Delta U_{2S}H_{NS6S}GH_{NS3S6S}$ ($\alpha$) | Natural |

The structures in this Table are determined using RPHPLC or SAX-HPLC, and when necessary, by other analytical methods, e.g., using ESI-MS and NMR to analyze one or more structure. The combination of data allows determination of the structures in Table IA.

In a preferred embodiment, the method includes evaluating a subject entity to determine the amount of that subject entity present in the sample. The amount can be evaluated in any way, e.g., in absolute terms, e.g., in milligrams, or the level of subject entity can be related to one or more or all other species in the sample. The amount can be expressed, e.g., in terms of mole %, % of chains, weight % or % area under the curve (AUC). In some embodiments, the amount for a subject entity is determined and then evaluated to determine if it is present in a preselected amount or range, e.g., an amount or range disclosed herein, e.g., in Table IB, Table IC or Table ID. This can be done by comparing with a range of reference values for that subject entity. For example, an amount for one or more or all of the building blocks evaluated, e.g., for presence, or to determine if the subject entity is present in a range indicated in Table IB, Table IC or Table ID. In one embodiment, the amount of the subject entity can be determined using a non-uniform factor.

In one embodiment, the preparation is a LMWH preparation, e.g., an enoxaparin preparation, and a percentage of the structural moieties, e.g., the total percentage of chains having the structural moieties, in the preparation have been determined, e.g., by mole %, and preferably the method includes determining or confirming that the moiety is in that range. In one embodiment, the range for the structural moiety is one or more of the following:

TABLE IB

Preferred Ranges of Structural Entities in Enoxaparin

| Building B | Range A | | Range B | | Range C | |
|---|---|---|---|---|---|---|
| P-1 | 1.1 | 2.4 | 1.4 | 2.7 | 1.1 | 3.4 |
| P-2 | 0.0 | 0.4 | 0 | 0.4 | NMT 1 | |
| P-3 | 0.4 | 4.7 | 1.2 | 3.6 | 0.9 | 4.5 |
| P-4 | 0.0 | 0.7 | 0.2 | 0.8 | P | NMT 1 |
| P-5 | 1.6 | 2.0 | 1.6 | 1.9 | 1.2 | 2.4 |
| P-6 | 0.3 | 0.4 | 0.3 | 0.4 | P | NMT 1 |
| P-7 | 0.2 | 0.3 | 0.2 | 0.3 | P | NMT 1 |
| P-8 | 0.3 | 0.5 | 0.3 | 0.5 | P | NMT 1 |
| P-9 | 3.1 | 4.2 | 3.4 | 4.4 | 2.6 | 5.5 |
| P-10 | 0.4 | 0.9 | 0.4 | 0.8 | P | NMT 1 |
| P-11 | 1.0 | 1.5 | 1.1 | 1.4 | 0.8 | 1.8 |
| P-12 | 0.0 | 0.5 | 0 | 0.4 | NMT 1 | |
| P-13 + P14 | 7.4 | 10.6 | 7.4 | 10.5 | 5.6 | 13.1 |
| P-15 + P16 | 0.6 | 1.1 | 0.7 | 1.1 | 0.5 | 1.4 |
| P-17 | 5.4 | 6.4 | 5.6 | 6.2 | 4.2 | 7.8 |
| P-18 | 0.6 | 1.2 | 0.7 | 1.2 | 0.5 | 1.5 |
| P-19 | 1.4 | 1.7 | 1.5 | 1.7 | 1.1 | 2.1 |
| P-20 | 0.0 | 0.3 | 0.1 | 0.3 | P | NMT 1 |
| P-21 | 0.4 | 0.7 | 0.4 | 0.6 | P | NMT 1 |
| P-22 | 0.8 | 1.1 | 0.9 | 1.1 | 0.7 | 1.4 |
| P-23 | 0.0 | 0.2 | 0 | 0.2 | NMT 1 | |
| P-24 | 0.5 | 1.1 | 0.4 | 0.9 | P | NMT 1 |
| P-25 | 0.1 | 0.3 | 0.1 | 0.3 | P | NMT 1 |
| P-26 | 1.5 | 2.5 | 1.3 | 2.2 | 1 | 2.8 |
| P-27 | 43.4 | 47.4 | 44.4 | 46.7 | 40 | 51.4 |
| P-28 | 2.1 | 4.5 | 2 | 4.2 | 1.5 | 5.3 |
| P-29 | 4.5 | 6.7 | 5.1 | 6.3 | 3.8 | 7.9 |
| P-30 | 0.5 | 1.0 | 0.5 | 0.9 | P | NMT 1 |
| P-31 | 0.9 | 1.6 | 1.1 | 1.7 | 0.8 | 2.1 |
| P-32 | 0.2 | 0.9 | 0.1 | 0.9 | P | NMT 1 |
| P-33 | 0.1 | 0.7 | 0.2 | 0.7 | P | NMT 1 |
| P-34 | 0.0 | 0.6 | 0 | 0.5 | NMT 1 | |
| P-35 | 0.1 | 0.4 | 0.1 | 0.3 | P | NMT 1 |
| P-36 | 4.5 | 5.7 | 4.6 | 5.4 | 3.5 | 6.8 |
| P-37 | 0.2 | 0.6 | 0.3 | 0.5 | P | NMT 1 |
| P-38 | 0.4 | 0.7 | 0.4 | 0.7 | P | NMT 1 |

TABLE IC

Preferred Ranges of Structural Entities in Unfractionated Heparin

| Building Block* | Range A | | Range B | | Range C | | Range D | | Range E | |
|---|---|---|---|---|---|---|---|---|---|---|
| 1 | 2.0 | 6.0 | 3.5 | 5.5 | 4.0 | 6.5 | 3.0 | 4.5 | 3.8 | 4.3 |
| 2 | 0.00 | 0.5 | 0.00 | 0.00 | 0.00 | 0.05 | 0.00 | 0.1 | ≤0.2 | |
| 3 | 0.2 | 1.0 | 0.3 | 1.4 | 0.5 | 2.0 | 0.1 | 0.8 | 0.3 | 1.8 |
| 4 | 0.2 | 1.0 | 0.2 | 0.6 | 0.1 | 0.4 | 0.2 | 0.4 | 0.1 | 0.8 |
| 5 | 1.0 | 3.0 | 0.8 | 1.5 | 1.2 | 1.4 | 1.0 | 1.5 | 0.5 | 3.5 |
| 6 | 0.1 | 0.6 | 0.05 | 0.5 | 0.05 | 0.3 | 0.05 | 0.7 | 0.1 | 0.3 |
| 7 | 0.00 | 0.5 | 0.00 | 0.00 | 0.00 | 0.05 | 0.00 | 0.1 | ≤0.2 | |
| 8 | 0.00 | 0.5 | 0.00 | 0.00 | 0.00 | 0.05 | 0.00 | 0.1 | ≤0.2 | |
| 9 | 4.0 | 6.0 | 4.8 | 6.2 | 4.2 | 5.5 | 4.6 | 5.2 | 4.2 | 5.8 |
| 10 | 0.3 | 0.8 | 0.2 | 0.8 | 0.6 | 1.2 | 0.2 | 0.9 | 0.4 | 0.9 |
| 11 | 0.9 | 1.4 | 0.6 | 1.3 | 1.0 | 1.5 | 0.5 | 1.7 | 0.8 | 1.7 |
| 12 | 0.05 | 0.3 | 0.00 | 0.3 | 0.05 | 0.5 | 0.00 | 0.3 | ≤0.5 | |
| 13 | 9.0 | 11.0 | 9.8 | 12.2 | 8.8 | 10.2 | 10.0 | 10.3 | 9.5 | 11.5 |
| 14 | 1.0 | 3.0 | 2.0 | 4.0 | 2.0 | 5.0 | 1.0 | 2.8 | 2.0 | 2.5 |
| 15 | 0.1 | 0.5 | 0.2 | 0.6 | 0.1 | 0.4 | 0.2 | 0.4 | 0.05 | 1.0 |
| 16 | 0.00 | 2.0 | 0.5 | 1.5 | 0.8 | 1.5 | 0.5 | 1.2 | 0.8 | 1.2 |
| 17 | 3.1 | 7.3 | 5.1 | 6.2 | 3.6 | 8.5 | 5.8 | 8.5 | 4.2 | 6.4 |
| 18 | 0.4 | 1.0 | 0.7 | 1.0 | 0.5 | 1.2 | 0.4 | 1.3 | 0.6 | 1.3 |
| 19 | 0.00 | 0.5 | 0.00 | 0.00 | 0.00 | 0.05 | 0.00 | 0.1 | ≤0.2 | |
| 20 | 0.00 | 0.5 | 0.00 | 0.00 | 0.00 | 0.05 | 0.00 | 0.1 | ≤0.2 | |
| 21 | 0.4 | 0.8 | 0.1 | 1.0 | 0.5 | 1.2 | 0.4 | 0.9 | 0.4 | 1.0 |
| 22 | 0.9 | 1.2 | 0.8 | 1.7 | 0.6 | 1.4 | 0.6 | 1.2 | 0.8 | 1.5 |
| 23 | 0.00 | 0.5 | 0.00 | 0.00 | 0.00 | 0.05 | 0.00 | 0.1 | ≤0.2 | |
| 24 | 0.8 | 1.4 | 0.2 | 2.0 | 1.0 | 2.5 | 0.05 | 1.2 | 0.5 | 1.5 |
| 25 | 0.00 | 0.5 | 0.00 | 0.00 | 0.00 | 0.05 | 0.00 | 0.1 | ≤0.2 | |
| 26 | 0.00 | 0.5 | 0.00 | 0.00 | 0.00 | 0.05 | 0.00 | 0.1 | ≤0.2 | |
| 27 | 50 | 53 | 50.5 | 60.5 | 48 | 55 | 45 | 55 | 46 | 52 |
| 28 | 2.0 | 6.0 | 1.7 | 4.3 | 3.8 | 6.1 | 3.5 | 4.8 | 3.5 | 5.0 |
| 29 | 5.5 | 6.5 | 3.9 | 9.5 | 5.8 | 8.7 | 3.6 | 6.0 | 4.4 | 9.1 |
| 30 | 0.00 | 0.5 | 0.00 | 0.00 | 0.00 | 0.05 | 0.00 | 0.1 | ≤0.2 | |
| 31 | 0.00 | 0.5 | 0.00 | 0.00 | 0.00 | 0.05 | 0.00 | 0.1 | ≤0.2 | |
| 32 | 0.1 | 0.5 | 0.2 | 0.6 | 0.3 | 0.8 | 0.05 | 1.0 | 0.3 | 0.5 |
| 33 | 0.1 | 0.5 | 0.2 | 0.6 | 0.3 | 0.8 | 0.05 | 1.0 | 0.3 | 0.5 |
| 34 | 0.00 | 0.5 | 0.00 | 0.00 | 0.00 | 0.05 | 0.00 | 0.1 | ≤0.2 | |
| 35 | 0.1 | 0.5 | 0.2 | 0.6 | 0.3 | 0.8 | 0.05 | 1.0 | 0.2 | 0.4 |
| 36 | 0.00 | 0.5 | 0.00 | 0.00 | 0.00 | 0.05 | 0.00 | 0.1 | ≤0.2 | |
| 37 | 0.1 | 0.5 | 0.2 | 0.6 | 0.3 | 0.8 | 0.05 | 1.0 | 0.2 | 0.4 |
| 38 | 0.2 | 1.2 | 0.5 | 1.5 | 0.1 | 0.8 | 0.05 | 1.8 | 0.5 | 0.8 |

*The building blocks refer to the structures of Table IA, by reference to the peak # provided in Table IA.

In one embodiment, the preparation is unfractionated heparin and a percentage of a subset of species, e.g., the total percentage of a subset chains having a structural moiety, in the preparation have been determined, e.g., by mole %, and preferably the method includes determining or confirming that the subset is in that range. In one embodiment, the range for the structural moiety or subset of structural moieties is one or more of the following:

Table ID

Preferred Preliminary Specifications of Structural Entities in Unfractionated Heparin

| Saccharide Building Blocks | Peak | Range A | | Range B | |
|---|---|---|---|---|---|
| N-acetyl Disaccharide | 1 | 3.8 | 6.0 | 3.3 | 5.9 |
| Linkage | 2, 3 | 0.9 | 4.2 | 0.0 | 5.7 |
| 1,6 Anhydro | 7, 8, 19, 20, 34, 36 | 0.0 | 0.9 | 0.0 | 1.3 |
| Galacturonic Acid | 4, 14, 15 | 0.1 | 2.6 | 0.0 | 3.6 |
| Trisaccharide | 30, 31 | 0.0 | 0.1 | 0.0 | 0.2 |
| Mannosamine | 23, 26 | 0.0 | 0.1 | 0.0 | 0.1 |
| Monosulfated Disaccharide | 5, 6, 9, 10, 11 | 7.6 | 9.2 | 6.8 | 9.8 |
| Disulfated Disaccharide | 12, 13, 16, 17, 18, 21, 22 | 17.9 | 19.7 | 17.7 | 20.5 |
| Trisulfated Disaccharide | 27, 29 | 53.6 | 57.8 | 53.2 | 59.4 |
| AT-III Tetrasaccharide | 28 | 3.3 | 4.7 | 2.8 | 5.2 |
| Trisulfated Singly Acetylated Tetrasaccharides | 24, 25 | 0.6 | 1.1 | 0.4 | 1.2 |
| Pentasulfated Tetrasaccharide | 32, 33 | 1.0 | 1.7 | 0.7 | 1.7 |
| Hexasulfated Tetrasaccharide | 37, 38 | 0.9 | 1.3 | 0.8 | 1.4 |
| Tetrasulfated Disaccharide | 35 | 0.2 | 0.4 | 0.2 | 0.4 |

Some methods described herein include making a determination of whether the subject entity is present at a preselected level or within a preselected range and that level or range is expressed in specific units of measurement, e.g., present in a range of 2.0-3.0 mole %. One can perform the method by determining the amount of subject entity in terms of mole % and then compare that with a reference expressed in mole %, in this example, 2.0-3.0 mole %. Preferably, the range is made using a non-uniform factor. One need not, however, make the measurement in terms of mole % and compare it with reference values expressed in mole %. The sample has an actual level of subject entity, which can be expressed as 2.0-3.0 when described in units of mole %. That actual level can also be expressed in other units, e.g., weight %. That actual level is the same regardless of the units in which it is expressed. The specification of mole % in the method is merely to indicate the actual prevalence of the subject entity. The level of specific entity can be measured in terms of other units and the reference value can be expressed in terms of other units, as long as the reference value as expressed in terms of alternative units corresponds to the same amount of subject entity as the reference value expressed in mole %, 2.0-3.0 mole % in this example. Thus, a method which requires showing the subject entity is present at 2.0-3.0 mole % can be performed by showing that the subject entity is present in a range expressed in an alternative unit of measure, e.g., weight %, chain number, or % AUC, wherein the range, as described in the alternative unit of measure, corresponds to the same amount of subject entity which would give the mole % referred to, in this example 2.0-3.0 mole %.

One can establish a functionally equivalent range for an alternative unit of measure by applying art known methods in conjunction with this specification. For example, one can provide samples in the range of X-Y mole %, and then establish the corresponding range for those samples for in terms of an alternative unit of measure.

In one embodiment, the method further includes classifying, selecting, accepting or discarding, releasing or withholding, processing into a drug product, shipping, moving to a different location, formulating, labeling, packaging, releasing into commerce, selling or offering for sale based, e.g., on the result of the determination or upon comparison to a reference standard.

In one embodiment, the method includes determining if one or more of the compounds provided in Table IA is present in a LMWH preparation, and, e.g., present in a range specified in Table IB. In another embodiment, the method includes determining if one or more of the compounds provided in Table IA is present in unfractionated heparin starting material, and, e.g., present in a range specified in Table IC or Table ID. The ranges A, B, C, D and E (or A, B, C and D with reference to table ID) for a given building block are preferred but ranges constructed from a lower endpoint of one range, e.g., B, for a given building block, can be combined with the upper endpoint of another range, e.g., C, for a given building block, to give a range.

In another embodiment, the method includes determining the identity, presence, and/or quantity of at least two or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, or 38) of the structures and/or chains, e.g., the structures and/or chains of Table IA, in a LMWH preparation and/or an unfractionated heparin preparation. In one embodiment, the method includes determining if the subject entities are present in a LMWH preparation in a range disclosed herein, e.g., in Table IB. In one embodiment, the method includes comparing the determination to a reference standard, e.g., the presence of structures and/or chains of Table IA and/or the quantity of structures and/or chains of Table IB. In one embodiment, the method includes determining if the subject entities are present in an unfractionated heparin preparation in a range disclosed herein, e.g., in Table IC or Table ID. In one embodiment, the method includes comparing the determination to a reference standard, e.g., the presence of structures and/or chains of Table IA and/or the quantity of structures and/or chains of Table IC or Table ID.

In a preferred embodiment, the sample is evaluated for the amount of each of the structures in Table IA, e.g., in a range present in Table 1B, Table 1C or Table ID.

In a preferred embodiment, the method includes determining if each of the structures in Table IA is present in a preselected range, e.g., a range disclosed herein. For example, the amount of each of the structures in Table IA of a LMWH preparation is compared with a range, e.g., a range in Table IB (or a corresponding range expressed in a different unit of measure) or the amount of each of the structures in Table IA of an unfractionated heparin preparation is compared with a range, e.g., a range in Table IC or Table ID (or a corresponding range expressed in different units of measure); and optionally, if the test amount falls within the range, selecting or processing the enoxaparin or the unfractionated heparin starting material. Preferably, the amount of one or more structures is determined using a non-uniform factor. This can be done on all or a subset of the structures described in Table IA. Preferred subsets include:
  structure 1 from Table IA;
  one or more of structures 2 and 3 from Table IA;
  one or more of structures 7, 8, 19, 20, 34 and 36 from Table IA;
  one or more of structures 4, 14 and 15 from Table IA;
  one or more of structures 30 and 31 from Table IA;
  one or more of structures 23 and 26 of Table IA;
  one or more of structures 5, 6, 9, 10 and 11 of Table IA;
  one or more of structures 12, 13, 16, 17, 18, 21 and 22 of Table IA;
  structure 28 of Table IA;
  one or more of structures 24 and 25 of Table IA;
  one or more of structures 32 and 33 of Table IA;
  structure 35 of Table IA;
  one or more of the structures 13, 14, 13+14, and 27 in Table IA;
  one or more of the structures 1, 5, 9, 17, 19, 26, 28 and 29 in Table IA;
  one or more of the structures 1, 3, 4, 5, 6, 7, 8, 9, 10, 11, 15, 16, 15+16, 17, 18, 19, 20, 21, 22, 24, 25, 26, 28, 29, 30, 31, 32, 33, 35, 36, 37, and 38 in Table IA;
  one or more of the structures 2, 12, 23 and 34 from Table IA.

In one aspect, the invention features an enriched, isolated or purified preparation of a compound from Table IA.

In one aspect, the invention features a set of standard preparations. The set includes a plurality of standards each having a different concentration of a compound of Table IA. Preferably the standard preparation is free of other carbohydrates. By way of example the concentration of the individual standards can be described in terms of weight/weight, weight/volume, or molarity. In a preferred embodiment the compound is provided in a solvent. The set of standards can be used in the evaluation of a sample, e.g., one can assay for a subject entity and compare the assay result with a value obtained from one or more of the standards. By way of example, one can determine the absorbance or other parameter and compare that with a standard curve for the relevant parameter derived from the set of standard preparations and determine the amount or concentration of the subject entity.

In a preferred embodiment, one or each standard in a set is, individually, an enriched, isolated, or purified preparation.

In a preferred embodiment, the set includes at least 2, 3, 4, 5, or 10 standard preparations.

In another aspect, the invention features making a preparation, e.g., a standard preparation of known concentration, by providing a compound described herein and combining it with a solvent. In a preferred embodiment the standard is at least 90, 95, 99, 99.5, or 99.9% of the carbohydrate in the sample. The percentage can be determined by dry weight, chain, or molarity.

In one aspect, the invention features a reaction mixture that includes one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, or thirty-eight of the compounds of Table IA and 2-O sulfatase and/or $\Delta^{4,5}$ glycuronidase. In one embodiment, the reaction mixture can further include one or more of heparinase I, heparinase II, heparinase III, heparinase IV, heparanase, heparan sulfate GAG lyase I, heparan sulfate GAG lyase II, heparan sulfate GAG lyase III, heparan sulfate GAG lyase IV.

In one embodiment, the reaction mixture includes heparinase I, heparinase II, heparinase III, and 2-O sulfatase. In one embodiment, the reaction mixture includes heparinase I, heparinase II, heparinase III and $\Delta^{4,5}$ glycuronidase. In one embodiment, the reaction mixture includes heparinase I, heparinase II, heparinase III, 2-O sulfatase and $\Delta^{4,5}$ glycuronidase. In one embodiment, the reaction mixture includes heparan sulfate GAG lyase I, heparan sulfate GAG lyase II, heparan sulfate GAG lyase III and 2-O sulfatase. In one embodiment, the reaction mixture includes heparan sulfate GAG lyase I, heparan sulfate GAG lyase II, heparan sulfate GAG lyase III and $\Delta^{4,5}$ glycuronidase. In one embodiment, the reaction mixture includes heparan sulfate GAG lyase I, heparan sulfate GAG lyase II, heparan sulfate GAG lyase III, 2-O sulfatase and $\Delta^{4,5}$ glycuronidase.

In a preferred embodiment the reaction is fully digested.

In one aspect, the invention features a method of evaluating or processing a heparin preparation, e.g., an enoxaparin preparation, that includes making a determination about a heparin preparation, e.g., an enoxaparin preparation, based upon a method or analysis described herein. In one embodiment, the method further includes classifying, selecting, accepting or discarding, releasing or withholding, processing into a drug product, shipping, formulating, labeling, packaging, releasing into commerce, selling the preparation based, e.g., on the analysis. Thus, in a preferred embodiment the party making the evaluation does not practice the method or analysis described herein but merely relies on results which are obtained by a method or analysis described herein.

In one aspect, the invention features a method of analyzing a process, e.g., manufacturing process, of an enoxaparin, e.g., an enoxaparin made by a selected process. The method includes: providing an enoxaparin preparation or providing an unfractionated heparin preparation; analyzing the preparation using, e.g., a method described herein, e.g., to identify and/or quantify one or more structures and/or chains, e.g., one or more structures and/or chains disclosed herein, thereby allowing analysis, e.g., qualitative and/or quantitative analysis, of the one or more structures and/or chains in the preparation. In one embodiment, the method further includes comparing the amount, or size distribution of the one or more structures and/or chains with a reference value, to thereby analyze the manufacturing process.

In one embodiment, the method further includes maintaining the manufacturing process based, at least in part, upon the analysis. In one embodiment, the method further includes altering the manufacturing process based, at least in part, upon the analysis.

In a preferred embodiment the method includes: evaluating a process, e.g., manufacturing process, of an enoxaparin, e.g., an enoxaparin made by a selected process that includes making a determination about the process, e.g., manufacturing process, or enoxaparin, e.g., enoxaparin made by a selected process, based upon a method or analysis described herein. In one embodiment, the method further includes maintaining or altering the manufacturing process based, at least in part, upon the method or analysis. Thus, in a preferred embodiment the party making the evaluation does not practice the method or analysis described herein but merely relies on results which are obtained by a method or analysis described herein.

In a preferred embodiment the method includes comparing two or more heparin preparations, e.g., two or more enoxaparin preparations, e.g., in a method of monitoring or controlling batch-to-batch variation or to compare a preparation to a reference standard. This embodiment includes: providing a first heparin preparation; providing the presence, amount or size distribution of one or more structures and/or chains, e.g., one or more structures and/or chains described herein, in the first sample; optionally, providing a second heparin preparation; providing the presence, amount or size distribution of a structure and/or chain in the second preparation; and comparing the presence, amount or size distribution of the one or more structures and/or chains of the first heparin preparation with the one or more structures and/or chains of the second heparin preparation. In one embodiment, the one or more structures and/or chains are analyzed by a method described herein.

In one embodiment, the method can further include making a decision, e.g., to classify, select, accept or discard, release or withhold, process into a drug product, ship, move to a different location, formulate, label, package, release into commerce, sell or offer for sale the preparation, based, at least in part, upon the determination.

In one aspect, the invention features a method of making a batch of enoxaparin having a preselected property, e.g., meeting a release specification, label requirement, or compendial requirement, e.g., a property described herein. The method includes:
providing a test enoxaparin preparation;
analyzing the test enoxaparin preparation according to a method described herein;
determining if the test enoxaparin preparation satisfies a preselected criteria, e.g., having a preselected relationship with a reference value, e.g., one or more reference values disclosed herein, and selecting the test enoxaparin preparation to make enoxaparin,
thereby making a batch of enoxaparin.

In one aspect, the invention features a method of predicting or ensuring that a batch of enoxaparin will have a preselected property, e.g., that it will meet a release specification, label requirement, or compendial requirement, e.g., a property described herein. The method includes:
providing a test enoxaparin preparation or an unfractionated heparin preparation used to produce a test enoxaparin preparation;
analyzing the test enoxaparin preparation or the unfractionated heparin preparation according to a method described herein;
wherein meeting a preselected criteria, e.g., satisfaction of the preselected reference, e.g., one or more reference disclosed herein, by the test enoxaparin preparation or the unfractionated heparin preparation, is predictive of or ensures that a batch of enoxaparin made from the test enoxaparin preparation or unfractionated heparin preparation will have a preselected property, e.g., it will meet a release specification, label requirement, or compendial requirement, e.g., a property described herein.

In one aspect, the invention features a method of making one or more batches of a polysaccharide preparation, e.g., an enoxaparin preparation, wherein one or more glycoprofile values (e.g., one or more structural property, e.g., the presence, size distribution, or quantity of a structure and/or chain described herein) of the batches meet a preselected criteria, e.g., varies less than a preselected range or has some preselected relationship with a reference standard. For example, it is present at a lower, higher, or equivalent level as a standard or is within (or outside) a range of values. Preferably, evaluation of the value, e.g., the presence of a structure and/or chain, is made by a method described herein. In some embodiments, the method further includes classifying or selecting one or more batches having a structural property that varies less than the preselected range, e.g., a range described herein.

In another aspect, the invention features multiple batches of a polysaccharide preparation, e.g., an unfractionated heparin preparation or enoxaparin preparation, wherein one or more glycoprofile values (e.g., a value determined by a method described herein), for each batch varies less than a preselected range from a pre-selected desired glycoprofile, e.g., a range described herein for unfractionated heparin or enoxaparin. In some embodiments, the method includes determining one or more structural signature (e.g., one or more structural moiety and/or chain) of one or more batches of a product, and selecting a batch as a result of the determination. In some embodiments, the method can also include comparing the results of the determination to preselected values, e.g., a reference standard. In other embodiments, the method can further include adjusting the dose of the batch to be administered, e.g., based on the result of the determination of the structural signature. Preferably, evaluation of the value, e.g., the presence of one or more structure and/or chain, is made by a method described herein.

In another aspect, the invention features a method of determining a reference value for a polysaccharide composition, e.g., an unfractionated heparin preparation or an enoxaparin preparation, and determining the presence and/or amount of one or more structure and/or chain described herein including those provided in Table IA, Table IB and Table IC. Preferably, evaluation of the value, e.g., the presence, size distribution, or quantity of the one or more structure and/or chain, is made by a method described herein.

In another aspect, the invention features a method for determining bioequivalence. The method includes some or all of the following: providing or determining a value for the presence, amount or size distribution of one or more structure and/or chain, e.g., one or more structure and/or chain described herein, in a first heparin preparation, e.g. an enoxaparin preparation; providing or determining the bioavailability of the preparation; providing a reference value, e.g., by providing or determining presence, amount or size distribution of one or more structure and/or chain, e.g., one or more structure and/or chain described herein, in a second heparin preparation, e.g., an enoxaparin preparation, and comparing the amount or size distribution of one or more structure and/or chain of the first preparation and/or the reference value, e.g., a second heparin preparation. In some embodiments, the reference value can include one or more of the ranges described herein for enoxaparin. Preferably, evaluation of the one or more structure and/or chain is made by a method described herein.

In some embodiments, the method further comprises monitoring for presence, tissue distribution, spatial distribution, temporal distribution or retention time, in a cell or a subject, e.g., an experimental animal. In some embodiments, the method includes determining the amount or size distribution of one or more structure and/or chain described herein of one or more batches of a product. In some embodiments, the method further includes selecting a batch as a result of the determination. In some embodiments, the method further includes comparing the results of the determination to preselected values, e.g., a reference standard.

In another aspect, the invention provides a method for determining the safety or suitability of a heparin, e.g., a LMWH, preferably an enoxaparin preparation for use in a particular indication. The method includes some or all, typically all, of the following: determining the presence, amount or size distribution of one or more structures and/or chains, e.g., one or more structures and/or chains described herein, in the heparin; providing a reference value or sample; determining if the heparin is acceptable, e.g., by comparing a value for the presence, amount or size distribution of one or more structures and/or chains of the heparin with the reference value or with a value determined from the sample. For example, when the heparin is enoxaparin, one or more of the ranges described herein can be used as a reference value. When a preselected index of similarity is met, the heparin can be determined to be safe or suitable. In some embodiments, the reference sample is associated with one or more undesired effects. In some embodiments, the reference sample is associated with one or more desired effects. Preferably, evaluation of the presence, amount or size distribution of the one or more structure and/or chain, e.g., one or more structure and/or chain described herein, in the heparin is made by a method described herein.

In another aspect, the invention features a method of one or more of providing: a report to a report receiving entity; evaluating a sample of enoxaparin for compliance with a reference standard, e.g., an FDA requirement; seeking indication from another party that an enoxaparin sample meets some predefined requirement; or submitting information about an enoxaparin sample to another party. Exemplary receiving entities or other parties include a government, e.g., the U.S. federal government, e.g., a government agency, e.g., the FDA.

The method includes one or more (and preferably all) of the following:

performing one or more steps in making and/or testing a batch of enoxaparin in a first country, preferably the US;

sending at least an aliquot of the sample outside the first country, e.g., sending it outside the United States, to a second country;

preparing, or receiving, a report which includes data about the structure of the enoxaparin sample, e.g., data related to a structure and/or chain described herein, e.g., data generated by one or more of the methods described herein; and providing said report to a report recipient entity.

In a preferred embodiment, the report receiving entity can determine if a predetermined requirement or reference value is met by said data and optionally, a response from the report receiving entity is received, e.g., by a manufacturer, distributor or seller of enoxaparin. In a preferred embodiment, upon receipt of approval from said report recipient entity, enoxaparin from said batch is selected, packaged, or placed into commerce.

In one aspect, the invention features a method of evaluating a sample of enoxaparin that includes receiving data with regard to the presence or level of a structure and/or chain described herein in an enoxaparin sample, e.g., wherein the data was prepared by one or more methods described herein; providing a record which includes said data and optionally includes an identifier for a batch of enoxaparin; submitting said record to a decision-maker, e.g., a government agency, e.g., the FDA; optionally, receiving a communication from said decision maker; optionally, deciding whether to release market the batch of Lovenox® or enoxaparin based on the communication from the decision maker. In one embodiment, the method further includes releasing the sample.

Any of the methods described herein can further include determining and/or providing an analysis regarding one or more biological activity of the preparation or sample. For example, the biological activity can be one or more of anti-Xa activity, anti-IIa activity, molecular weight distribution and average molecular weight. The methods can further include comparing any of anti-Xa activity, anti-IIa activity, molecular weight distribution and average molecular weight to a reference standard for enoxaparin. In one embodiment, the reference standard for anti-Xa activity is about 100 IU/mg; the reference standard for anti-IIa activity is about 30 IU/mg; the reference standard for molecular weight distribution is 16% are <2000 Da species, greater than or equal to 68% are 2000-8000 Da species, and less than or equal to 18% are >8000 Da species; the reference standard for the average molecular weight is about 4500 Da. In one embodiment the reference standard is having two or four chains terminating in a 1,6 anhydro structure.

A "polysaccharide" as used herein is a polymer composed of monosaccharides linked to one another. In many polysaccharides, the basic building block of the polysaccharide is actually a disaccharide unit, which can be repeating or non-repeating. Thus, a unit when used with respect to a polysaccharide refers to a basic building block of a polysaccharide and can include a monomeric building block (monosaccharide) or a dimeric building block (disaccharide)

A polysaccharide according to the invention can be a mixed population of polysaccharides, e.g., a heparin preparation, e.g., synthetic heparin preparation, an unfractionated heparin preparation or LMWH preparation. As used herein, a "mixed population of polysaccharides" is a polydisperse mixture of polysaccharides. The term "polydisperse" or "polydispersity" refers to the weight average molecular weight of a composition (Mw) divided by the number average molecular weight (Mn). The polydispersity of unfractionated heparin and various LMWHs are known, as are methods for determining polydispersity. Compositions with polydispersity near 1 are more homogeneous, containing fewer different polysaccharides. As an example, a preparation of unfractionated heparin, which contains a wide variety of polysaccharides of differing lengths and compositions, has a polydispersity of about 1.5 to 2.0.

The term "enoxaparin preparation" as used herein refers to both enoxaparin drug substance preparations and enoxaparin drug product preparations. The term "drug product preparation" refers to a polysaccharide preparation having the purity required for and being formulated for pharmaceutical use. The term "drug substance preparation" refers to a preparation having the polysaccharide constituents for pharmaceutical use but is not necessarily in its final formulation and/or comprises one or more non-product contaminant (e.g., one or more inorganic product such as sulfate, chloride, acetate and phosphates, protein contaminant, process by-product such as benzyl alcohol and benzethonium).

The term "unfractionated heparin (UFH)" as used herein, is heparin purified from porcine intestinal mucosa that can be used as a starting material in the process to form enoxaparin.

The term preparation, as used herein can be an enriched preparation, an isolated preparation, or a purified preparation.

The term "enriched preparation" as used herein is a preparation which is significantly enriched for the subject entity, e.g., a structure or chain. Significant enrichment can, by way of example, be based on weight/weight, chain number analysis or molarity. Enrichment can be with respect to a naturally occurring material, in UFH or in a LMWH, e.g., enoxaparin. In some embodiments, in the case of a subject entity which is present in UFH, the subject entity is present in the enriched preparation at at least 2, 5, 10, 50 or 100 times the concentration (as determined, e.g., by weight/weight, chain number analysis or molarity) it is found in UFH. In some embodiments, in the case of a subject entity which is present in enoxaparin, the subject entity is present in the enriched preparation at at least 2, 5, 10, 50 or 100 times the concentration (as determined, e.g., by weight/weight, chain number analysis or molarity) it is found in enoxaparin. In some embodiments the subject entity can be accompanied by a solvent, diluent, or carrier. In other embodiments the subject entity is substantially free of a solvent, diluent, or carrier. In some embodiments the subject entity can be accompanied by a medium, e.g., a buffer, matrix or other material used to effect separation and/or eluent, used in its purification. In other embodiments the preparation is substantially free of such elements. In a preferred embodiment the preparation is provided in an enclosure which is substantially free of contaminant carbohydrates.

The term "isolated preparation" as used herein refers to a preparation containing a subject entity, e.g., a structure or chain, that is substantially free of at least one and preferably all other carbohydrate with which it normally occurs. By way of example, in the case of a subject entity present in UFH the subject entity is substantially free of at least one and preferably all other carbohydrate (a contaminating carbohydrate) with which it occurs in UFH. In the case of a subject entity present in enoxaparin the subject entity is substantially free of at least one and preferably all other carbohydrate with which it occurs in enoxaparin. Substantially free means that at least 90, 95, 99, 99.5, or 99.9%, or substantially all, of a contaminating entity, e.g., a carbohydrate, has been removed. This determination can, by way of example, be based on weight/weight or chain number analysis. In some embodiments the subject entity can be accompanied by a solvent, diluent, or carrier. In other embodiments the subject entity is substantially free of a solvent, diluent, or carrier. In some embodiments the subject entity can be accompanied by a medium, e.g., a buffer, matrix or other material used to effect separation and/or eluent, used in its purification. In other embodiments, the preparation is substantially free of such elements. In a preferred embodiment, the preparation is provided in an enclosure which is substantially free of contaminant carbohydrates. In some embodiments, in the case of a subject entity which is present in UFH, the subject entity is present in the isolated preparation at at least 2, 5, 10, 50 or 100 times the concentration (as determined, e.g., by weight/weight, chain number analysis or molarity) it is found in UFH. In some embodiments, in the case of a subject entity which is present in enoxaparin, the subject entity is present in the isolated preparation at at least 2, 5, 10, 50 or 100 times the concentration (as determined, e.g., by weight/weight, chain number analysis or molarity) it is found in enoxaparin.

The term "purified preparation" as used herein refers to a preparation containing a subject entity, e.g., a structure or chain, that is at least 90, 95, 99, 99.5 or 99.9% the subject entity or is substantially all subject entity. This determination can, by way of example, be based on weight/weight or chain number analysis. In some embodiments the subject entity can be accompanied by a solvent, diluent, or carrier. In some embodiments the subject entity can be accompanied by a medium, e.g., a buffer, matrix and/or eluent, used in its purification. In other embodiments the purified preparation does not contain a solvent, diluent, carrier or medium used in purification. In a preferred embodiment the purified preparation is provided in an enclosure which is substantially free of contaminant carbohydrates. In some embodiments, the case of a subject entity which is present in UFH, the subject entity is present in the purified preparation at at least 2, 5, 10, 50 or 100 times the concentration (as determined, e.g., by weight/weight, chain number analysis or molarity) it is found in UFH. In some embodiments, in the case of a subject entity which is present in enoxaparin, the subject entity is present in the purified preparation at at least 2, 5, 10, 50 or 100 times the concentration (as determined, e.g., by weight/weight, chain number analysis or molarity) it is found in enoxaparin.

The term "extinction coefficient" as used herein refers to a factor used to calculate the concentration of a standard in solution. For example, if a solution of a sample (e.g., a saccharide sample, such as a 1,6 anhydro species) has an absorbance (A), and the extinction coefficient of the saccharide is E, then concentration (C) can be determined according to the equation:

$$A=ECx$$

(where x=path length of the cuvette used to measure the absorbance and this value is usually=1 cm).

The extinction coefficient of a sample (e.g., a saccharide sample, such as a 1,6 anhydro species) can vary based on the solution in which it is measured. For example, oligosaccharide products measured in 30 mM HCl generally use an extinction coefficient=5500 $M^{-1}$, whereas for oligosaccharide products measured in sodium phosphate/NaCl buffer generally use an extinction coefficient=3800 $M^{-1}$.

The term "response factor" as used herein refers to a factor calculated for the determination of an amount of sample as a function of weight. For example, a factor calculated for a standard sample injected onto a column, e.g., an HPLC column. For a standard of a known concentration, an injection of X mg onto a column (e.g., an HPLC column) having a peak corresponding to a standard that has an area A correlates to a response factor for that standard=A/X.

Complex polysaccharide drug products can be isolated or derived from natural sources and are complex mixtures of polysaccharide chains that differ from one another both in terms of size and chemical sequence that comprises each polysaccharide chain. Chain sequence differences can arise both from differences intrinsic to the cell and tissue-specific biosynthesis pathway by which these complex polysaccharides are made as well as from differences that arise as a function of the process of isolating or preparing polysaccharide substances from natural sources. For example, the LMWHs are derived from unfractionated heparin (UFH) primarily through chemical or enzymatic depolymerization of the polysaccharide chains. Thus, different LMWHs can be made by various depolymerization processes. A process used to make a LMWH can cause one or more unique structural modifications to the polysaccharide chains of the polysaccharide drug, such as heparin. For example, esterification of the carboxylate functional group on the uronic acid followed by β-elimination results in the formation of a $\Delta^{4,5}$ double bond on the non-reducing end as well as the formation of some chains having 1,6-anhydro derivatives. In addition, differences can arise in LMWH preparations due to variation in the starting material. As a result of these and other structural differences, different LMWHs can have distinct pharmacological and/or structural profiles.

The details of one or more embodiments of the invention are set forth in the accompanying drawings and the description below. Other features, objects, and advantages of the invention will be apparent from the description and drawings, and from the claims.

DETAILED DESCRIPTION

The drawings are first briefly described.

FIG. 1 is a trace of UV absorbance at 232 nm from an RPHPLC analysis of enoxaparin digested with a combination of heparinases I-III. The peaks are identified in Table IA. The arrow indicates an internal standard. Peaks 13 and 14 and peaks 15 and 16 are under the same peak. The structures of these peaks are further resolved by the traces of FIGS. 2 and 3, below.

FIG. 2 is a trace of UV absorbance at 232 nm from an RPHPLC analysis of enoxaparin digested with heparinases I-III and 2-O-sulfatase. The peaks are identified in Table IA. The arrow indicates an internal standard.

FIG. 3 is a trace of UV absorbance at 232 nm from an RPHPLC analysis of enoxaparin digested with heparinases I-III, 2-O-sulfatase, and $\Delta^{4,5}$ glycuronidase. The peaks are identified in Table IA. The arrow indicates an internal standard.

FIG. 4 is a trace of UV absorbance at 232 from an RPHPLC analysis of unfractionated heparin digested with a combination of heparinases I-III. The peaks are identified in Table IC. Peaks 13 and 14 and peaks 15 and 16 are under the same peak. The structures of these peaks are further resolved by the traces of FIGS. 5 and 6, below.

FIG. 5 is a trace of UV absorbance at 232 nm from an RPHPLC analysis of unfractionated heparin digested with heparinases I-III and 2-O-sulfatase. The peaks are identified in Table IC. The arrow indicates an internal standard.

FIG. 6 is a trace of UV absorbance at 232 nm from an RPHPLC analysis of unfractionated heparin digested with heparinases I-III, 2-O-sulfatase, and $\Delta^{4,5}$ glycuronidase. The peaks are identified in Table IC. The arrow indicates an internal standard.

Reference Values and Standards

Figure 1:
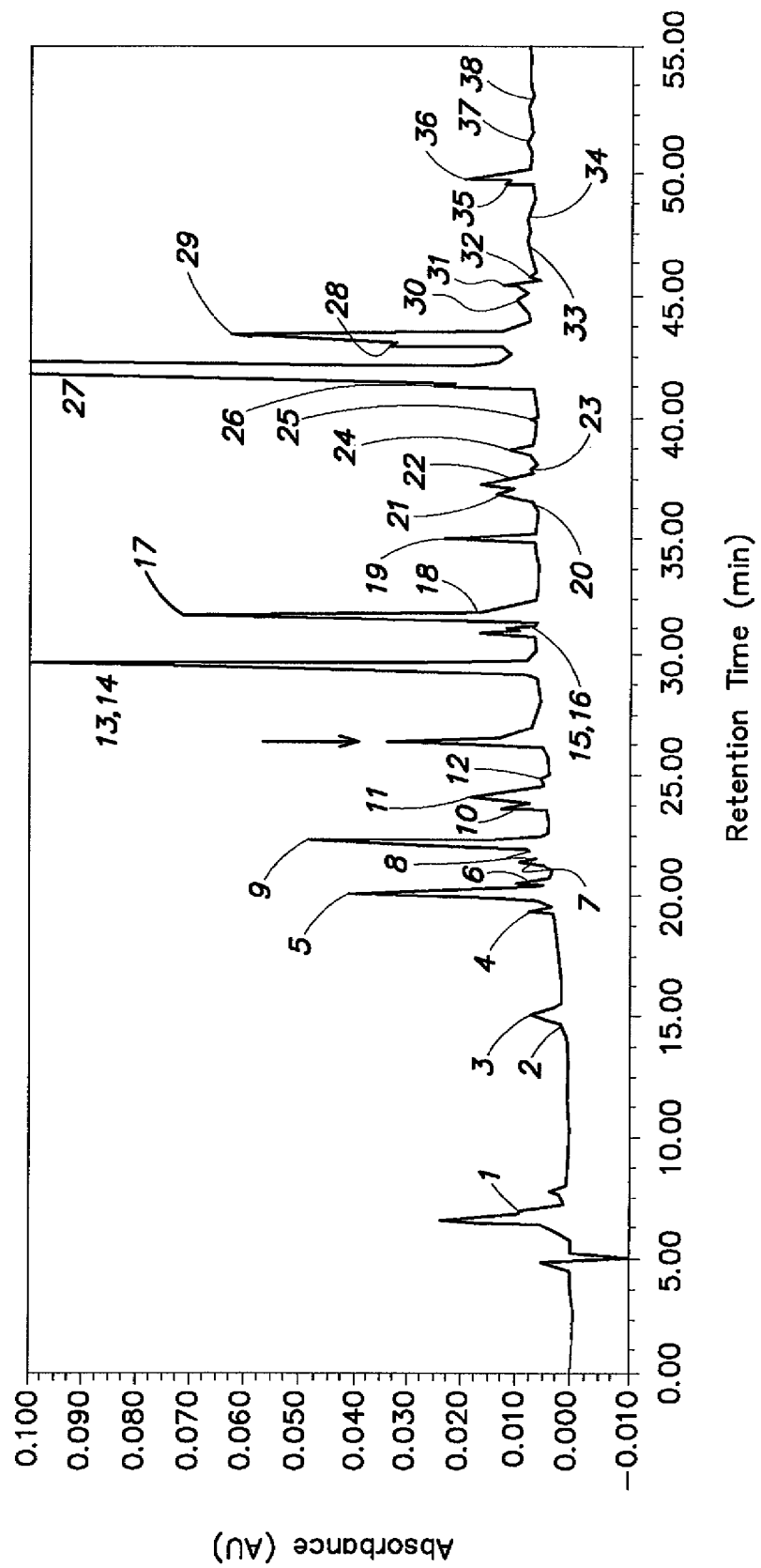
Figure 2:
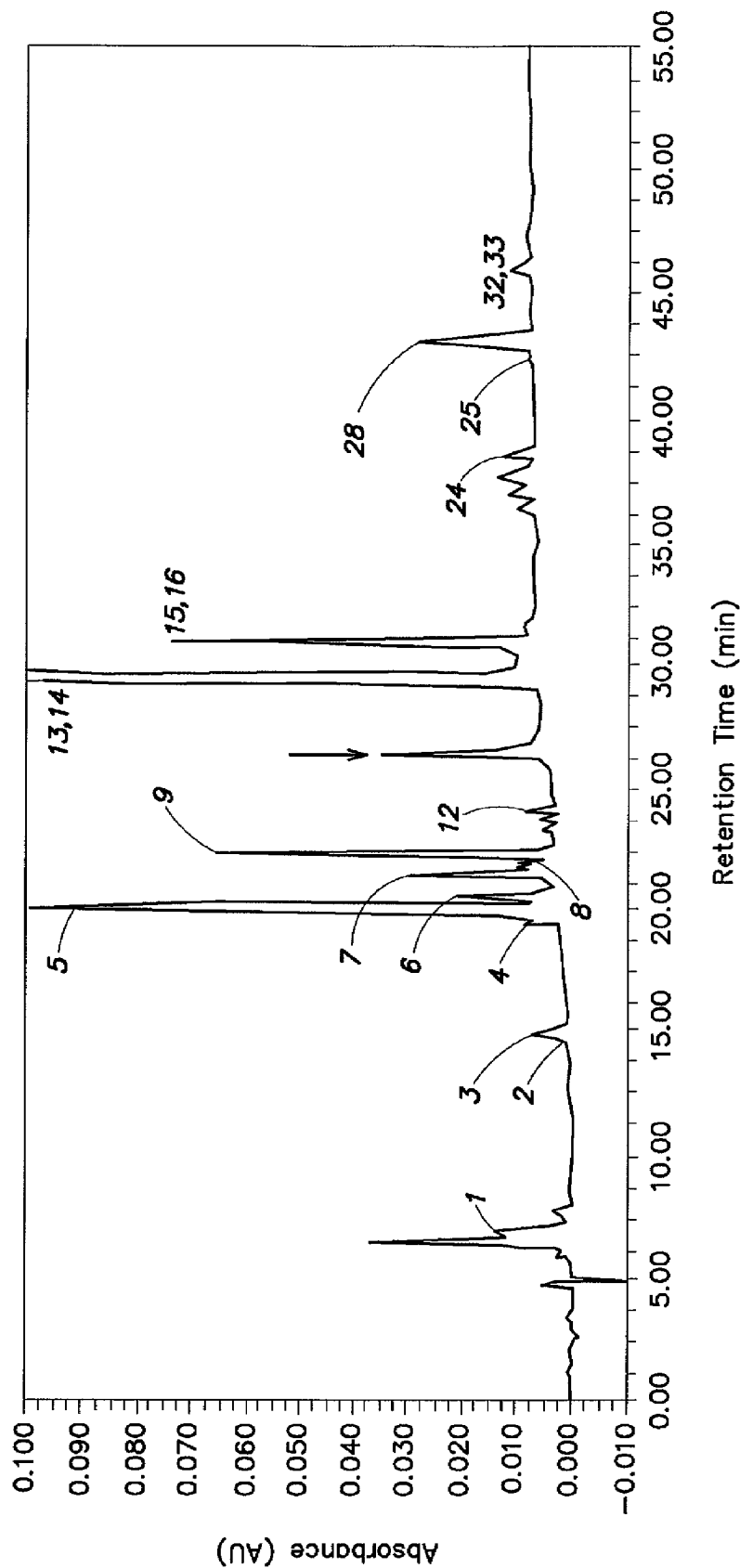
Figure 3:
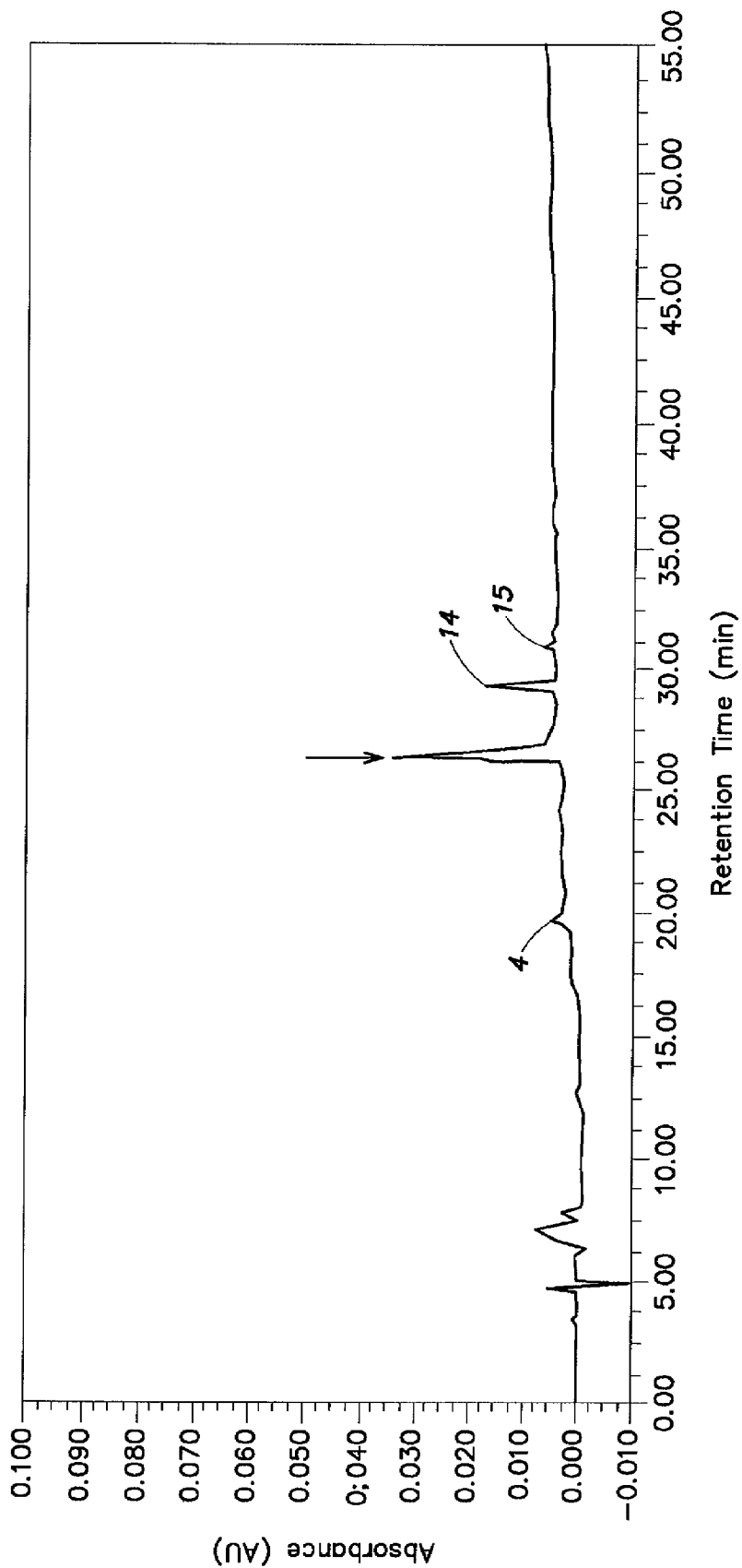
Figure 4:
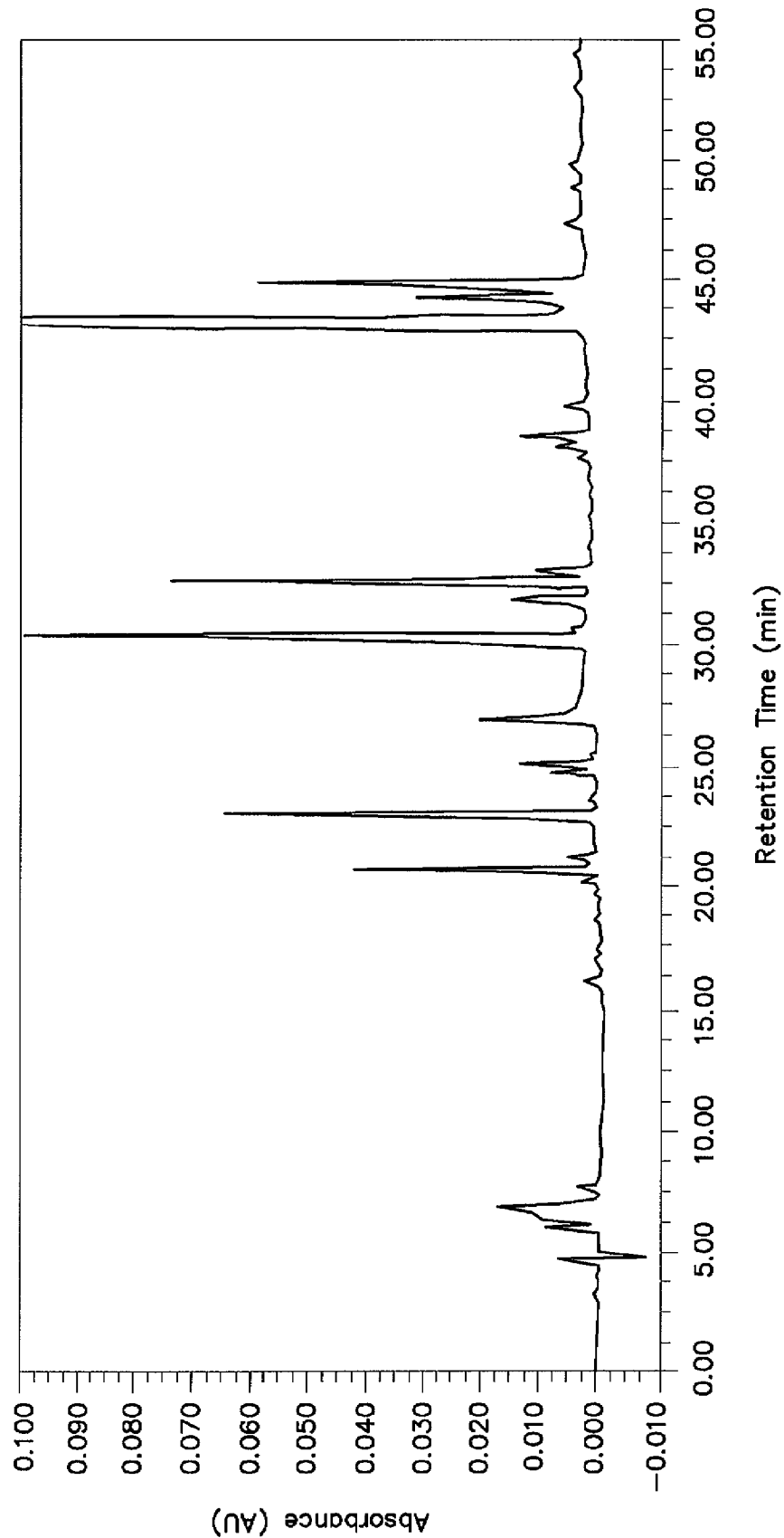
Figure 5:
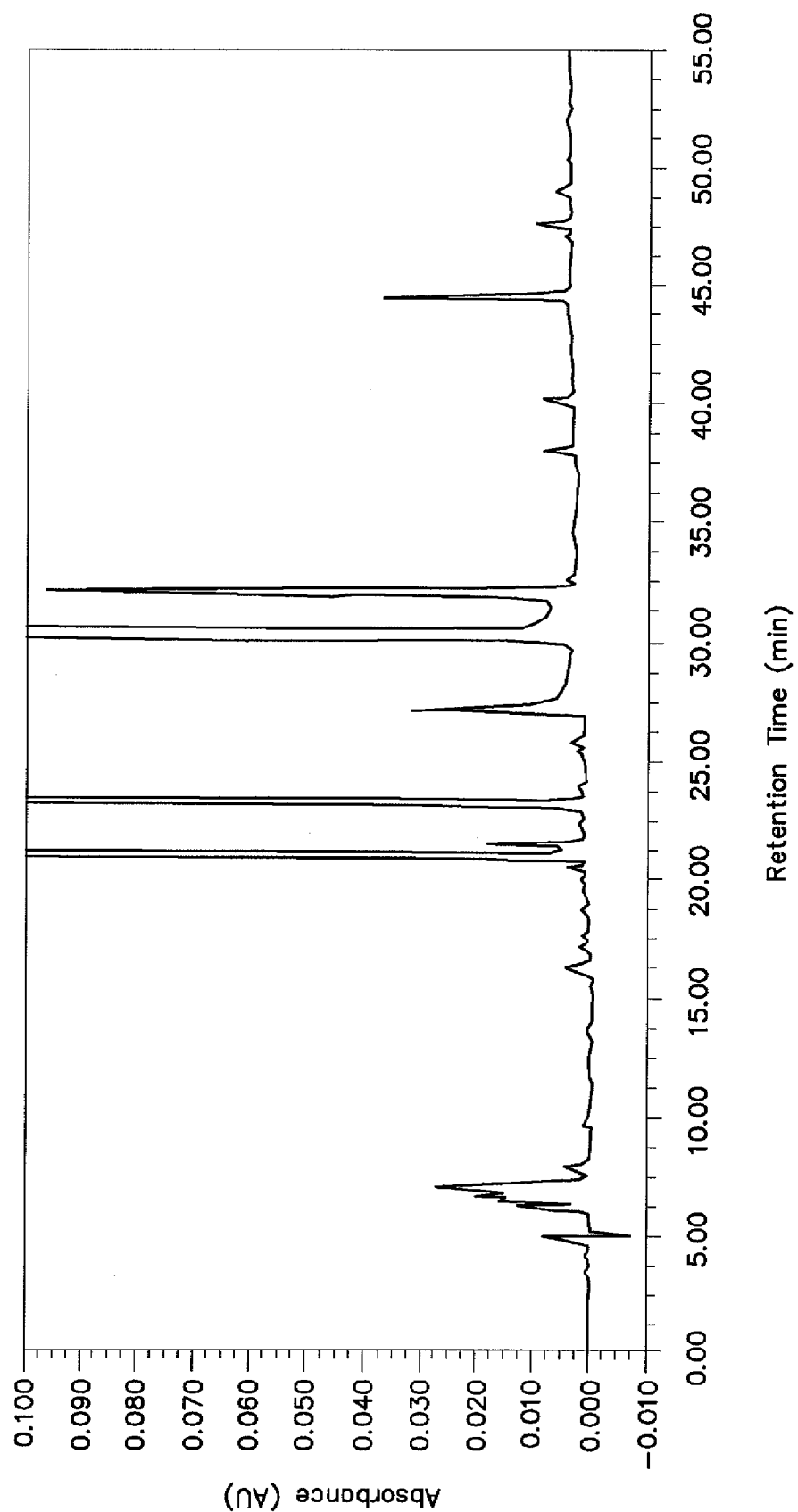
Figure 6:
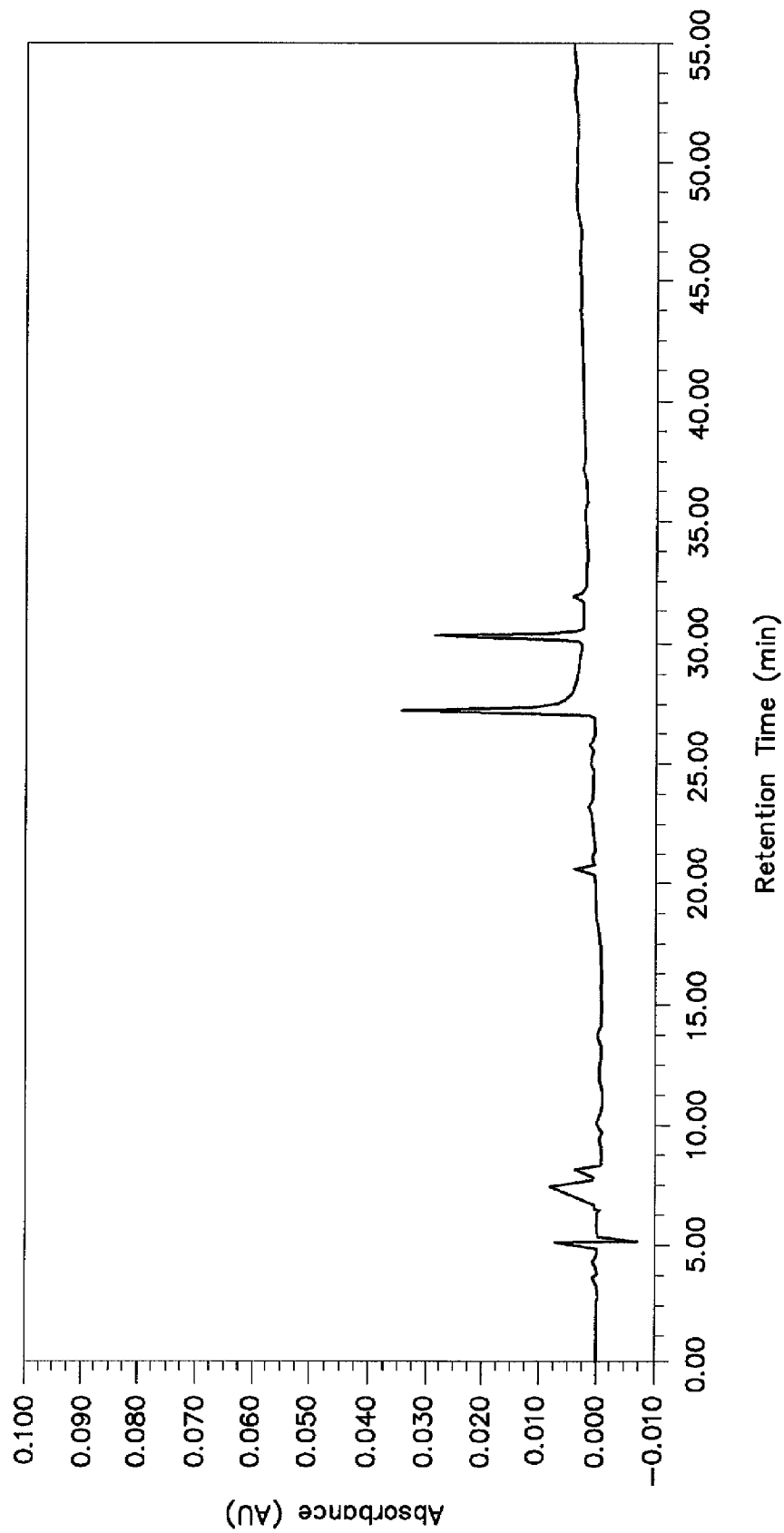
Figure 7:
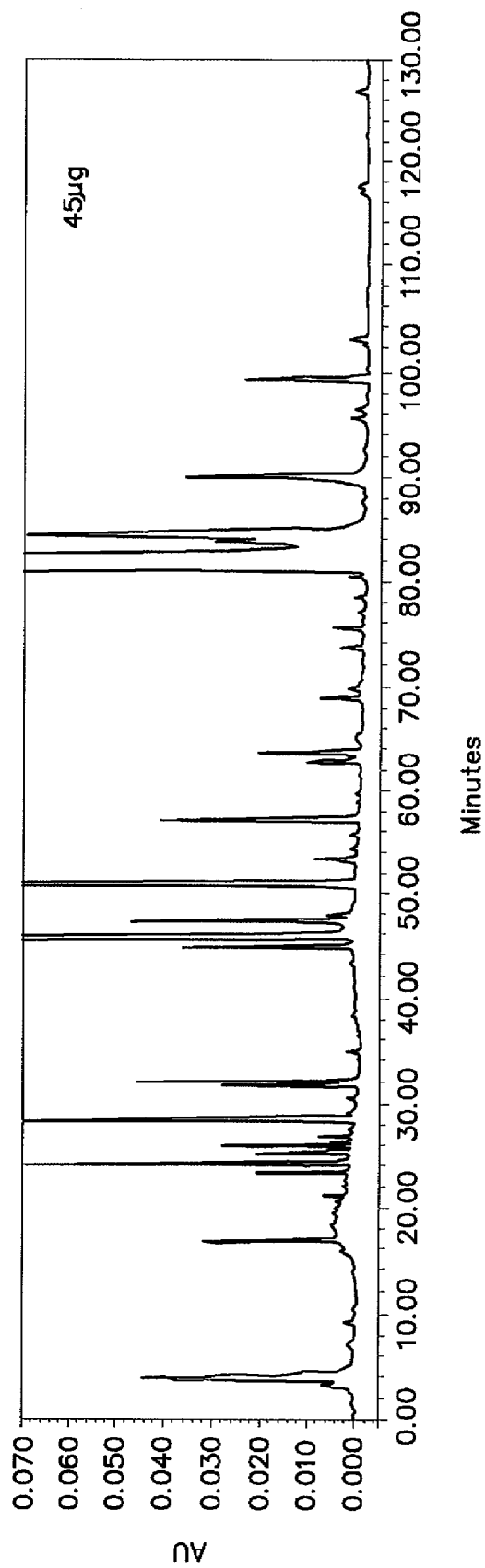
FIG. 7 is a trace of UV absorbance at 232 nm from SAX-HPLC analysis of enoxaparin digested with heparinases I-III.
Figure 8:
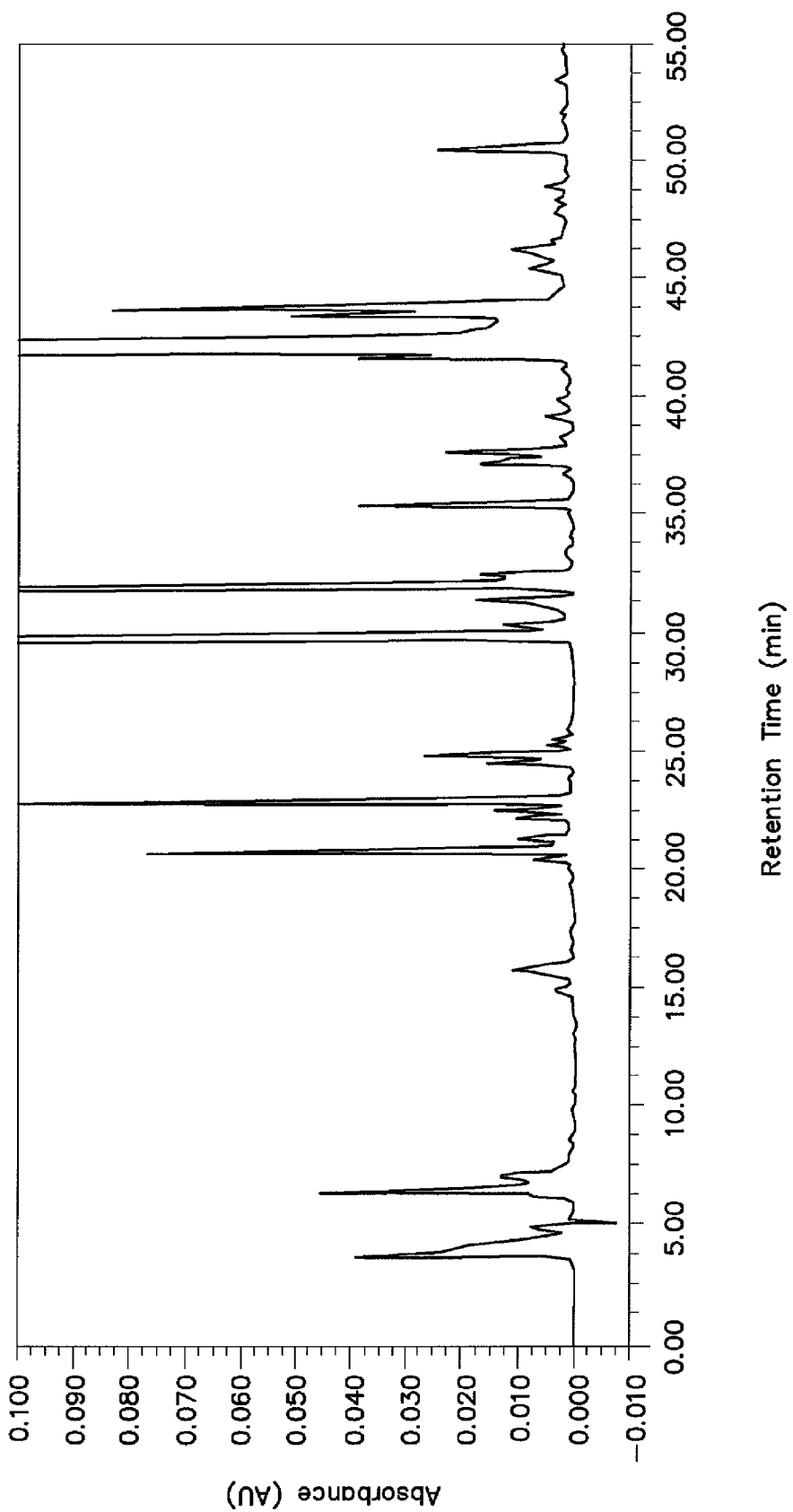
FIG. 8 is a trace of UV absorbance at 232 nm from an RPHPLC analysis of enoxaparin digested with heparinases from *Bacteroides* thetaiotaomicron.

A reference value, by way of example, can be a value determined from a reference sample (e.g., a commercially available sample or a sample from previous production). For example, a reference value can be a value for a range for the amount of a subject entity in a sample, e.g., a reference sample. The reference value can also be a release standard (an example of a release standard is a standard which should be met to allow commercial sale of a product) or other production standard, e.g., a standard which is imposed, e.g., by a party, e.g., the FDA, on a LMWH, e.g., enoxaparin.

The reference standard can be derived from any of a number of sources. The reference standard can be one which was set or provided by (either solely or in conjunction with another party, e.g., a regulatory agency, e.g., the FDA) the manufacturer of the drug or practitioner or a process to make the drug. The reference standard can be one which was set or provided by (either solely or in conjunction with another party, e.g., a regulatory agency, e.g., the FDA) a party other than the party manufacturing a drug and practicing a method disclosed herein, e.g., another party which manufactures the drug or practices a process to make the drug. The reference standard can be one which was set or provided by (either solely or in conjunction with another party) a regulatory agency, e.g., the FDA, to the manufacturer of the drug or practitioner of the process to make the drug, or to another party licensed to market the drug. For example, the reference standard can be a production, release, or product standard required by the FDA. In preferred embodiments, a reference standard is a standard required of a pioneer or a generic.

The reference standard can be one which was set or provided by Aventis Pharma SA, its fully owned subsidiaries, its successors and assigns or agents, either solely or in conjunction with another party, e.g., a regulatory agency, e.g., the FDA, for production or release of enoxaparin.

The reference standard can be one which was set or provided by Momenta Pharmaceuticals, Inc., its fully owned subsidiaries, its successors and assigns or agents, either solely or in conjunction with another party, e.g., a regulatory agency, e.g., the FDA, for production or release of a LMWH, e.g., enoxaparin.

The reference value can be a statistical function, e.g., an average, of a number of values. The reference value can be a function of another value, e.g., of the presence, distribution or amount of a second entity present in the sample, e.g., an internal standard.

Evaluation against a reference value can be used to determine if a particular structure or chain is present in an enoxaparin sample or is present at preselected value or within a preselected range A sample described herein (e.g., an unfractionated heparin or a low molecular weight heparin such as enoxaparin or Lovenox®) can be digested with one or more heparin-degrading enzymes. The heparin degrading enzyme(s) can be, e.g., one or more enzyme of heparinase, heparin lyase, HSGAG lyase, a lyase described as a GAG lyase that can also degrade heparin, and/or any polypeptide described as a hydrolase, sulfatase/sulfohydrolase, or glycosyl hydrolase/glycosidase. For example, the heparin preparation can be digested with one or more of: an unsaturated glucuronyl hydrolase (e.g., *F. heparinum* $\Delta^{4,5}$ glycuronidase, *B. thetaiotaomicron* $\Delta^{4,5}$ glycuronidase); a glucuronyl hydrolase (e.g., mammalian α-iduronidase, β-glucuronidase); a sulfohydrolase (e.g., *F. heparinum* 2-O-sulfatase, 6-O-sulfatase, 3-O-sulfatase, *B. thetaiotaomicron* 6-O-sulfatase, a mucin desulfating enzyme, mammalian N-acetylglucosamine-6-sulfatase, mammalian iduronic acid-2-sulfatase); a N-sulfamidase (e.g., *F. heparinum* N-sulfamidase, mammalian heparan-N-sulfatase); an arylsulfatase; a hexosaminidase; a glycosyl hydrolase (e.g., endo-N-acetyl glucosaminidase); a heparinase (e.g., *Flavobacterum heparinum* heparinase I, *Flavobacterum heparinum* heparinase II, *Flavobacterum heparinum* heparinase III, *Flavobacterum heparinum* heparinase IV); an endoglycoronidase (e.g., mammalian heparanase); a heparin/heparan sulfate lyase (e.g., *Bacteroides thetaiotaomicron* HSGAG lyase I, *Bacteroides thetaiotaomicron* HSGAG lyase II, *Bacteroides thetaiotaomicron* HSGAG lyase III, *Bacteroides thetaiotaomicron* GAG lyase IV); and functional fragments and variants thereof. It can also include a polypeptide described as above (e.g., GAG lyase, glycosyl hydrolase, sulfatase, sulfamidase, glucuronidase, hexosaminidase, etc.) derived from microorganisms other than *Flavobacterium heparinum* (a.k.a. *Pedobacter heparinus*) or *Bacteroides thetaiotaomicron*. For example, *Haloarcula marismortui, Agrobacterium tumefaciens, Streptococcus pneumoniae, Streptococcus pneumoniae, Streptococcus pyogenes, Streptococcus agalactiae, Streptococcus intermedius, Streptococcus suis, Enterococcus faecalis, Rhodopseudomonas palustris, Nitrobacter winogradskyi, Nitrobacter hamburgensis, Bradyrhizobium japonicum, Rhizobium meliloti, Mesorhizobium loti, Spinghobacterium* sp., *Brucella abortus biovar, Brucella melitensis, Solibacter usitatus, Acidobacterium capsulatum, Microbulbifer degradans, Pseudomonas aeruginosa, Burkholderia pseudomonascepacia, Geobacter metallireducens, Prevotella* sp., *Serrata marcescens, Cornybacterium* sp., *Anaeromyxobacter dehalogenans, Rhodopirellula baltica, Pirellula marina*, and/or *Gemmata obscuriglobus. Bacteroides thetaiotaomicron* HSGAG lyase I, *Bacteroides thetaiotaomicron* HSGAG lyase II, *Bacteroides thetaiotaomicron* HSGAG lyase III, and *Bacteroides thetaiotaomicron* GAG lyase IV are described in U.S. patent Ser. No. 11/592,622, the contents of which is incorporated herein by reference.

Prior to digestion, the sample can be lyophilized and/or dried in a vacuum oven, e.g., at about 40° C., 43° C., 46° C., 49° C., 52° C., or 55° C., for about 2, 4, 6, 8, 10, 12, 14, 16, 18, 20, 22, or 24 hours. For example, the sample can be lyophilized and/or dried under one of the following conditions: 40° C. for 12 hours; 46° C. for 8 hours; 49° C. for 6 hours; 52° C. for 4 hours. A sample can be suspended in water or a suitable buffer (e.g., 1 mM calcium acetate, 25 mM sodium acetate, pH 7.0) at a concentration of about 1, 2, 5, 10, 20, 50, or 100 mg/mL. One or more heparin degrading enzyme can be added to the sample. In some embodiments, heparinase I, heparinase II and heparinase III or HSGAG lyase I, HSGAG lyase II and HSGAG III (or combinations of these enzymes) are added to the sample. The sample is digested at a temperature of about 18° C., 25° C., 30° C., 37° C., or 45° C. for about 6, 12, 16, 18, 20 or 24 hours, e.g., at about 25° C. for 20 hours; at 30° C. for about 16 hours; at about 37° C. for 12 hours.

In some embodiments, the digestion mixture includes a heparinase I at about 1-5 IU/mg sample (e.g., about 2, 4, 5 IU/mg sample). In some embodiments, the digestion mixture includes a heparinase II at about 1-5 IU/mg sample (e.g., about 2, 4, 5 IU/mg sample). In some embodiments, the digestion mixture includes a heparinase III at about 1-5 IU/mg sample (e.g., about 2, 4, 5 IU/mg sample). Preferably, a combination of heparinase I, heparinase II and heparinase III are used at about 4 to 5 IU/mg of each. In another embodiment, the digestion mixture includes a heparinase I at about 1-5 IU/mg sample (e.g., about 2, 4, 5 IU/mg sample), a heparinase II at about 1-5 IU/mg sample (e.g., about 2, 4, 5 IU/mg sample), a heparinase HI at about 1-5 IU/mg sample (e.g., about 2, 4, 5 IU/mg sample), and a 2-O sulfatase at about 1 IU/mg. In another embodiment, the digestion mixture includes a heparinase I at about 1-5 IU/mg sample (e.g., about 2, 4, 5 IU/mg sample), a heparinase II at about 1-5 IU/mg sample (e.g., about 2, 4, 5 IU/mg sample), a heparinase III at about 1-5 IU/mg sample (e.g., about 2, 4, 5, IU/mg sample), a 2-O sulfatase at about 1 IU/mg and $\Delta^{4,5}$ glycuronidase at about 1 IU/mg.

Following digestion, the enzymes are removed from the sample mixture, e.g., using a $Ni^{2+}$ column, a size-exclusion column, dialysis, ultrafiltration, or the like. The enzymes can be inactivated by heating (e.g., at 65° C. for 20 minutes) following digestion. The sample can be stored, e.g., at −85° C., −70° C., −20° C., 4° C., 18° C., or 25° C. for a period of time prior to analysis.

A digested sample can be separated using reverse phase high performance liquid chromatography (RPHPLC). Typical reverse phase chromatography substrates, e.g., resins and beads, useful in the methods described herein include C4, C8, C18, and phenyl, derivatized versions of the above (e.g., amido embedded versions), cyanopropylsilane, and poly(divinylbenzene-vinylpyrrolidone). Various particle sizes can be used, including 1 Tm, 2 Tm, 3 Tm, 5 Tm, 10 Tm, 15 Tm, and 20 Tm. Appropriate resins and beads and particle size can be selected based upon the sample size. For example, when about 15 μg, 30 μg, 45 μg sample is used, a C18 column with a 5 Tm particle size can be used.

Useful mobile phases include about 10-80% (e.g., about 10%, 15%, 20%, 25%, or 30%) diethyl ether, methyl t-butyl ether, dioxane, acetonitrile, tetrahydrofuran, 2-propanol, and methanol in water or an aqueous buffer. Various ratios of the mobile phase in water can be used, e.g., 5:95, 10:90, 15:85 and 25:75. A mobile phase that comprises at least one salt chosen from sodium chloride, sodium acetate, potassium chloride, potassium acetate, potassium phosphate, ammonium phosphate, ammonium acetate, sodium phosphate monobasic, magnesium chloride, tris chloride, tris acetate, sodium perchlorate—sodiumphosphate monobasic, methane sulfonic acid-ammonium methanesulfonate.

Cethexonium bromide, Triethylamine, tributylamine, tripentylamine, dibutylamine, tetrabutyl ammonium bromide; tetrabutyl ammonium chloride; tetrabutyl ammonium dihydrogen phosphate; tetrabutyl ammonium hydrogen sulfate; tetrabutyl ammonium hydroxide; tetrabutyl ammonium iodide; tetrabutyl phosphonium bromide; tetrabutyl phosphonium hydrogen sulfate; tetradecyl trimethyl ammonium bromide; tetradecyl trimethyl ammonium hydrogensulfate; tetraethyl ammonium bromide; tetraethyl ammonium hydrogen sulfate; tetraethyl ammonium hydroxide; tetraheptyl ammonium bromide;

tetrahexylammonium bromide; tetrahexyl ammonium dihydrogen phosphate;

tetrahexyl ammonium hydrogen sulfate; tetramethyl ammonium bromide; tetramethyl ammonium hydrogen sulfate; tetramethyl ammonium hydroxide; tetramethyl ammonium sulfate; tetraoctyl ammonium bromide; tetrapentyl ammonium bromide; tetrapropyl ammonium bromide; tetrapropyl ammonium hydrogen sulfate; tetrapropyl ammonium hydroxide can be used as an ion-pairing agent. In some embodiments, the ion-pairing agent is present at a concentration of about 5, 10, 15, 20, 25, 30, 35, 40, 45, or 50 mM. In some embodiments, the mobile phase uses a gradient of a salt, e.g., NaCl or KCl. For example, the salt concentration can increase from, e.g., about 0.0, 0.1, or 0.2 M, to, e.g., about 0.6, 0.7, 0.8, 0.9, 1.0 or 1.5 M, over a period of time, e.g., about 30, 45, 60, 75, 90, 105, 120, 135 or 160 minutes (e.g., 0.0M to 0.6 M over 60 minutes, 0.1 to 0.8M over 120 minutes, 0.0 to 1.5M over 160 minutes). The gradient can be either a linear or non-linear gradient. The mobile phase can be maintained at a constant or near-constant pH, e.g., a pH of about 3.0, 3.5, 4.0, 4.5, 5.0, 5.5, 6.0, 6.5, 7.0, 7.5, or 8.0. Exemplary column conditions include: an acetonitrile and water mobile phase (e.g., at 10:90, 15:85, 25:75) with an Tetrabutyl ammonium chloride ion pairing reagent (e.g., at 10 mM, 20 mM, 30 mM), and a salt such as NaCl or KCl; a methanol in water mobile phase (e.g., at 10:90, 15:85, 25:75) with a dodecyl trimethyl ammonium hydrogensulfate ion pairing agent (e.g., at 10 mM, 20 mM, 30 mM) and a salt such as NaCl or KCl; an acetonitrile in water mobile phase (e.g., 10:90, 15:85, 25:75) with a Tetrabutyl ammonium bromide ion pairing agent (e.g., at 10 mM, 20 mM, 30 mM) and a salt such as NaCl or KCl; diethyl ether in water mobile phase (e.g., 10:90, 15:85, 25:75) with a Tetraheptyl ammonium bromide ion pairing agent (e.g., at 10 mM, 20 mM, 30 mM) and a salt such as NaCl or KCl; water as a mobile phase with NaCl, KCl or sodium phosphate salt (e.g., at 0.0, 0.1, 1.5M).

The column can be maintained at a constant temperature throughout the separation, e.g., using a commercial column heater. In some embodiments, the column can be maintained at a temperature from about 18° C. to about 70° C., e.g., about 18° C., 20° C., 22° C., 25° C., 30° C., 37° C., 40° C. or 45° C. In some embodiments, the column is at ambient temperature.

Species separated by the methods described herein can be detected by numerous means, e.g., by ultraviolet absorbance (e.g., at a wavelength of about 232 nm), evaporative light scattering, fluorescence, pulsed amperometric detection, and mass spectrometry. In some embodiments, two or more means of detection can be utilized on the same sample, e.g., in series or in parallel.

An internal standard can be used in the methods described herein. When an internal standard is used, it can be separated along with the sample (e.g., mixed or co-injected). Exemplary internal standards include chondroitin/dermatan sulfate derived unsaturated disaccharides, e.g., —U-[1-3]-Gal$_{NAc,4S}$, —U$_{2S}$-[1-3]-Gal$_{NAc,4S}$, —U-[1-3]-Gal$_{NAc4S,6S}$. Other compounds suitable for use as internal standards include adenosine 3',5'-diphosphate sodium salt (PAP), adenosine 3'-monophosphate sodium salt (AMP), and oligonucleotides such as poly-uridines 5'-rUrUrUrUrU-3' (5-mer), 5'-rUrUrUrUrUrU-3' (6-mer), 5'-rUrUrUrUrUrUrUrUrUrUrUrUrUrUrU-3' (15-mer), and 5'-rUrUrUrUrUrUrUrUrUrUrUrUrUrUrUrUrUrUrUrU-3' (20-mer).

Additional information useful for the methods described herein can be found in, e.g., Guo and Conrad (1988) Anal. Biochem., 168:54-62; Murray et al. (1994) Anal. Biochem., 281:177-184; Toyoda et al. (1999) J. Chromatogr. A, 830: 197-201; Kuberan et al. (2002) J. Am. Chem. Soc. 124:8707-8718; and Thanwiroon and Linhardt (2003) J. Chromatogr. A, 1014:215-223, the contents of all of which are incorporated by reference.

Detection

In some embodiments, the amount of a species can be determined, e.g., as a mole % in the sample. For example, a response factor (RF) can be determined for each species, e.g., each species of Table IA. To obtain the RF for each species, known concentrations of standards for each species can be analyzed by HPLC to determine a RF for each. The RFs can then be used to determine the mole % of each species, e.g., each species of Table IA. Mole % can be determined by dividing the weight of each species by the mass to obtain a percent.

In instances where a sample (e.g., a polysaccharide sample such as an enoxaparin preparation) is analyzed using a separation technique such as chromatography (e.g., HPLC), the sample generally elutes off of the device (e.g., column) in peaks. For example, a first component (specie or species) of a sample elutes in a first peak, a second component (specie or species) of a sample elutes in a second peak, etc. In some instances, a sample component is completely resolved, thereby having a first peak corresponding to a first sample component that is completely independent of a second peak corresponding to a second sample component. In some instances, a sample component is not completely resolved, but instead includes one or more components that co-elute or partially overlap with one or more other sample components.

As the sample elutes (e.g., elutes from a column), the eluant is analyzed with a detector (e.g., a UV detector or a light scattering detector) to provide a chromatogram. In embodiments where a polysaccharide sample as described herein (e.g., an UFH sample or an enoxaparin sample, e.g., a digested UFH or enoxaparin sample) is analyzed with a UV detector, the detector is generally set at a wavelength able to detect a double bond moiety, for example a double bond moiety at a non-reducing end of a saccharide species (e.g., a saccharide species generated by enzymatic digestion or a saccharide species from a non-reducing end of enoxaparin sodium chain). For example, a UV detector is generally set to a wavelength from about 220 nm to about 240 nm (e.g., about 232 nm).

Each peak in a chromatogram has a defined area, which can be correlated to the amount (e.g., mass or concentration) of the species or combination of species corresponding to that peak. For example, the peak area for each species (or combination of species) in a chromatogram of a polysaccharide mixture (e.g., an UFH or enoxaparin sample, e.g., a digested UFH or enoxaparin sample) can be directly correlated to the actual mass or concentration of each species (or combination of species) that correspond to the peak being detected. If each species in a sample can be detected by the detector, the total mass of a sample can be accounted for in the chromatogram by a summation of the mass corresponding to each of the peaks in the chromatogram.

The amount of sample (e.g., a species or mixture of species) that corresponds to a peak in a chromatogram is determined by measuring the area under the curve (AUC) of the peak and multiplying the AUC by a factor (e.g., a response factor, molar absorptivity, or extinction coefficient).

In some embodiments, a uniform factor or constant (e.g., a uniform response factor, a uniform molar absorptivity, or a uniform extinction coefficient) is used to determine the amount of one or more species in a mixture. For example, the uniform factor is a multiplier applied as a constant multiplier to all sample peaks being measured for the determination, e.g., all peaks or any peak representing more than a preselected amount, e.g., 0.1% of the total. Such a uniform factor is an estimate of response for the detected components in a mixture, for example based on a weighted average of response of each detected species in the mixture. Thus, when using a uniform factor such as a uniform response factor, uniform molar absorptivity, or uniform extinction coefficient, one can determine the relative amount of species in a sample by comparing the AUC of the peaks in the chromatogram. This comparison is a one to one comparison, because the multiplying factor is the same for each peak. Therefore, a first peak having an AUC of 2× that of a second peak would correspond to a determination of an amount of first species present in 2× the amount of second species, which corresponds to the second peak. The uniform factor can also be used to determine the amount (e.g., mass or concentration) of a single species (or mixture of species) by multiplying the AUC of the corresponding peak by the uniform factor (e.g., uniform response factor or uniform extinction coefficient).

While a uniform factor can be used in methods described herein, it assumes that all species in the sample similarly respond to ultraviolet light. However, for samples such as heparins (e.g., UFH or enoxaparin) all species in the sample do not respond similarly to UV light. Therefore, use of uniform factors can result in significant inaccuracies. Thus, in preferred embodiments, a non uniform factor is used to determine the amount of a one or more species described herein.

In these embodiments, a specific (sometimes referred to herein as unique or non-uniform) response factor, molar absorptivity, or extinction coefficient is used for each of the species (or peaks) being evaluated in a sample (e.g., an UFH or enoxaparin sample, e.g., a digested UFH or enoxaparin sample). For example, a specific response factor, molar absorptivity, or extinction coefficient can be determined for each species or peak identified in a sample or for each peak or species that represents a preselected amount, e.g., 0.1% of the total of the sample. For example, a specific response factor is determined for one or all of the galacturonic acid species, or for all of the galacturonic acid species or peaks representing more than a preselected amount, e.g., 0.1%, of the total in an UFH or enoxaparin sample, e.g., a digested UFH or enoxaparin sample. A specific response factor, molar absorptivity, or extinction coefficient can be determined for a particular peak or fraction which contains more than one species. Methods which use specific response factors are referred to herein as non-uniform methods.

A response factor, molar absorptivity, or extinction coefficient for a species can be determined by preparing a standard curve for the species (i.e., measuring the response of a detector (e.g., a UV detector) to the species at a plurality of known concentrations (e.g., three or more different known concentrations)). A standard curve can be prepared, for example, by evaluating the concentration of a plurality of samples using a reliable method, for example a carbazole assay can be used to determine the concentration of a saccharide species. In some embodiments, each measurement is taken multiple times to provide improved accuracy (e.g., each measurement is taken in triplicate or more with the response averaged among the three or more measurements). With the plurality of observed data points, a linear curve can be plotted, providing the constant corresponding to the response for that species.

This same procedure can be used for peaks correlating to a plurality of species (e.g., unresolved peaks that correlate to two or more species in a mixture). For example, in instances where a peak is unresolved and correlates to two or more species, the plurality of species can be evaluated together to provide a measured constant that corresponds to the response of the mixture of species in the unresolved peak.

In contrast with the example of a uniform factor described above, non-uniform methods (e.g., methods which use a factor that is specific for a species or peak in a sample (e.g., a galacturonic acid species), a first peak having an AUC of 2× that of a second peak would not necessarily correspond to a determination of an amount of first species present in 2× the amount of second species. Because the species will each have a multiplier that is uniquely determined, the first peak will have an amount of 2× multiplied by the specific factor for the species corresponding to the first peak, and the second peak will have an amount of X multiplied by the specific factor for the species corresponding to the second peak. In some embodiments, a specific factor may have been determined, for example, for the first peak but not the second peak. In this instance, the amount corresponding to the first peak will be determined by multiplying the AUC of first peak by the specific factor (e.g., a specific response factor, molar absorptivity, or extinction coefficient) and the amount corresponding to the second peak will be determined by multiplying the AUC of the second peak by a non-specific factor (a uniform factor). Although certainly more accurate and more desirable than a uniform method, this method is still less desirable than one which uses a specific factor for each species or peak measured.

Use of non-uniform response factors provide a more accurate determination of the amount of one or more species in a sample because the AUC of the peak corresponding to that species (or in some cases peak) is multiplied by a factor that is determined by the response of that species alone, as opposed to a weighted average of all species being measured by the detector. Since various species within a polysaccharide mixture can have an effect, e.g., on activity or other parameters of the mixture, it can be important to accurately depict the amount of such species in the mixture.

In some embodiments, one or more species is isolated and/or purified prior to determining the specific factor or constant (e.g., response factor, molar absorptivity, or extinction coefficient) for that species. For example, a polysaccharide sample is completely digested and one or more individual species are separated, identified and evaluated to determine the degree of purity of one or more species prior to determining the unique factor corresponding to a species. In some embodiments, an UFH or enoxaparin sample is completely digested, e.g., using chemical and/or enzymatic means such as an enzymatic digestion described herein. In some embodiments, the identity of one or more species are conclusively determined using one or a combination of analytical and chemical methods (e.g., MS, HPLC, CE, LC-MS, etc.).

In some embodiments, a specific factor or constant is used to determine the amount (relative or absolute) and/or distribution of one or more species in a polysaccharide sample such as UFH or enoxaparin (e.g., an enzymatically digested e.g., incompletely or, preferably, completely digested UFH or enoxaparin). For example, a specific factor or constant such as a specific response factor, molar absorptivity, or extinction coefficient is determined for one or more galacturonic acid species present in the polysaccharide mixture (e.g., each galacturonic acid species detected in the sample). For example, a UV response factor at 232 nm is determined for one or more galacturonic acid species present in the polysaccharide sample (e.g., a specific response factor is determined for 1, 2 or 3 of the galacturonic acid species present in an amount of more than 0.1 mole %).

In some embodiments, a specific factor or constant is determined for a subset of species in the sample, e.g., a UFH or enoxaparin sample. In some embodiments, the subset of species includes any of the subsets described herein. The amount (relative or absolute) and/or distribution of one or more of the species can be determined using specific factors determined for each of the species (or peaks). For example, the total amount of galacturonic acid species can be determined by determining the AUC for each of the galacturonic acid species, multiplying the AUC for each of the galacturonic acid species by a factor specifically determined it, and adding together the amounts for each of the galacturonic acid species, thereby determining the total amount of galacturonic acid species in the sample. In some embodiments, the relative amount of galacturonic acid species in the sample as a whole can be determined by dividing the total amount of galacturonic acid species as determined above, by the total weight of the sample (e.g., the weight of the sample as injected onto an HPLC column).

Where a uniform factor or constant is used to determine the relative amount of galacturonic acid species in a sample, the AUC of the peaks corresponding to the galacturonic acid species is added together to provide a total amount of galacturonic acid species, and the total galacturonic acid species is divided by the total amount of sample, which can be determined by summation of the AUC for all of the peaks corresponding to sample species or by an empirical determination of sample amount, such as a weighing of the sample put on the analytical device.

It is generally more accurate to determine the total relative amount of a species in a sample using a non-uniform factor or constant. The AUC for each of the peaks corresponding to galacturonic acid species is multiplied by a factor unique to that galacturonic acid species, and amounts determined for each of the peaks is summarized to provide a total amount of galacturonic acid species in the sample. The relative amount can then be determined by dividing the total amount of galacturonic acid species by the total amount of species in the sample. The total amount of species in the sample can also be determined by using a specific factor or constant for each species present in the mixture. In this case, the total number of galacturonic acid species is divided by a summation of the AUC for all peaks in the mixture where the AUC for each peak in the mixture has been multiplied by a specific factor (e.g., a specific response factor).

Galacturonic acid is used as an example in the sections described above. However, other subsets of species such as those described in Table ID, can also be determined by the methods described above.

Table II below provides non-uniform response factors (RRF) for species present in enoxaparin samples (a subset of which are also present in UFH.

| Peak # | Identity | RRF | Comment on building blocks |
|---|---|---|---|
| 1 | ΔUH$_{NAc}$ | 1.33 | Natural |
| 2^ | Linkage region isomer | 0.31 | Natural |
| 3^ | ΔUGalGalXyl-O—CH$_2$—COOH | 0.31 | Natural |
| 4* | ΔU$_{gal}$H$_{NS}$ | 0.93 | Modified |
| 5 | ΔUH$_{NS}$ (α) | 1.91 | Natural |
| 6 | ΔUH$_{NS}$ (β) | 1.91 | Natural |
| 7 | ΔUH$_{NS}$ (1,6 anhydro) | 1.91 | Modified |
| 8 | ΔUMan$_{NS}$ (1,6 anhydro) | 1.47 | Modified |
| 9 | ΔUH$_{NAc6S}$ | 1.08 | Natural |
| 10 | ΔU$_{2S}$H$_{NAc}$ (α) | 1.12 | Natural |
| 11 | ΔU$_{2S}$H$_{NAc}$ (β) | 1.12 | Natural |
| 12# | ΔUH$_{NS3S}$ | 1.18 | Natural |
| 13 | ΔUH$_{NS6S}$ (α) | 1.18 | Natural |
| 14* | ΔU$_{gal}$H$_{NS6S}$ (α) | 1.16 | Modified |
| 15* | ΔU$_{gal}$H$_{NS6S}$ (β) | 1.16 | Modified |
| 16 | ΔUH$_{NS6S}$ (β) | 1.18 | Natural |
| 17 | ΔU$_{2S}$H$_{NS}$ (α) | 1.04 | Natural |
| 18 | ΔU$_{2S}$H$_{NS}$ ( (β) | 1.04 | Natural |
| 19 | ΔU$_{2S}$H$_{NS}$ (1,6 anhydro) | 1.04 | Modified |
| 20 | ΔU$_{2S}$Man$_{NS}$ (1,6 anhydro) | 0.80 | Modified |
| 21 | ΔU$_{2S}$H$_{NAc6S}$ (α) | 1.17 | Natural |
| 22 | ΔU$_{2S}$H$_{NAc6S}$ (β) | 1.17 | Natural |
| 23# | ΔU$_{2S}$Man$_{NAc6S}$ | 0.90 | Modified |
| 24 | ΔUHN$_{Ac6S}$GH$_{NS,3S}$ (α) | 0.28 | Natural |
| 25 | ΔUHN$_{Ac6S}$GH$_{NS,3S}$ (β) | 0.28 | Natural |
| 26 | ΔU$_{2S}$Man$_{NS6S}$ (α) | 0.77 | Modified |
| 27 | ΔU$_{2S}$H$_{NS6S}$ (α) | 1.00 | Natural |
| 28 | ΔUH$_{NAc6S}$GH$_{NS,3S,6S}$ (α) | 0.38 | Anti-Xa Activity |
| 29 | ΔU$_{2S}$H$_{NS6S}$ (β) | 1.00 | Natural |
| 30 | ΔU$_{2S}$H$_{NS6S}$I$_{2S}$ (α) | 0.36 | Modified |
| 31 | ΔU$_{2S}$H$_{NS6S}$I$_{2S}$ (β) | 0.36 | Modified |
| 32 | ΔUH$_{NS6S}$GH$_{NS3S6S}$ (α) | 0.17 | Natural |
| 33 | ΔUH$_{NS6S}$GH$_{NS3S6S}$ (β) | 0.17 | Natural |
| 34 | ΔU$_{2S}$H$_{NS6S}$I$_{2S}$H$_{NS}$ (1,6 anhydro) | 0.14 | Modified |
| 35 | ΔU$_{2S}$H$_{NS3S6S}$ | 0.53 | Natural |
| 36 | ΔU$_{2S}$H$_{NS6S}$I$_{2S}$Man$_{NS}$ (1,6 anhydro) | 0.11 | Modified |
| 37 | ΔU$_{2S}$H$_{NS6S}$GH$_{NS3S6S}$ (β) | 0.12 | Natural |
| 38 | ΔU$_{2S}$H$_{NS6S}$GH$_{NS3S6S}$ (α) | 0.12 | Natural |

Table III below provides amounts of species present in a digested enoxaparin mixture as calculated using non-uniform response factors.

| Peak | Area-% | RRF | Molecular Weight | Mole Fraction | Mole-% |
|---|---|---|---|---|---|
| 1 | 1.80 | 1.33 | 401 | 3.4E-03 | 1.9 |
| 2 | 0.03 | 0.31 | 741 | 1.2E-04 | 0.1 |
| 3 | 1.31 | 0.31 | 741 | 5.7E-03 | 3.3 |
| 4 | 0.31 | 0.93 | 461 | 7.2E-04 | 0.4 |
| 5 | 2.58 | 1.91 | 461 | 2.9E-03 | 1.7 |
| 6 | 0.48 | 1.91 | 461 | 5.5E-04 | 0.3 |
| 7 | 0.35 | 1.91 | 443 | 4.1E-04 | 0.2 |
| 8 | 0.45 | 1.47 | 443 | 6.9E-04 | 0.4 |
| 9 | 3.38 | 1.08 | 503 | 6.2E-03 | 3.6 |
| 10 | 0.67 | 1.12 | 503 | 1.2E-03 | 0.7 |
| 11 | 1.19 | 1.12 | 503 | 2.1E-03 | 1.2 |
| 12 | 0.11 | 1.18 | 563 | 1.6E-04 | 0.1 |
| 13 | 9.11 | 1.18 | 563 | 1.4E-02 | 8.0 |
| 14 | 1.24 | 1.16 | 563 | 1.9E-03 | 1.1 |
| 15 | 0.13 | 1.16 | 563 | 2.0E-04 | 0.1 |
| 16 | 0.84 | 1.18 | 563 | 1.3E-03 | 0.7 |
| 17 | 5.76 | 1.04 | 563 | 9.8E-03 | 5.7 |
| 18 | 1.01 | 1.04 | 563 | 1.7E-03 | 1.0 |
| 19 | 1.54 | 1.04 | 545 | 2.7E-03 | 1.6 |
| 20 | 0.11 | 0.80 | 545 | 2.5E-04 | 0.1 |
| 21 | 0.72 | 1.17 | 605 | 1.0E-03 | 0.6 |
| 22 | 1.14 | 1.17 | 605 | 1.6E-03 | 0.9 |
| 23 | 0.09 | 0.90 | 605 | 1.7E-04 | 0.1 |
| 24 | 0.40 | 0.28 | 1066 | 1.3E-03 | 0.8 |
| 25 | 0.12 | 0.28 | 1066 | 4.2E-04 | 0.2 |
| 26 | 1.81 | 0.77 | 665 | 3.5E-03 | 2.0 |
| 27 | 51.22 | 21.00 | 665 | 7.7E-02 | 44.5 |
| 28 | 2.63 | 0.38 | 1168 | 6.0E-03 | 3.5 |
| 29 | 6.18 | 1.00 | 665 | 9.3E-03 | 5.4 |
| 30 | 0.49 | 0.36 | 965 | 1.4E-03 | 0.8 |
| 31 | 0.75 | 0.36 | 965 | 2.2E-03 | 1.2 |
| 32 | 0.25 | 0.17 | 1228 | 1.2E-03 | 0.7 |
| 33 | 0.18 | 0.17 | 1228 | 8.8E-04 | 0.5 |
| 34 | 0.04 | 0.14 | 1210 | 2.2E-04 | 0.1 |
| 35 | 0.17 | 0.53 | 767 | 4.3E-04 | 0.2 |
| 36 | 1.13 | 0.11 | 1210 | 8.6E-03 | 5.0 |
| 37 | 0.12 | 0.12 | 1330 | 8.0E-04 | 0.5 |
| 38 | 0.17 | 0.12 | 1330 | 1.1E-03 | 0.6 |
| Sum | 100.0 | NA | N/A | 1.7E-01 | 100.0 |

Table IV below provides amounts of species present in a digested UFH mixture as calculated using non-uniform response factors.

| Peak | RRF | Molecular Weight | Area-% | Mole Fraction | Mole-% |
|---|---|---|---|---|---|
| 1 | 1.33 | 401 | 3.84 | 7.18E-03 | 4.5 |
| 2 | 0.31 | 741 | 0.04 | 1.87E-04 | 0.1 |
| 3 | 0.31 | 741 | 0.31 | 1.33E-03 | 0.8 |
| 4 | 0.93 | 461 | 0.22 | 5.09E-04 | 0.3 |
| 5 | 1.91 | 461 | 2.55 | 2.90E-03 | 1.8 |
| 6 | 1.91 | 461 | 0.36 | 4.11E-04 | 0.3 |
| 7 | 1.91 | 443 | 0.00 | 0.00E+00 | 0.0 |
| 8 | 1.47 | 443 | 0.00 | 0.00E+00 | 0.0 |
| 9 | 1.08 | 503 | 4.32 | 7.94E-03 | 4.9 |
| 10 | 1.12 | 503 | 0.64 | 1.14E-03 | 0.7 |
| 11 | 1.12 | 503 | 0.97 | 1.73E-03 | 1.1 |
| 12 | 1.18 | 563 | 0.17 | 2.58E-04 | 0.2 |
| 13 | 1.18 | 563 | 10.69 | 1.62E-02 | 10.0 |
| 14 | 1.16 | 563 | 1.60 | 2.46E-03 | 1.5 |
| 15 | 1.16 | 563 | 0.16 | 2.44E-04 | 0.2 |
| 16 | 1.18 | 563 | 1.11 | 1.68E-03 | 1.0 |
| 17 | 1.04 | 563 | 5.48 | 9.33E-03 | 5.8 |
| 18 | 1.04 | 563 | 0.77 | 1.30E-03 | 0.8 |
| 19 | 1.04 | 545 | 0.00 | 0.00E+00 | 0.0 |
| 20 | 0.80 | 545 | 0.00 | 0.00E+00 | 0.0 |
| 21 | 1.17 | 605 | 0.67 | 9.44E-04 | 0.6 |
| 22 | 1.17 | 605 | 1.03 | 1.46E-03 | 0.9 |
| 23 | 0.90 | 605 | 0.00 | 0.00E+00 | 0.0 |
| 24 | 0.28 | 1066 | 0.37 | 1.23E-03 | 0.8 |
| 25 | 0.28 | 1066 | 0.04 | 2.38E-04 | 0.1 |
| 26 | 0.77 | 665 | 0.00 | 0.00E+00 | 0.0 |
| 27 | 1.00 | 665 | 54.64 | 8.22E-025 | 1.0 |
| 28 | 0.38 | 1168 | 2.81 | 6.40E-03 | 4.0 |
| 29 | 1.00 | 665 | 6.28 | 9.44E-03 | 5.9 |
| 30 | 0.36 | 965 | 0.00 | 0.00E+00 | 0.0 |
| 31 | 0.36 | 965 | 0.03 | 8.65E-05 | 0.1 |
| 32 | 0.17 | 1228 | 0.24 | 1.16E-03 | 0.7 |
| 33 | 0.17 | 1228 | 0.17 | 8.07E-04 | 0.5 |
| 34 | 0.14 | 1210 | 0.00 | 0.00E+00 | 0.0 |
| 35 | 0.53 | 767 | 0.21 | 5.18E-04 | 0.3 |
| 36 | 0.11 | 1210 | 0.00 | 0.00E+00 | 0.0 |
| 37 | 0.12 | 1330 | 0.13 | 8.46E-04 | 0.5 |
| 38 | 0.12 | 1330 | 0.15 | 1.00E-03 | 0.6 |
| Sum | N/A | N/A | 100% | 1.61E-01 | 100% |

EXAMPLE 1

Isolation of Standards for Response Factor Calculation 400 mg of enoxaparin was digested using an enzyme cocktail consisting of Heparinase I (120 mIU/mg), Heparinase II (220 mIU/mg) and Heparinase III (120 mIU/mg). This digestion was performed at 30° C. for 16 hrs. The resulting solution was passed through a 1 ml nickel chelating Hitrap column to remove the enzyme. The ion-pairing RPHPLC method was modified for the purpose of peak isolation and characterization. Separation was performed using two different Supelco C$_{18}$ Discovery columns: a 5 µm, 250×21.1 mm column at a flow rate of 6.0 ml/min (250 minutes total run time) or a 5 µm, 220×10 mm) at a flow rate of 3.3 ml/min (130 minutes of total run time). These different column dimensions were chosen based on the chromatographic region of specific interest that required separation. In both cases, mobile phase A: 15% ACN, 20 mM TBA, pH 7.0 and mobile phase B: 15% ACN, 1.0 M NaCl, pH 7.0. After isolation, each fraction was lyophilized and then buffer exchanged into 50 mM ammonium acetate to remove sodium chloride and tetrabutyl ammonium chloride. Based on the volume and concentration of the fraction to be exchanged, different types and dimensions of buffer exchange columns were applied. Superdex Peptide (30×1.0 cm) or Superdex-30 at two different dimensions (59×1.0 cm) and (59×1.6 cm) were used.

Structural identification was made by a combination of CE composition, mass spectrometry and NMR.

EXAMPLE 2

Analysis of Enoxaparin Sodium

A sample of enoxaparin is isolated by lyophilization, dried in a vacuum oven (49° C., 6 h), and then reconstituted in water at a concentration of 100 mg/mL. This solution is further diluted and then 1.2 mg substrate was digested using an enzyme cocktail consisting of heparinases I (500 mIU), II (400 mIU), and III (500 mIU) in 25 mM sodium acetate, 1 mM calcium acetate pH 7.0. This digestion, termed "Digest A", is performed at 30° C. for 16 hr. The resulting solution is passed through a Ni$^{++}$ spin column to remove enzyme and the resulting solution is analyzed by ion pairing RPHPLC using tetra-n-butylammonium chloride (TBA) as the ion pair reagent in an acetonitrile (ACN), water, and NaCl buffer at pH 7.0 (Mobile Phase A: 15% ACN, 30 mM TBA; Mobile Phase B: 15% ACN, 30 mM TBA, 1 M NaCl). The samples are held at 4° C. during analysis and 45 µL of sample is injected onto the column. The sample is separated using a C18 Discovery column (5 µm, 4.6×250 mm) at 25° C. at a flow rate of 0.7 mL/min over 106 min of total run time.

In addition to digest #1, two additional digests are completed. The first is a further digestion of the heparinase-treated sample with the 2-O sulfatase from *Flavobacterium heparinum*. In this case 1 IU/mg of 2-O sulfatase is added to the reaction mixture and allowed to act for 6 hrs at 30° C. The second digest involves the addition of both the 2-O sulfatase (1 IU/mg) and the Δ$^{4,5}$ glycuronidase (1 IU/mg) for 6 hrs at 30° C.

EXAMPLE 3

Analysis of an Unfractionated Heparin

A sample of UFH is isolated by lyophilization, dried in a vacuum oven (49° C., 6 h), and then reconstituted in water at a concentration of 100 mg/mL. This solution is further diluted and then 1.2 mg substrate was digested using an enzyme cocktail consisting of heparinases I (500 mIU), II (400 mIU), and III (500 mIU) in 25 mM sodium acetate, 1 mM calcium acetate pH 7.0. This digestion, termed "Digest A", is performed at 30° C. for 16 hr. The resulting solution is passed through a Ni$^{++}$ spin column to remove enzyme and the resulting solution is analyzed by ion pairing RPHPLC using tetra-n-butylammonium chloride (TBA) as the ion pair reagent in an acetonitrile (ACN), water, and NaCl buffer at pH 7.0 (Mobile Phase A: 15% ACN, 30 mM TBA; Mobile Phase B: 15% ACN, 30 mM TBA, 1 M NaCl). The samples are held at 4° C. during analysis and 45 µL of sample is injected onto the column. The sample is separated using a C18 Discovery column (5 µm, 4.6×250 mm) at 25° C. at a flow rate of 0.7 mL/min over 106 min of total run time.

In addition to digest #1, two additional digests are completed. The first is a further digestion of the heparinase-treated sample with the 2-O sulfatase from *Flavobacterium heparinum*. In this case 1 IU/mg of 2-O sulfatase is added to the reaction mixture and allowed to act for 6 hrs at 30° C. The second digest involves the addition of both the 2-O sulfatase (1 IU/mg) and the Δ$^{4,5}$ glycuronidase (1 IU/mg) for 6 hrs at 30° C.

EXAMPLE 4

Response Factor Calculation

The concentration of each standard was determined using a carbazole assay that determines the total amount of saccharide species present in the sample solution. Then the concentration was corrected based on the purity results for each standard as determined by combination of techniques CE, RPHPLC, LC-MS. The response factors for anomers (α- and β-isomers) that are expected to be equal were calculated as an anomeric mixture. The response factors (see table II) were measured based on a three point standard curve bracketing the concentrations typically seen in enoxaparin digests based on area-% levels. The relative Response Factors (RRF) were calculated vs. the main disaccharide peak ΔU$_{2S}$H$_{NS,6S}$. Each available standard component was injected individually and the response factor at each concentration was calculated based on the following:

RF=Area (µV*sec)/(concentration (mg/mL)*purity factor)

The references, patents and patent applications cited herein are incorporated by reference. Modifications and variations of these methods and products thereof will be obvious to those skilled in the art from the foregoing detailed description and are intended to be encompassed within the scope of the appended claims.

What is claimed is:

1. A method of processing a low molecular weight heparin (LMWH) preparation, the method comprising:
   digesting the LMWH preparation with a heparinase I, a heparinase II, a heparinase III, a 2-O-sulfatase, and a Δ4,5 glycuronidase;
   providing a determination made using reverse phase high performance liquid chromatography (RP-HPLC), of whether all the structural moieties of the following first table:

| Peak # | Identity | Comment on building blocks |
|---|---|---|
| 1 | ΔUH$_{NAc}$ | Natural |
| 2 | Linkage region isomer | Natural |
| 3 | ΔUGalGalXyl-O—CH$_2$—COOH | Natural |
| 4 | ΔU$_{gal}$H$_{NS}$ | Modified |
| 5 | ΔUH$_{NS}$ (α) | Natural |
| 6 | ΔUH$_{NS}$ (β) | Natural |
| 7 | ΔUH$_{NS}$ (1,6 anhydro) | Modified |
| 8 | ΔUMan$_{NS}$ (1,6 anhydro) | Modified |
| 9 | ΔUH$_{NAc6S}$ | Natural |
| 10 | ΔU$_{2S}$H$_{NAc}$ (α) | Natural |
| 11 | ΔU$_{2S}$H$_{NAc}$ (β) | Natural |

-continued

| Peak # | Identity | Comment on building blocks |
|---|---|---|
| 12 | $\Delta UH_{NS3S}$ | Natural |
| 13 | $\Delta UH_{NS6S}$ ($\alpha$) | Natural |
| 14 | $\Delta U_{gal}H_{NS6S}$ ($\alpha$) | Modified |
| 15 | $\Delta U_{gal}H_{NS6S}$ ($\beta$) | Modified |
| 16 | $\Delta UH_{NS6S}$ ($\beta$) | Natural |
| 17 | $\Delta U_{2S}H_{NS}$ ($\alpha$) | Natural |
| 18 | $\Delta U_{2S}H_{NS}$ ($\beta$) | Natural |
| 19 | $\Delta U_{2S}H_{NS}$ (1,6 anhydro) | Modified |
| 20 | $\Delta U_{2S}Man_{NS}$ (1,6 anhydro) | Modified |
| 21 | $\Delta U_{2S}H_{NAc6S}$ ($\alpha$) | Natural |
| 22 | $\Delta U_{2S}H_{NAc6S}$ ($\beta$) | Natural |
| 23 | $\Delta U_{2S}Man_{NAc6S}$ | Modified |
| 24 | $\Delta UHN_{Ac6S}GH_{NS,3S}$ ($\alpha$) | Natural |
| 25 | $\Delta UHN_{Ac6S}GH_{NS,3S}$ ($\beta$) | Natural |
| 26 | $\Delta U_{2S}Man_{NS6S}$ ($\alpha$) | Modified |
| 27 | $\Delta U_{2S}H_{NS6S}$ ($\alpha$) | Natural |
| 28 | $\Delta UH_{NAc6S}GH_{NS,3S,6S}$ ($\alpha$) | Natural |
| 29 | $\Delta U_{2S}H_{NS6S}$ ($\beta$) | Natural |
| 30 | $\Delta U_{2S}H_{NS6S}I_{2S}$ ($\alpha$) | Modified |
| 31 | $\Delta U_{2S}H_{NS6S}I_{2S}$ ($\beta$) | Modified |
| 32 | $\Delta UH_{NS6S}GH_{NS3S6S}$ ($\alpha$) | Natural |
| 33 | $\Delta UH_{NS6S}GH_{NS3S6S}$ ($\beta$) | Natural |
| 34 | $\Delta U_{2S}H_{NS6S}I_{2S}H_{NS}$ (1,6 anhydro) | Modified |
| 35 | $\Delta U_{2S}H_{NS3S6S}$ | Natural |
| 36 | $\Delta U_{2S}H_{NS6S}I_{2S}Man_{NS}$ (1,6 anhydro) | Modified |
| 37 | $\Delta U_{2S}H_{NS6S}GH_{NS3S6S}$ ($\beta$) | Natural |
| 38 | $\Delta U_{2S}H_{NS6S}GH_{NS3S6S}$ ($\alpha$) | Natural | are present in the preparation in an amount which falls within Range A (mole %) of the following second table:

| Peak # | Identity | Range A (mole %) | |
|---|---|---|---|
| 1 | $\Delta UH_{NAc}$ | 1.1 | 2.4 |
| 2 | Linkage region isomer | 0.0 | 0.4 |
| 3 | $\Delta UGalGalXyl-O—CH_2—COOH$ | 0.4 | 4.7 |
| 4 | $\Delta U_{gal}H_{NS}$ | 0.0 | 0.7 |
| 5 | $\Delta UH_{NS}$ ($\alpha$) | 1.6 | 2.0 |
| 6 | $\Delta UH_{NS}$ ($\beta$) | 0.3 | 0.4 |
| 7 | $\Delta UH_{NS}$ (1,6 anhydro) | 0.2 | 0.3 |
| 8 | $\Delta UMan_{NS}$ (1,6 anhydro) | 0.3 | 0.5 |
| 9 | $\Delta UH_{NAc6S}$ | 3.1 | 4.2 |
| 10 | $\Delta U_{2S}H_{NAc}$ ($\alpha$) | 0.4 | 0.9 |
| 11 | $\Delta U_{2S}H_{NAc}$ ($\beta$) | 1.0 | 1.5 |
| 12 | $\Delta UH_{NS3S}$ | 0.0 | 0.5 |
| 13 + 14 | $\Delta UH_{NS6S}$ ($\alpha$) + $\Delta U_{gal}H_{NS6S}$ ($\alpha$) | 7.4 | 10.6 |
| 15 + 16 | $\Delta U_{gal}H_{NS6S}$ ($\beta$) + $\Delta UH_{NS6S}$ ($\beta$) | 0.6 | 1.1 |
| 17 | $\Delta U_{2S}H_{NS}$ ($\alpha$) | 5.4 | 6.4 |
| 18 | $\Delta U_{2S}H_{NS}$ ($\beta$) | 0.6 | 1.2 |
| 19 | $\Delta U_{2S}H_{NS}$ (1,6 anhydro) | 1.4 | 1.7 |
| 20 | $\Delta U_{2S}Man_{NS}$ (1,6 anhydro) | 0.0 | 0.3 |
| 21 | $\Delta U_{2S}H_{NAc6S}$ ($\alpha$) | 0.4 | 0.7 |
| 22 | $\Delta U_{2S}H_{NAc6S}$ ($\beta$) | 0.8 | 1.1 |
| 23 | $\Delta U_{2S}Man_{NAc6S}$ | 0.0 | 0.2 |
| 24 | $\Delta UHN_{Ac6S}GH_{NS,3S}$ ($\alpha$) | 0.5 | 1.1 |
| 25 | $\Delta UHN_{Ac6S}GH_{NS,3S}$ ($\beta$) | 0.1 | 0.3 |
| 26 | $\Delta U_{2S}Man_{NS6S}$ ($\alpha$) | 1.5 | 2.5 |
| 27 | $\Delta U_{2S}H_{NS6S}$ ($\alpha$) | 43.4 | 47.4 |
| 28 | $\Delta UH_{NAc6S}GH_{NS,3S,6S}$ ($\alpha$) | 2.1 | 4.5 |
| 29 | $\Delta U_{2S}H_{NS6S}$ ($\beta$) | 4.5 | 6.7 |
| 30 | $\Delta U_{2S}H_{NS6S}I_{2S}$ ($\alpha$) | 0.5 | 1.0 |
| 31 | $\Delta U_{2S}H_{NS6S}I_{2S}$ ($\beta$) | 0.9 | 1.6 |
| 32 | $\Delta UH_{NS6S}GH_{NS3S6S}$ ($\alpha$) | 0.2 | 0.9 |
| 33 | $\Delta UH_{NS6S}GH_{NS3S6S}$ ($\beta$) | 0.1 | 0.7 |
| 34 | $\Delta U_{2S}H_{NS6S}I_{2S}H_{NS}$ (1,6 anhydro) | 0.0 | 0.6 |
| 35 | $\Delta U_{2S}H_{NS3S6S}$ | 0.1 | 0.4 |
| 36 | $\Delta U_{2S}H_{NS6S}I_{2S}Man_{NS}$ (1,6 anhydro) | 4.5 | 5.7 |
| 37 | $\Delta U_{2S}H_{NS6S}GH_{NS3S6S}$ ($\beta$) | 0.2 | 0.6 |
| 38 | $\Delta U_{2S}H_{NS6S}GH_{NS3S6S}$ ($\alpha$) | 0.4 | 0.7 | and if said structural moieties are present in an amount that falls within Range A of the second table, then processing the LMWH preparation by a process selected from the group consisting of: classifying, selecting, accepting, releasing, shipping, formulating, labeling, and packaging, the LMWH preparation.

2. A method of processing an unfractionated heparin (UFH) preparation, the method comprising:
 digesting the preparation with a heparinase I, a heparinase II, a heparinase III, a 2-O-sulfatase, and a $\Delta 4,5$ glycuronidase;
 providing a determination made using reverse phase high performance liquid chromatography (RP-HPLC), of whether all of the structural moieties of the following table are present in the preparation in an amount which falls within a Range (mole %) provided in the following table:

| Peak # | Identity | Range A (mole %) | | Range B (mole %) | | Range C (mole %) | | Range D (mole %) | | Range E (mole %) | |
|---|---|---|---|---|---|---|---|---|---|---|---|
| 1 | $\Delta UH_{NAc}$ | 2.0 | 6.0 | 3.5 | 5.5 | 4.0 | 6.5 | 3.0 | 4.5 | 3.8 | 4.3 |
| 2 | Linkage region isomer | 0.00 | 0.5 | 0.00 | 0.00 | 0.00 | 0.05 | 0.00 | 0.1 | <0.2 | |
| 3 | $\Delta UGalGalXyl-O—CH_2—COOH$ | 0.2 | 1.0 | 0.3 | 1.4 | 0.5 | 2.0 | 0.1 | 0.8 | 0.3 | 1.8 |
| 4 | $\Delta U_{gal}H_{NS}$ | 0.2 | 1.0 | 0.2 | 0.6 | 0.1 | 0.4 | 0.2 | 0.4 | 0.1 | 0.8 |
| 5 | $\Delta UH_{NS}$ ($\alpha$) | 1.0 | 3.0 | 0.8 | 1.5 | 1.2 | 1.4 | 1.0 | 1.5 | 0.5 | 3.5 |
| 6 | $\Delta UH_{NS}$ ($\beta$) | 0.1 | 0.6 | 0.05 | 0.5 | 0.05 | 0.3 | 0.05 | 0.7 | 0.1 | 0.3 |
| 7 | $\Delta UH_{NS}$ (1,6 anhydro) | 0.00 | 0.5 | 0.00 | 0.00 | 0.00 | 0.05 | 0.00 | 0.1 | <0.2 | |
| 8 | $\Delta UMan_{NS}$ (1,6 anhydro) | 0.00 | 0.5 | 0.00 | 0.00 | 0.00 | 0.05 | 0.00 | 0.1 | <0.2 | |
| 9 | $\Delta UH_{NAc6S}$ | 4.0 | 6.0 | 4.8 | 6.2 | 4.2 | 5.5 | 4.6 | 5.2 | 4.2 | 5.8 |
| 10 | $\Delta U_{2S}H_{NAc}$ ($\alpha$) | 0.3 | 0.8 | 0.2 | 0.8 | 0.6 | 1.2 | 0.2 | 0.9 | 0.4 | 0.9 |
| 11 | $\Delta U_{2S}H_{NAc}$ ($\beta$) | 0.9 | 1.4 | 0.6 | 1.3 | 1.0 | 1.5 | 0.5 | 1.7 | 0.8 | 1.7 |
| 12 | $\Delta UH_{NS3S}$ | 0.05 | 0.5 | 0.00 | 0.3 | 0.05 | 0.5 | 0.00 | 0.3 | <0.5 | |
| 13 | $\Delta UH_{NS6S}$ ($\alpha$) | 9.0 | 11.0 | 9.8 | 12.2 | 8.8 | 10.2 | 10.0 | 10.3 | 9.5 | 11.5 |
| 14 | $\Delta U_{gal}H_{NS6S}$ ($\alpha$) | 1.0 | 3.0 | 2.0 | 4.0 | 2.0 | 5.0 | 1.0 | 2.8 | 2.0 | 2.5 |
| 15 | $\Delta U_{gal}H_{NS6S}$ ($\beta$) | 0.1 | 0.5 | 0.2 | 0.6 | 0.1 | 0.4 | 0.2 | 0.4 | 0.05 | 1.0 |
| 16 | $\Delta UH_{NS6S}$ ($\beta$) | 0.00 | 2.0 | 0.5 | 1.5 | 0.8 | 1.5 | 0.5 | 1.2 | 0.8 | 1.2 |
| 17 | $\Delta U_{2S}H_{NS}$ ($\alpha$) | 3.1 | 7.3 | 5.1 | 6.2 | 3.6 | 8.5 | 5.8 | 8.5 | 4.2 | 6.4 |
| 18 | $\Delta U_{2S}H_{NS}$ ($\beta$) | 0.4 | 1.0 | 0.7 | 1.0 | 0.5 | 1.2 | 0.4 | 1.3 | 0.6 | 1.3 |
| 19 | $\Delta U_{2S}H_{NS}$ (1,6 anhydro) | 0.00 | 0.5 | 0.00 | 0.00 | 0.00 | 0.05 | 0.00 | 0.1 | <0.2 | |
| 20 | $\Delta U_{2S}Man_{NS}$ (1,6 anhydro) | 0.00 | 0.5 | 0.00 | 0.00 | 0.00 | 0.05 | 0.00 | 0.1 | <0.2 | |
| 21 | $\Delta U_{2S}H_{NAc6S}$ ($\alpha$) | 0.4 | 0.8 | 0.1 | 1.0 | 0.5 | 1.2 | 0.4 | 0.9 | 0.4 | 1.0 |
| 22 | $\Delta U_{2S}H_{NAc6S}$ ($\beta$) | 0.9 | 1.2 | 0.8 | 1.7 | 0.6 | 1.4 | 0.6 | 1.2 | 0.8 | 1.5 |

-continued

| Peak # | Identity | Range A (mole %) | | Range B (mole %) | | Range C (mole %) | | Range D (mole %) | | Range E (mole %) | |
|---|---|---|---|---|---|---|---|---|---|---|---|
| 23 | $\Delta U_{2S}Man_{NAc,6S}$ | 0.00 | 0.5 | 0.00 | 0.00 | 0.00 | 0.05 | 0.00 | 0.1 | <0.2 | |
| 24 | $\Delta UHN_{Ac6S}GH_{NS,3S}$ ($\alpha$) | 0.8 | 1.4 | 0.2 | 2.0 | 1.0 | 2.5 | 0.05 | 1.2 | 0.5 | 1.5 |
| 25 | $\Delta UHN_{Ac6S}GH_{NS,3S}$ ($\beta$) | 0.00 | 0.5 | 0.00 | 0.00 | 0.00 | 0.05 | 0.00 | 0.1 | <0.2 | |
| 26 | $\Delta U_{2S}Man_{NS6S}$ ($\alpha$) | 0.00 | 0.5 | 0.00 | 0.00 | 0.00 | 0.05 | 0.00 | 0.1 | <0.2 | |
| 27 | $\Delta U_{2S}H_{NS6S}$ ($\alpha$) | 50 | 53 | 50.5 | 60.5 | 48 | 55 | 45 | 55 | 46 | 52 |
| 28 | $\Delta UH_{NAc6S}GH_{NS,3S,6S}$ ($\alpha$) | 2.0 | 6.0 | 1.7 | 4.3 | 3.8 | 6.1 | 3.5 | 4.8 | 3.5 | 5.0 |
| 29 | $\Delta U_{2S}H_{NS6S}$ ($\beta$) | 5.5 | 6.5 | 3.9 | 9.5 | 5.8 | 8.7 | 3.6 | 6.0 | 4.4 | 9.1 |
| 30 | $\Delta U_{2S}H_{NS6S}I_{2S}$ ($\alpha$) | 0.00 | 0.5 | 0.00 | 0.00 | 0.00 | 0.05 | 0.00 | 0.1 | <0.2 | |
| 31 | $\Delta U_{2S}H_{NS6S}I_{2S}$ ($\beta$) | 0.00 | 0.5 | 0.00 | 0.00 | 0.00 | 0.05 | 0.00 | 0.1 | <0.2 | |
| 32 | $\Delta UH_{NS6S}GH_{NS3S6S}$ ($\alpha$) | 0.1 | 0.5 | 0.2 | 0.6 | 0.3 | 0.8 | 0.05 | 1.0 | 0.3 | 0.5 |
| 33 | $\Delta UH_{NS6S}GH_{NS3S6S}$ ($\beta$) | 0.1 | 0.5 | 0.2 | 0.6 | 0.3 | 0.8 | 0.05 | 1.0 | 0.3 | 0.5 |
| 34 | $\Delta U_{2S}H_{NS6S}I_{2S}H_{NS}$ (1,6 anhydro) | 0.00 | 0.5 | 0.00 | 0.00 | 0.00 | 0.05 | 0.00 | 0.1 | <0.2 | |
| 35 | $\Delta U_{2S}H_{NS3S6S}$ | 0.1 | 0.5 | 0.2 | 0.6 | 0.3 | 0.8 | 0.05 | 1.0 | 0.2 | 0.4 |
| 36 | $\Delta U_{2S}H_{NS6S}I_{2S}Man_{NS}$ (1,6 anhydro) | 0.00 | 0.5 | 0.00 | 0.00 | 0.00 | 0.05 | 0.00 | 0.1 | <0.2 | |
| 37 | $\Delta U_{2S}H_{NS6S}GH_{NS3S6S}$ ($\beta$) | 0.1 | 0.5 | 0.2 | 0.6 | 0.3 | 0.8 | 0.05 | 1.0 | 0.2 | 0.4 |
| 38 | $\Delta U_{2S}H_{NS6S}GH_{NS3S6S}$ ($\alpha$) | 0.2 | 1.2 | 0.5 | 1.5 | 0.1 | 0.8 | 0.05 | 1.8 | 0.5 | 0.8 | and if said structural moieties are present in an amount that falls within a range provided in the table, then processing the preparation by a process selected from the group consisting of: classifying, selecting, accepting, releasing, shipping, formulating, labeling, and packaging the UFH preparation.

3. The method of claim 1, wherein the processing step comprises formulating the LMWH preparation as an enoxaparin formulation.

4. The method of claim 2, wherein the processing step comprises selecting the UFH preparation as starting material to produce a low molecular weight heparin (LMWH).

5. The method of claim 4, wherein the LMWH is enoxaparin.

* * * * *